(12) United States Patent
Rubbert et al.

(10) Patent No.: US 9,539,062 B2
(45) Date of Patent: Jan. 10, 2017

(54) METHODS OF DESIGNING AND MANUFACTURING CUSTOMIZED DENTAL PROSTHESIS FOR PERIODONTAL OR OSSEOINTEGRATION AND RELATED SYSTEMS

(75) Inventors: Ruedger Rubbert, Berlin (DE); Ernst-Ulrich Berndt, Berlin (DE); Jakob Sebastian Marquard, Berlin (DE); Hauke Schmidt-Martens, Hamburg (DE); Lea Ellermeier Nesbit, Dallas, TX (US)

(73) Assignee: Natural Dental Implants, AG, Berlin (DE)

( * ) Notice: Subject to any disclaimer, the term of this patent is extended or adjusted under 35 U.S.C. 154(b) by 942 days.

(21) Appl. No.: 13/247,607

(22) Filed: Sep. 28, 2011

(65) Prior Publication Data

US 2012/0065756 A1 Mar. 15, 2012

Related U.S. Application Data

(63) Continuation-in-part of application No. 12/763,001, filed on Apr. 19, 2010, now Pat. No. 8,602,780, and a
(Continued)

(51) Int. Cl.
*A61C 8/00* (2006.01)
*A61C 5/00* (2006.01)
(Continued)

(52) U.S. Cl.
CPC ............. *A61C 5/007* (2013.01); *A61C 8/0012* (2013.01); *A61C 8/0018* (2013.01);
(Continued)

(58) Field of Classification Search
CPC ....................................... A61C 8/0048–8/0078
(Continued)

(56) References Cited

U.S. PATENT DOCUMENTS 2,210,424 A * 8/1940 Morrison ............. A61C 8/0036
433/175
2,721,387 A 10/1955 Ashuckian
(Continued)

FOREIGN PATENT DOCUMENTS

CA 2624830 A1 4/2007
DE 2729969 A1 1/1978
(Continued)

OTHER PUBLICATIONS

Non-Final Office Action issued in co-pending U.S. Appl. No. 12/247,843; dated Aug. 29, 2013; 34 pages.
(Continued)

*Primary Examiner* — Matthew Nelson
(74) *Attorney, Agent, or Firm* — Bracewell LLP

(57) ABSTRACT

Methods of manufacturing dental prosthesis/implants each to replace a non-functional natural tooth positioned in a jawbone of a specific pre-identified patient are provided. An example method includes the steps of receiving imaging data such as x-ray image data and surface scan data of a dental anatomy and/or a physical impression of the dental anatomy of a specific preidentified patient. The steps can also include forming a three-dimensional virtual model of at least portions of a non-functional natural tooth positioned in the jawbone of the specific pre-identified patient based on the imaging and surface scan data, virtually designing a dental implant based upon the virtual model, exporting the data describing the designed dental implant to a manufacturing machine, and custom manufacturing the dental implant for the specific patient.

46 Claims, 62 Drawing Sheets

Related U.S. Application Data continuation-in-part of application No. 11/724,261, filed on Mar. 15, 2007, now Pat. No. 7,708,557, and a continuation-in-part of application No. 11/549,782, filed on Oct. 16, 2006, now Pat. No. 8,454,362.

(60) Provisional application No. 61/454,450, filed on Mar. 18, 2011.

(51) Int. Cl.
| | | |
|---|---|---|
| *A61C 13/00* | (2006.01) | |
| *A61K 6/00* | (2006.01) | |
| *A61L 27/38* | (2006.01) | |
| *A61C 8/02* | (2006.01) | |
| *A61C 13/08* | (2006.01) | |
| *A61C 9/00* | (2006.01) | |

(52) U.S. Cl.
CPC .......... *A61C 8/0036* (2013.01); *A61C 8/0048* (2013.01); *A61C 13/0004* (2013.01); *A61K 6/0044* (2013.01); *A61L 27/3804* (2013.01); *A61L 27/3865* (2013.01); *A61C 8/0006* (2013.01); *A61C 8/0075* (2013.01); *A61C 9/0046* (2013.01); *A61C 13/0013* (2013.01); *A61C 13/0019* (2013.01); *A61C 13/082* (2013.01); *A61L 2430/12* (2013.01)

(58) Field of Classification Search
USPC .. 433/172–176, 191–195; 700/95–98; 703/2, 6–7
See application file for complete search history.

(56) References Cited

U.S. PATENT DOCUMENTS

| | | | |
|---|---|---|---|
| 2,792,628 A * | 5/1957 | Neumayer | A61C 13/082 433/206 |
| 3,628,248 A | 12/1971 | Kroder et al. | |
| 3,717,932 A * | 2/1973 | Brainin | A61C 13/30 433/175 |
| 3,984,914 A | 10/1976 | Schwartz | |
| 4,178,686 A | 12/1979 | Riess et al. | |
| 4,199,864 A | 4/1980 | Ashman | |
| 4,278,630 A | 7/1981 | Scheicher | |
| 4,504,229 A | 3/1985 | Garito et al. | |
| 4,531,566 A | 7/1985 | Boettcher | |
| 4,552,779 A * | 11/1985 | McClure | A61C 13/26 106/35 |
| 4,684,555 A | 8/1987 | Neumeyer | |
| 4,828,117 A | 5/1989 | Panzera et al. | |
| 5,002,488 A | 3/1991 | Homsy | |
| 5,004,422 A * | 4/1991 | Propper | A61C 8/0036 433/175 |
| 5,061,285 A | 10/1991 | Koch | |
| 5,094,618 A | 3/1992 | Sullivan | |
| 5,108,289 A | 4/1992 | Fukuyo | |
| 5,123,844 A | 6/1992 | Wakai et al. | |
| 5,264,215 A | 11/1993 | Nakabayashi et al. | |
| 5,562,450 A | 10/1996 | Gieloff et al. | |
| 5,691,905 A | 11/1997 | Dehoff et al. | |
| 5,725,376 A | 3/1998 | Poirier | |
| 5,725,378 A | 3/1998 | Wang | |
| 5,772,439 A | 6/1998 | Yamaoka et al. | |
| 5,800,175 A | 9/1998 | Zuk et al. | |
| 5,921,778 A | 7/1999 | Karmaker et al. | |
| 5,944,524 A | 8/1999 | Hill et al. | |
| 6,089,867 A | 7/2000 | Filho | |
| 6,099,313 A | 8/2000 | Dorken et al. | |
| 6,186,790 B1 | 2/2001 | Karmaker et al. | |
| 6,193,516 B1 | 2/2001 | Story | |
| 6,250,923 B1 | 6/2001 | Gibbs et al. | |
| 6,436,143 B1 | 8/2002 | Ross | |
| 6,447,295 B1 | 9/2002 | Kumar et al. | |
| 6,521,246 B2 | 2/2003 | Sapieszko et al. | |
| 6,534,197 B2 | 3/2003 | Noda et al. | |
| 6,589,525 B2 | 7/2003 | Gault | |
| 6,696,073 B2 | 2/2004 | Boyce et al. | |
| 6,702,855 B1 | 3/2004 | Steinemann et al. | |
| 6,755,651 B2 | 6/2004 | Brodbeck | |
| 6,788,986 B1 | 9/2004 | Traber | |
| 6,863,694 B1 | 3/2005 | Boyce | |
| 6,913,666 B1 | 7/2005 | Aeschlimann et al. | |
| 6,921,264 B2 | 7/2005 | Mayer et al. | |
| 6,955,540 B2 | 10/2005 | Mayer et al. | |
| 6,984,261 B2 | 1/2006 | Cummings et al. | |
| 7,008,226 B2 | 3/2006 | Mayer | |
| 7,105,182 B2 | 9/2006 | Szymaitis | |
| 7,110,594 B2 | 9/2006 | Jones et al. | |
| 7,156,655 B2 | 1/2007 | Sachdeva et al. | |
| 7,234,937 B2 | 6/2007 | Sachdeva et al. | |
| 7,333,874 B2 | 2/2008 | Taub et al. | |
| 7,377,782 B1 * | 5/2008 | Brosnihan | A61C 7/08 128/861 |
| 7,708,557 B2 | 5/2010 | Rubbert | |
| 7,774,084 B2 | 8/2010 | Cinader, Jr. | |
| 7,813,806 B2 | 10/2010 | Skiba | |
| 7,904,307 B2 | 3/2011 | Abolfathi | |
| 2001/0055745 A1 | 12/2001 | Gault | |
| 2002/0015934 A1 | 2/2002 | Rubbert et al. | |
| 2002/0102009 A1 | 8/2002 | Jones et al. | |
| 2002/0140137 A1 | 10/2002 | Sapieszko et al. | |
| 2003/0064349 A1 * | 4/2003 | Simmons, Jr. | A61C 8/001 433/173 |
| 2003/0118968 A1 | 6/2003 | Massoud | |
| 2004/0015327 A1 | 1/2004 | Sachdeva et al. | |
| 2004/0029068 A1 * | 2/2004 | Sachdeva et al. | A61C 7/00 433/24 |
| 2004/0038178 A1 | 2/2004 | Mayer et al. | |
| 2004/0053198 A1 | 3/2004 | Minevski et al. | |
| 2004/0110110 A1 * | 6/2004 | Chishti et al. | A61C 7/00 433/24 |
| 2004/0152034 A1 | 8/2004 | Cummings et al. | |
| 2004/0168610 A1 | 9/2004 | Conrad et al. | |
| 2004/0185418 A1 | 9/2004 | Schulter | |
| 2004/0197727 A1 * | 10/2004 | Sachdeva et al. | A61C 7/00 433/24 |
| 2005/0033427 A1 | 2/2005 | Freilich et al. | |
| 2005/0038498 A1 | 2/2005 | Dubrow et al. | |
| 2005/0048440 A1 * | 3/2005 | Feng | A61C 8/0036 433/175 |
| 2005/0079469 A1 | 4/2005 | Akagawa et al. | |
| 2005/0084513 A1 | 4/2005 | Tang | |
| 2005/0106534 A1 | 5/2005 | Gahlert | |
| 2005/0142517 A1 | 6/2005 | Frysh et al. | |
| 2005/0186540 A1 | 8/2005 | Taub et al. | |
| 2005/0260541 A1 | 11/2005 | McDevitt | |
| 2006/0003292 A1 | 1/2006 | Lauren et al. | |
| 2006/0078847 A1 * | 4/2006 | Kwan | A61C 8/0001 433/174 |
| 2006/0105295 A1 * | 5/2006 | Mayer et al. | A61B 17/68 433/173 |
| 2006/0154203 A1 | 7/2006 | Emanuelli | |
| 2007/0015110 A1 | 1/2007 | Zhang et al. | |
| 2007/0072152 A1 | 3/2007 | Jaghab | |
| 2007/0154866 A1 | 7/2007 | Hall | |
| 2007/0264612 A1 * | 11/2007 | Mount | A61C 8/00 433/173 |
| 2008/0090207 A1 | 4/2008 | Rubbert | |
| 2008/0090208 A1 | 4/2008 | Rubbert | |
| 2008/0213725 A1 | 9/2008 | Adilstam et al. | |
| 2009/0042167 A1 | 2/2009 | Van Der Zel | |
| 2009/0087817 A1 | 4/2009 | Jansen | |
| 2009/0319068 A1 * | 12/2009 | Sager | A61C 5/10 700/98 |
| 2010/0203478 A1 | 8/2010 | Rubbert | |
| 2010/0261141 A1 | 10/2010 | Ajlouni | |
| 2011/0010187 A1 | 1/2011 | Andersson et al. | |
| 2012/0064489 A1 | 3/2012 | Rubbert et al. | |
| 2012/0065756 A1 | 3/2012 | Rubbert et al. | |
| 2012/0070802 A1 * | 3/2012 | Woodward, III | A61C 8/0036 433/175 |

(56) References Cited

U.S. PATENT DOCUMENTS

FOREIGN PATENT DOCUMENTS

| DE | 197 53 577 A1 | 6/1999 |
|---|---|---|
| DE | 10020894 A1 | 4/2000 |
| DE | 10109118 A1 | 9/2002 |
| DE | 103 58 680 A1 | 7/2005 |
| EP | 0053903 A1 | 6/1982 |
| EP | 1073381 | 11/1999 |
| EP | 1150620 | 8/2000 |
| EP | 2 025 303 A1 | 2/2009 |
| EP | 2087852 A1 | 8/2009 |
| EP | 2087853 A1 | 8/2009 |
| EP | 2095789 | 9/2009 |
| JP | 07014400 | 1/1995 |
| WO | 0134056 A1 | 5/2001 |
| WO | 2004056405 A2 | 7/2004 |
| WO | 2005057439 A1 | 6/2005 |
| WO | 2005105164 A1 | 11/2005 |
| WO | 2006031096 A1 | 3/2006 |
| WO | 2006060836 A1 | 6/2006 |
| WO | 2007006258 A1 | 1/2007 |
| WO | 2007038817 A1 | 4/2007 |
| WO | 2007125323 A1 | 11/2007 |
| WO | 2007131337 A1 | 11/2007 |
| WO | 2008017472 A2 | 2/2008 |
| WO | 2008047204 A3 | 4/2008 |
| WO | 2009020447 A1 | 2/2009 |

OTHER PUBLICATIONS

Non-Final Office Action issued in related U.S. Appl. No. 11/549,782; dated Feb. 7, 2012; 22 pages.
Office Action of co-pending U.S. Appl. No. 11/549,782, dated Aug. 3, 2012.
Exodontia: the Ogram System; What is Ogram System Technology; Academy of General Dentistry; http://orgramsystem.com/ogram/WhatisOST.html; Jan. 26, 2007 (2 pages).
Department of Dentistry; Research—Department of Dentistry—University of Alberta; http://www.dentualberta.ca/; Jan. 26, 2007 (1 page).
Bartold, et al., Tissue Engineering: A New Paradigm for Periodontal Regeneration Based on Molecular and Cell Biology, Periodontology 2000, vol. 24, pp. 253-269 (17 pages).
Buser, et al., Formation of a Periodontal Ligament Around Titanium Implants, J Periodontol, Sep. 1990, vol. 61, No. 9, pp. 597-601 (5 pages).
El-Homsi, et al., Simulating Periodontal Effects in Dental Osseointegrated Implants: Effect of an Intramobile Damping Element on the Fatigue strength of Dental Implants—An in Vitro Test Method, Quintessence International, vol. 35, No. 6, 2004, pp. 449-455 (7 pages).
Grzesik, et al., Cementum and Periodontal Wound Healing and Regeneration, Crit Rev Oral Bioi Med, 2002, vol. 13, No. 6, pp. 474-484 (11 pages).
Lang, et al., Attachment Formation Following Replantation of Cultured Cells into Periodontal Defects—a Study in Minipigs, J Dent Res, Feb. 1998, vol. 77, No. 2, pp. 393-405 (13 pages).
Lin, et al., Dental Implants with the Periodontium: A New Approach for the Restoration of Missing Teeth, Elsevier, Medical Hypotheses, 2009, vol. 72, pp. 58-61 (4 pages).
Malekzadeh, et al., Isolation of Human Osteoblast-Like Cells and in Vitro Amplification for Tissue Engineering, J Periodontol, Nov. 1998, vol. 69, No. 11, pp. 1256-1262 (7 pages).
Mensor, et al., Compliant Keeper System Replication of the Periodontal Ligament Protective Damping Function for Implants, The Journal of Prosthetic Dentistry, Nov. 1998, vol. 80, No. 5, pp. 565-569 (5 pages).
Metzger, et al., Manufacturing Splints for Orthognathic Surgery Using a Three-Dimensional Printer, http://www.aadmrt.com/currents/metzgeretaLwinter_09yrint.htm, Apr. 8, 2009 (14 pages).
Reichert et al., Tuning Cell Adhesion on PTFE Surfaces by Laser Induced Microstructures, Advanced Engineering Materials, 2007, vol. 9, No. 12, Wiley-VCH Verlag GmbH & Co. KGaA, Weinheim, pp. 1104-1113 (10 pages).
Van Dijk, et al., Cell-Seeding of Periodontal Ligament Fibroblasts, J Clin Periodontol, 1991, vol. 18, pp. 196-199 (4 pages).
Warrer, et al., Periodontal Ligament Formation Around Different Types of Dental Titanium Implants. I. The Self-Tapping Screw Type Implant System, J Periodontol, Jan. 1993, vol. 64, No. 1, pp. 29-34 (6 pages).
International Preliminary Report on Patentability and Written Opinion issued in PCT Application No. PCT/IB2007/003072 dated Apr. 22, 2009 (14 pages).
European Search Report issued in EP Application No. 09075155.3 dated Jul. 29, 2009 (7 pages).
International Search Report issued in PCT/IB2007/003072 dated Jul. 22, 2008 (9 pages).
Patient Information Leaflet Orthognathic Surgery, British Orthodontic Society (2 pages).
European Search Report issued in EP Application No. 09075153.8 dated Jul. 8, 2009 (7 pages).
E. Nuzzolese, "Intentional Dental Reimplantation: A Case Report," The Journal of Contemporary Dental Practice, vol. 5, No. 3, Aug. 15, 2004. pp. 1-7 (7 pages).
K. Wong, "Exarticulation and Reimplantation Utilizing Guided Tissue Regeneration: A Case Report," Quintessence International, vol. 33, No. 2, 2002, pp. 101-109 (9 pages).
A. Goerig, "Successful Intentional Reimplantation of Manidular Molars," Quintessence International, vol. 19, No. 8, 1988, pp. 585-588 (4 pages).
D. Benedict, "Reimplantation of Teeth," Quintessence International, vol. 9, 1989, pp. 41-47 (4 pages).
Kerr Corp., Datasheet, "Bioplant, Biocompatible, Synthetic, Osteoconductive," 2006 (2 pages).
A. Touchstone, "Simplifying CAD/CAM Dentistry," Dental Products Report, Nov. 2005, An Advanstar Publication, pp. 1-20 (20 pages).
Juxtaendo, website article,"Juxtaendo" Dentistry Implant (A. DiGiulio), downloaded from San Babila Day Hospital (Italy), Oct. 18, 2006 (2 pages).
A. Veis, "Specific Amelogenin Gene Spice Product Have Signaling Effect on Cells in Culture and in Implants in Vivo," The Journal of Biological Chemistry, 2000 by the American Society for Biochemistry and Molecular Biology, Inc., vol. 275, No. 52, pp. 41263-41272, Dec. 29, 2000 (10 pages).
F. Kawana, "Porcine Enamel Matrix Derivative Enhances Trabecular Bone Regeneration During Wound Healing of Injure Rat Femur," The Anatomical Record, 2001, vol. 264, pp. 438-446 (9 pages).
M. Iijima. Control of Ostacalcium Phosphate and Apatite Crystal Growth by Amelogenin Matrices, Journal of Materials Chemistry, 2004, vol. 14, pp. 2189-2199 (11 pages).
A.M. Hoang, "Amelogenin is a Cell Adhesion Protein," Journal of Dental Research, 2000, http://www.sagepublications.com, vol. 81(7), pp. 497-500 (5 pages).
L. Hammartrom, "Periodontal Regeneration in a Buccal Dehisence Model in Monkeys After Application of Enamel Matrix Proteins," Journal of Clinical Periodontal, 1997, vol. 24, pp. 669-677 (9 pages).
B.D. Boyan, "Porcine Fetal Enamel Matrix Derivative Enhances Bone Formation Induced by Demineralized Freeze Dried Bone Allograft in Vivo," J. Periodontal, 2000, vol. 71, No. 8, pp. 1278-1286 (9 pages).
A. Veis, "Amelogenin Gene Splice Products: Potential Signaling Molecules," CML Cellular and Molecular Life Sciences, Birkhauser Verlag, Basel, vol. 60 (2003), pp. 38-55 (18 pages).
F. Schwartz,"Effect of Enamel Matrix Protein Derivative on the Attachment, Proliferation, and Viability of Human SAOs2 Osteoblasts on Titanium Implants," Clinical Oral Investment, Springer-Verlag (2004), vol. 8, pp. 165-171 (7 pages).
K. Tompkins, "Two Related Low Molecular Mass Polypeptide Isoforms of Amelogenin Have Distinct Activities in Mouse Tooth

(56) References Cited

OTHER PUBLICATIONS

Germ Differentiation In Vitro," Journal of Bone and Mineral Research, vol. 20, No. 2, 2005. pp. 341-349 (9 pages).

H.B. Wen, "Modulation of Apatite Crystal Growth on Bioglass by Recombinant Amelogenin," Biomaterials, vol. 20, (1999), pp. 1717-1725 (9 pages).

H.B. Wen, "Modification of Calcium-Phosphate Coating on Titanium by Recombinant Amelogenin," Center for Craniofacial Molecular Biology, School of Dentistry, Univ. of Southern California, 2003 Wiley Periodicals, Inc., pp. 483-490 (8 pages).

L. Heijl, "Periodontal Regeneration With Enamel Matrix Derivative in One Human Experimental Defect," Journal of Clinical Periodontalology, 1997, vol. 24, pp. 693-696 (4 pages).

A.G. Fincham, "The Structural Biology of the Developing Dental Enamel Matrix," Journal of Structural Biology, 1999, vol. 126, pp. 270-299 (30 pages).

C. Du, "Supramolecular Assembly of Amelogenin Nanospheres Into Birefringent Microribbons," Science, 2005, vol. 307, pp. 1450-1454 (7 pages).

Strauman, "Emdogain, The Reliable Solution for Periodontal Treatment," http//www.Straumann.com, Mar. 2006 (11 pages).

Berndt et al., "Topologically Structured Surfaces and Coating Treatments for Peridontal and Osseo-Integration", Natural Dental Implants AG (2009), pp. 1-5.

Barsch, "Verbesserung des Haftverbundes fur Vollkeramikkronen aus Y-TZP durch Femtosekundenlaser-Mikrostrukturierung", 35 (10) Quintessenz Zahntech (2009), pp. 1322-1332.

Spouge, "Oral Pathology", The C.V. Mosby Co., Saint Louis (1973).

Vannier, "Craniofacial computed tomography scanning: technology, applications and future trends", 6 (Suppl 1) Orthod. Craniofacial Res. (2003), pp. 23-30.

"Introduction to Digital Dentistry and Guided Surgery", 3D Diagnostix.com, http://www.3ddx.com/guided_surgery.htm [Oct. 7, 2011 7:21:51 PM].

Christensen et al., "Role of Rapid Digital Manufacture in Planning and Implementation of Complex Medical Treatments", from Advanced Manufacturing Technology for Medical Applications: Reverse Engineering, Software Conversion and Rapid Prototyping, I. Gibson (Edi.), John Wiley & Sons, Ltd. (2005), pp. 15-30.

Ganz, "Use of Conventional CT and Cone Beam for Improved Dental Diagnostics and Implant Planning", Amer. Assoc. of Dental Radiographic Technicians Newsletter (Spring 2005), http://aadmrt.com/currents/ganz_spring_2005_print.htm [Oct. 18, 2011 2:22:24 PM].

Hatcher, "Cone Beam CT for Pre-Surgical Assessment of Implant Sites", Amer. Assoc. of Dental Radiographic Technicians Newsletter (Summer 2005).

Partial File History of U.S. Appl. No. 11/562,953 (Hall), filed Nov. 22, 2006.

"Materialise Scores Against Nobel Biocare: More Changes Looming in the Surgical Guide Market?", http://www.osseonews.com/materialise-against-nobel-biocare/print/[Oct. 17, 2011 7:41:51 PM].

Ganz, Use of Stereolithographic Models as Diagnostic and restorative Aids for predictable Immediate Loading of Implants, 15(10) Pract. Proced. Aesthet. Dent. (2003), pp. 763-771.

Dakhno, Abstract—"Maxillolofacial surgery planning for the insertion of dental implants obtained from CT data using the SimPlant interactive software", 2(2) Implantology & Paradontology & Osteology (2005), pp. 23-27.

Mupparapu, "Implant Imaging for the Dentist", 70(1) J. Canadian Dent. Assoc. (2004), pp. 32-32g.

Goerig et al., "Successful intentional reimplantation of mandibular molars", 19(8) Quintessence Int'l (1988), pp. 585-588.

Office Action from co-pending U.S. Appl. No. 11/549,782, dated Feb. 7, 2012.

Search Report for Related Application PCT/EP2013/053246 dated Jun. 28, 2013.

Non-final Office Action, dated Sep. 17, 2012 from co-pending U.S. Appl. No. 12/763,001.

* cited by examiner

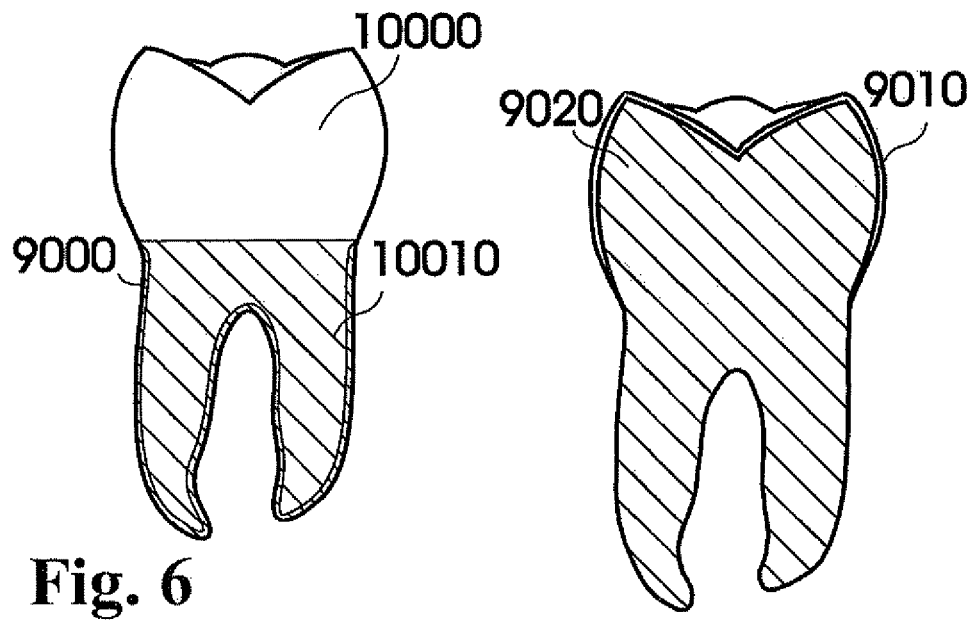
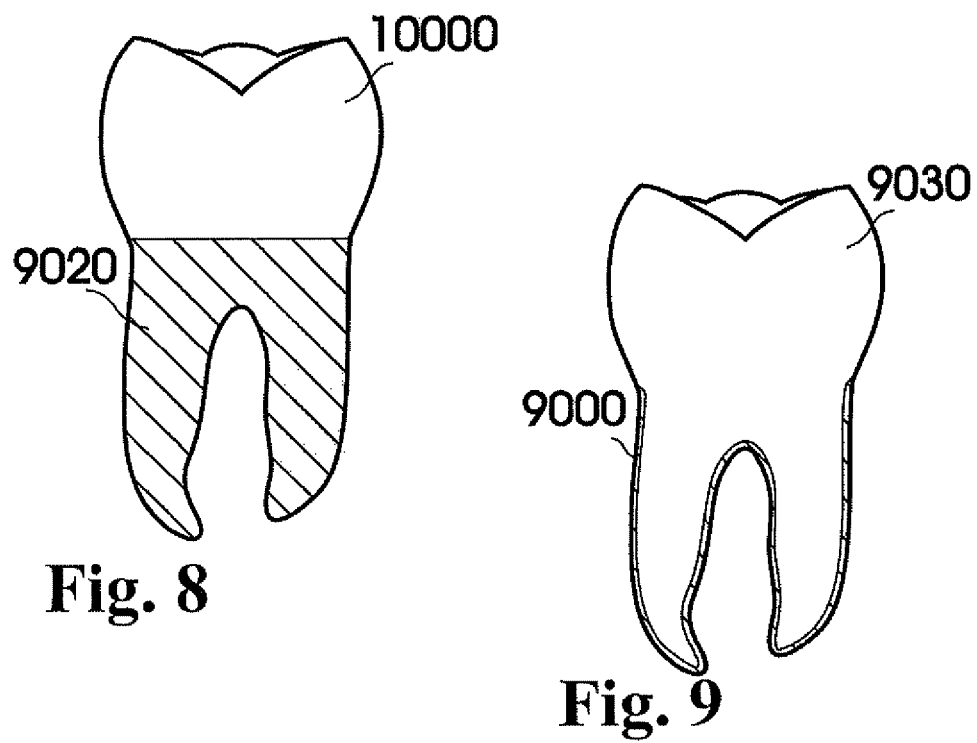

```
Solid MYSOLID
   facet normal   -0.470578    -0.335539    0.816070
      outer loop
         vertex   0.000000e+00  -12.5120    1.76950
         vertex   0.460000e-02  -11.7876    2.07000
         vertex   -1.78420      -11.8027    1.03230
      end loop
   end facet
   facet normal   -0.470359    -0.336719    -0.815710
      outer loop
         vertex   -1.53240      -12.5120    -0.884700
         vertex   1.78420       -11.8027    -1.03230
         vertex   0.46000e-02   -11.7876    -2.07000
      end loop
   end facet
   facet normal   0.939923     -0.341387    0.000000e+00
      outer loop
         vertex   1.53240       -12.5120    -0.884700
         vertex   1.80230       -11.7689    -1.03730
         vertex   1.80230       -11.7689    1.03730
      end loop
   end facet
   facet normal   0.414021     -0.560697    0.717081
      outer loop
         vertex   1.80230       -11.7689    1.03730
         vertex   2.47780       -10.5155    1.62820
         vertex   -0.342400     -10.5144    3.25650
      end loop
   end facet
```

Fig. 32

```
% PRG001
N10 G17 G90 T11 F6000 S12000
N20 G00 X-20 Y0 Z50
N30 G01 X-20 Y0 Z5
N40 G01 X600 Y0 Z-5
N50 G03 X600 Y400 I600 I200 Z-5
F2000
N60 G01 X300 Y400 Z-5 F6000
N70 G01 X300 Y300 Z-5
N80 G01 X0 Y300 Z-5
N80 G01 X0 Y-20 Z-5
N100 G01 X0 Y-20 Z50
N110
 .
 .
 .
NXXX M30
```

Fig. 33

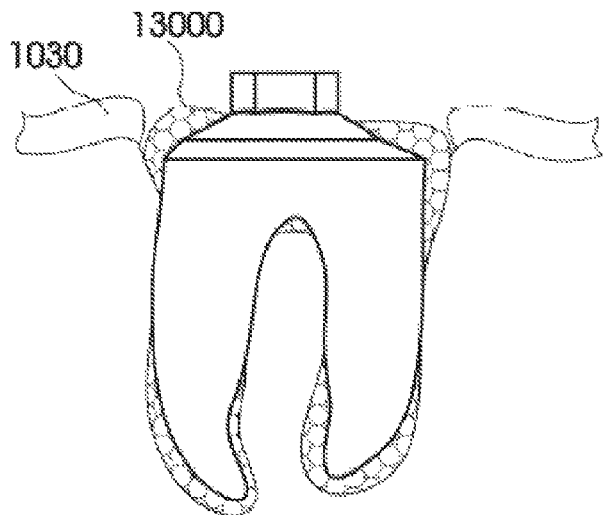

Fig. 34

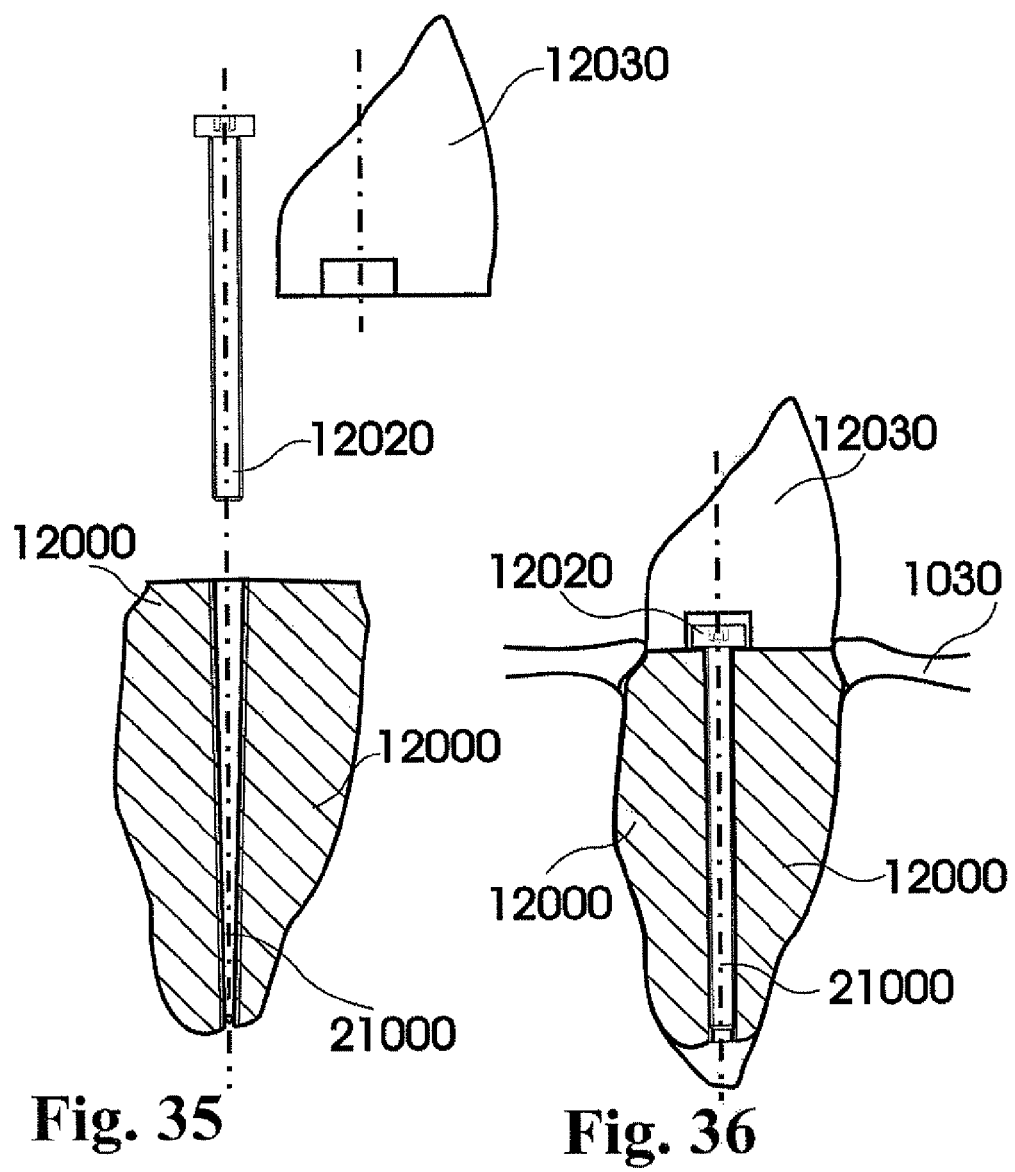

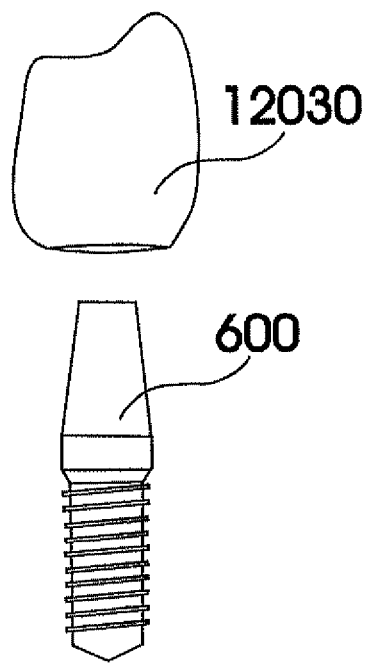
Fig. 37
Prior Art
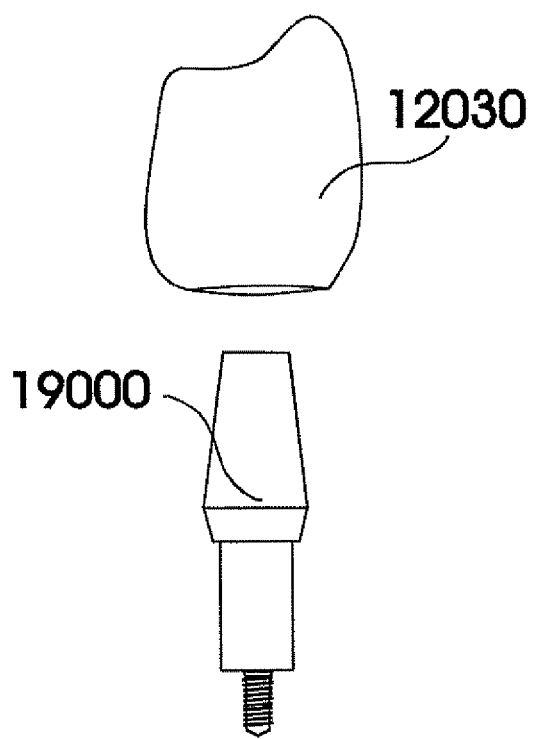
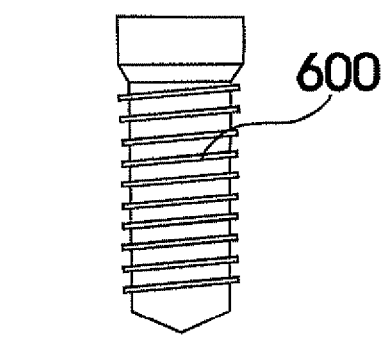
Fig. 38
Prior Art

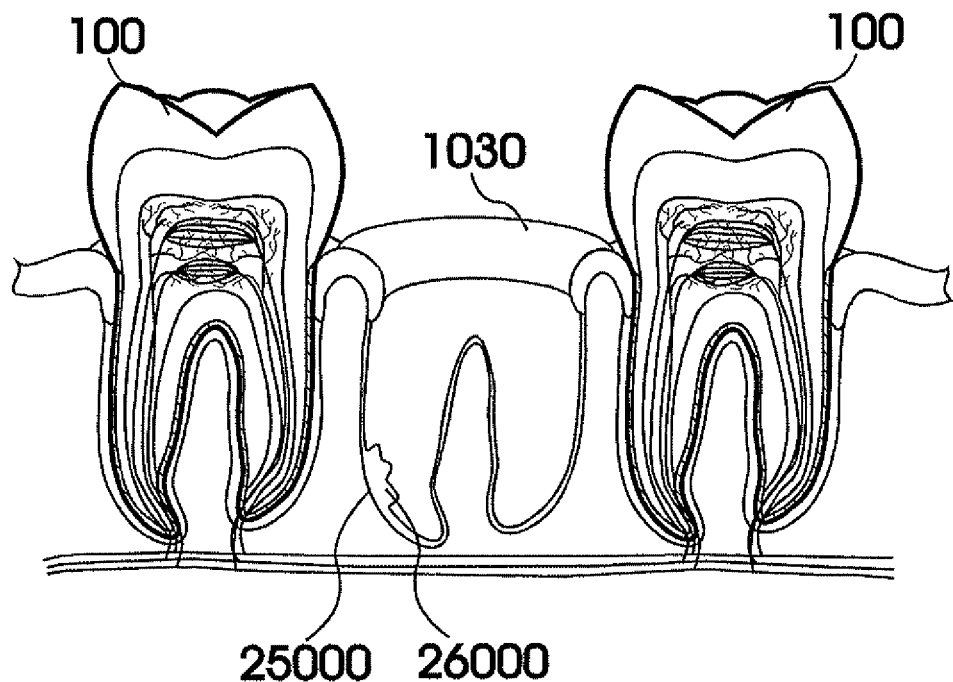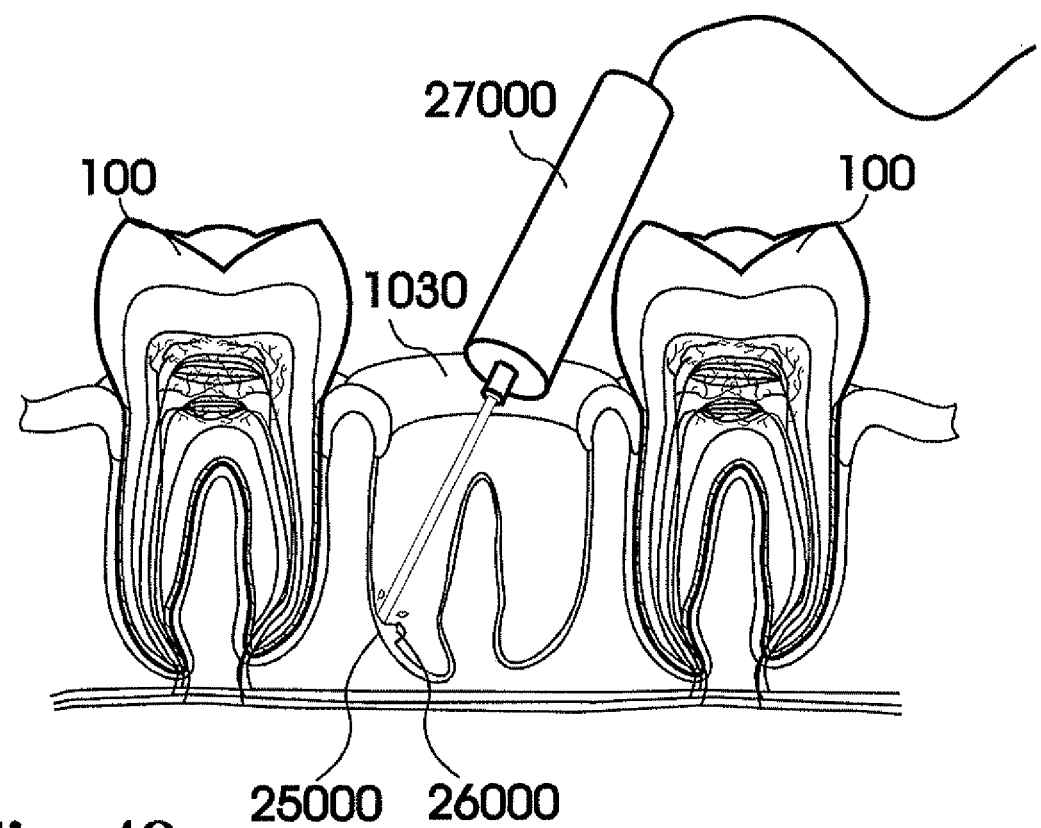
Fig. 48

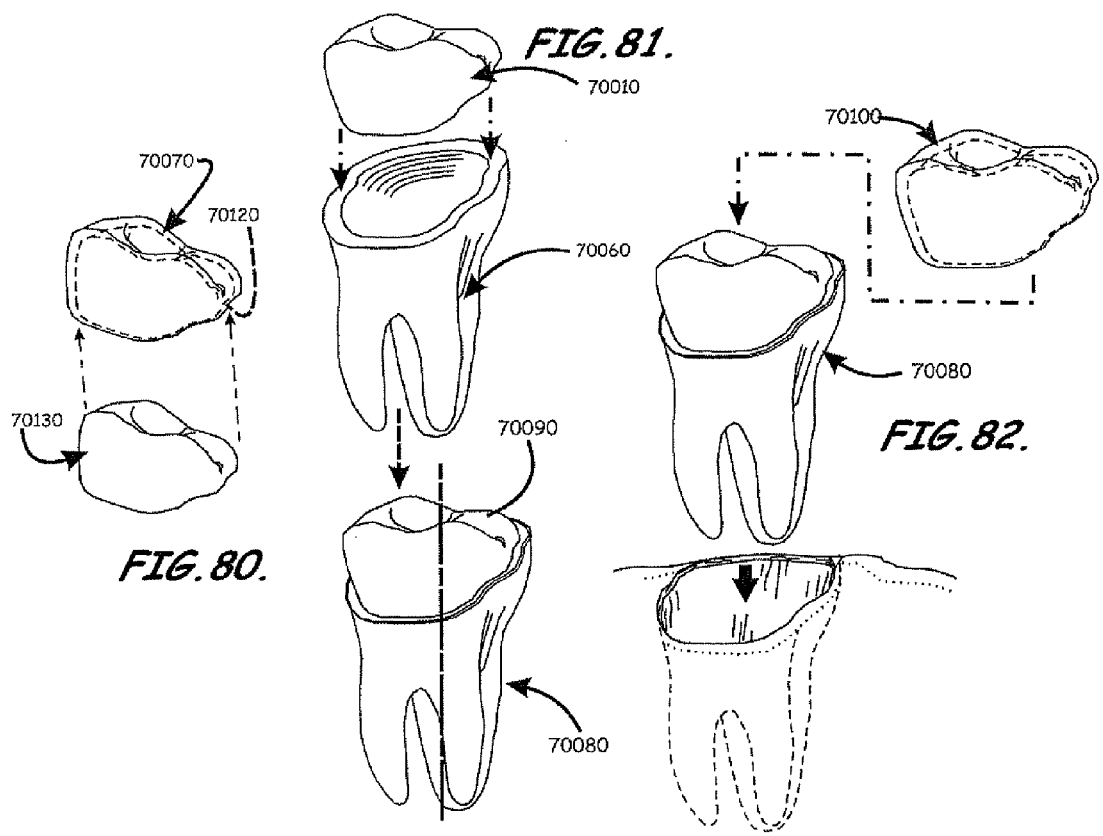

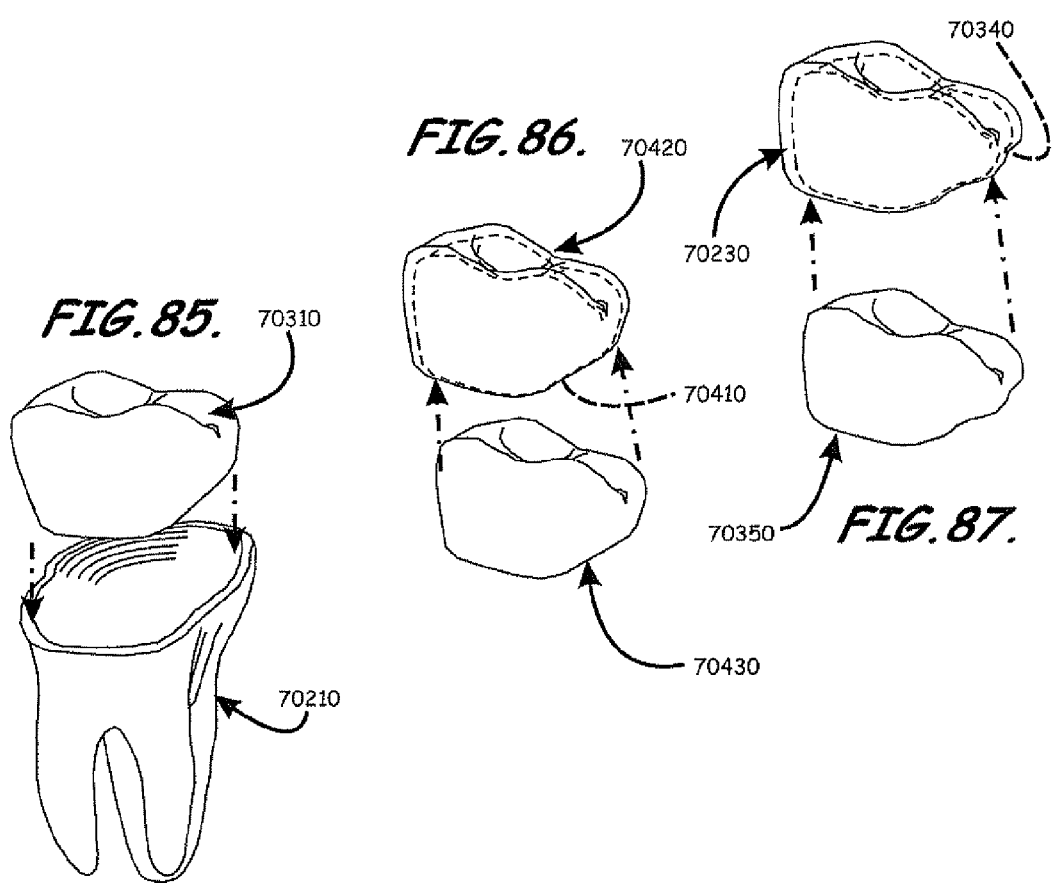

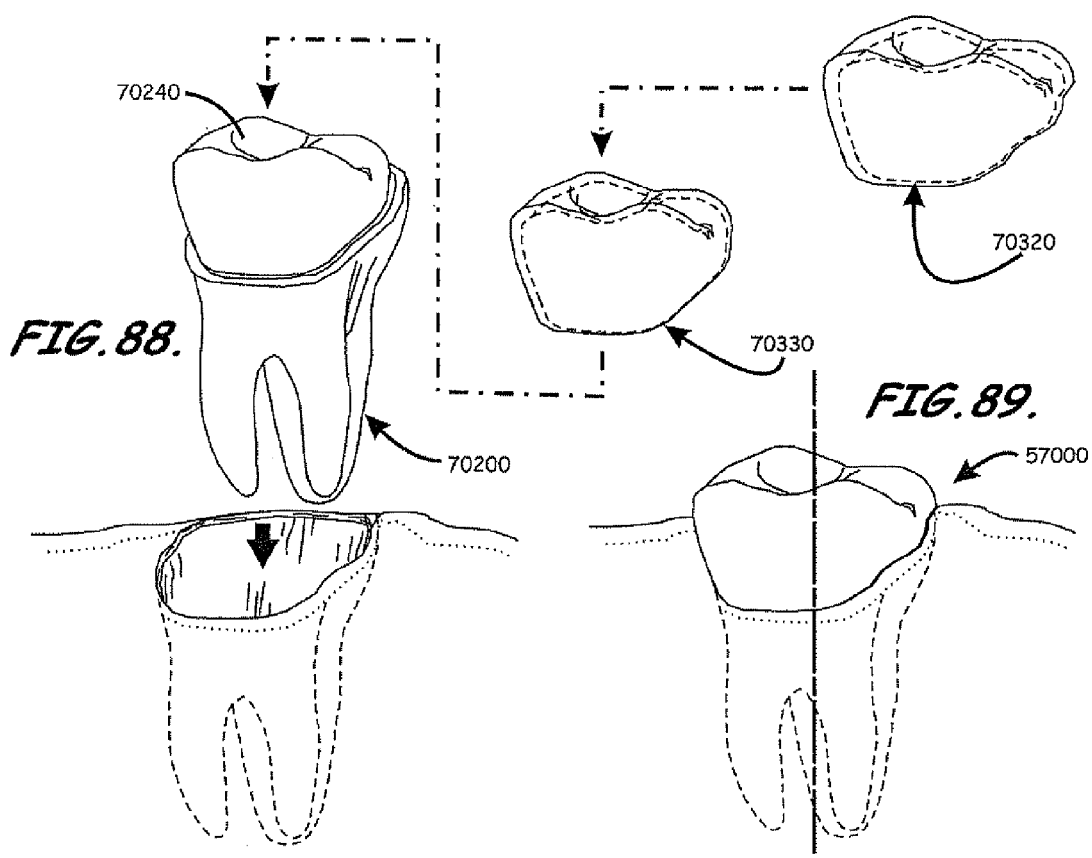

METHODS OF DESIGNING AND MANUFACTURING CUSTOMIZED DENTAL PROSTHESIS FOR PERIODONTAL OR OSSEOINTEGRATION AND RELATED SYSTEMS

RELATED APPLICATIONS

This patent application is a non-provisional and claims priority to and the benefit of U.S. Patent Application No. 61/454,450 filed on Mar. 18, 2011, and is a continuation-in-part of and claims priority to and the benefit of U.S. patent application Ser. No. 12/763,001, filed Apr. 19, 2010, and is a continuation-in-part of and claims priority to and the benefit of U.S. patent application Ser. No. 11/724,261, filed Mar. 15, 2007, now U.S. Pat. No. 7,708,557, which is a continuation-in-part of co-pending U.S. patent application Ser. No. 11/549,782 filed on Oct. 16, 2006, each incorporated by reference in its entirety.

BACKGROUND OF THE INVENTION

Field of the Invention

The invention relates generally to the field of dentistry, and more particularly to the field of dental restorations, implants and prostheses. The invention further relates to computer assisted and conventional systems and methods for designing and manufacturing such custom dental prosthesis.

Description of Related Art

Human teeth serve a variety of functions. Not only are they important for chewing food, but they also necessary to properly pronounce certain consonants, especially fizzle- and S-sounds. Furthermore, teeth play a major role in our personal appearance. While, healthy and well aligned teeth are an ideal of beauty and appear as a cosmetic sign of youth and success.

Although various preventive measures, like frequent tooth brushing and flossing, and drinking fluoridized or iodized water are widely accepted and used, the great majority of people are sooner or later challenged with dental fillings, restorations implants, and/or prostheses.

A major goal in dentistry is to postpone loss of teeth as long as possible. Another goal is certainly to provide comfortable prostheses with a broad scope/indication and a long lasting life-time.

Generally, the number of available restorative and prosthetic options is limited. Typically fillings, inlays, and crowns are used if the root and its embedding periodontal structure are healthy, and sufficient as support for such restorative partial prostheses. Traditionally, if the original tooth can no longer be used; the use of bridges or non-customized osseointegrated implants is indicated. In this context, several negative aspects are to be endured. In order to provide the support structure for a bridge, adjacent teeth are ground, and healthy enamel is partially destroyed. Osseointegrated implants are drastically invasive and the gingiva-implant interface is often the cause of chronic local infection. Additionally, all the aforementioned restorative and prosthetic options have a limited average lifetime. Removable dentures are certainly the final prosthetic option.

When a tooth is partially damaged, either by caries or mechanical impact, the missing portion should in most cases be replaced. As long as a tooth provides enough structural strength to support a prosthesis, for example, an inlay or a crown, this will typically be the preferred solution. However, if the loss of tooth substance is severe, this may not be applicable. In these cases, a bridge can be applied, enduring the aforementioned negative consequences. Another option is to replace the tooth with an implant.

There are many methods or options for replacing missing teeth. Off-the-shelf or pre-shaped osseointegrated dental implants are one of the options. Osseointegration means the direct contact of the implant surface with the bone without a fibrous connective tissue interface (natural teeth are typically not in direct contact with the bone, but are connected to the bone by ligaments). The use of such dental implants includes a wide variety of implant designs and materials, use of implants in different locations in the mouth and use of a variety of surgical protocols.

Endosteal implants are placed into the bone, like natural tooth roots. They can provide an anchor for one or more artificial teeth. They are the most commonly used type of implants. There are various types of endosteal implants, for example, screws, cylinders, cones, plates and blades. The generic screw, cylinder and cone types of implants are sometimes called "root-form" type. Such generic root-form implants that replace a single tooth generally consist of three parts, the actual implant-root for osseointegration, an abutment and the artificial crown. The interfaces between the three aforementioned parts are critical in respect to the sealing quality between said three parts. Bacterial infections can be caused if the sealing is compromised in regards to its short, mid and long-term stability.

Sometimes implant designs that actually consolidate two of said three parts, for example, the implant-root to be osseointegrated and the abutment, are referred to as one-piece implants.

Such three-part implant designs have a first sub-gingival joint between the implant screw and the abutment. The first joint is in its height placed adjacent to the bone crest of the jaw of the implant-receiving patient. The second joint is placed iso- or supra-gingival, which means on the same vertical height of the mouth facing surface of the gingiva or beyond the trans-gingival portion of the overall implant design. The first joint between the implant screw and abutment is especially under the static and dynamic stress of mastication forces, and is exposed as an area where bacteria may congregate, causing a chronically infection.

Contrary hereto, the term "one-piece" implant as used hereinafter is meant to refer to the integration of all three parts: the implant root, the abutment, and the crown. The term "immediate placing" of an implant is used if the integration of the implant into the bone occurs a short term after the extraction of a tooth. If such implants have a reasonable initial contact stability with the bone directly after being inserted, the so called primary stability, then such implants are called "immediately loaded", which means that the osseo-integrative stability, the so called secondary stability, does not need to be developed before performing the following process steps: making an impression of the abutment part of the implant in conjunction with the gingiva and the adjacent teeth situation, then fabricating the crown, implementing the crown, and actually allowing the patient to use the implant for mastication.

Subperiosteal implants are implants that are placed over the bone in cases where the bone has atrophied and jaw structure is limited. Subperiosteal implants are customized metal frameworks, providing the equivalent of multiple tooth roots. They can be applied in a limited area or in the entire mouth. After application, natural tissue membrane or bone will grow back around the implant, thus providing more stability. Posts protrude through the gum to hold the prosthesis.

Traditionally, osseointegrated dental implants are placed in bone and covered by mucosa during the immediate post-operative healing period. At four to eight months, a second surgical procedure is performed to expose the implant so it may be loaded with various types of dental crowns. In recent years, immediate implant placement following tooth extraction and immediate crown loading after surgical placement has become more common.

Generic ceramic dental implants are available made from yttrium-stabilized zirconia ceramics. Although such ceramic materials are due to its internal crystal structure and mechanisms able to suppress micro-cracks, it has been reported that in the moist-warm environment of the human body the long term stability of yttrium-stabilized zirconia ceramics is compromised to the extent that respective dental implants cannot be considered fracture-safe for the life-time expectations established in the industry.

However, the success rate and the in-vivo life time of osseointegrated dental implants are limited, and the surgical procedure is heavily invasive, because the bone needs to be drilled or ground in order to be adapted to the shape of the non-customized implants. Furthermore, osseointegrated implants are a limiting factor in a later orthodontic treatment. Problems relating to nerve transposition, osseous grafting, ridge augmentation, and sinus augmentation of osseointegrated dental implants, and/or to tissue health adjacent to dental implants have also been reported. Patients often complain about chronically infected periodontal structure caused by osseointegrated implants.

In cases where a tooth is not severely damaged, and would be ready to receive a partial restoration, but an intra-oral repair is impossible due to access problems, or a reverse root canal treatment is required, an alternative method is the intentional re-implantation. The tooth is extracted, repaired, and re-integrated into the existing periodontal structure of a dental patient. Nuzzolese et al. wrote in the Journal of Contemporary Dental Practice, Volume 5, No. 3, Aug. 15, 2004: "It is well known dental reimplantation is indicated following traumatic avulsion by the preservation of cellular vitality in the periodontal ligament and under conditions of asepsis. The rate of endodontic success at five years reported in the literature ranges between 70% and 91%. However, intentional dental reimplantation is an effective strategy for the treatment of teeth that would be difficult, if not impossible, to treat using traditional root canal therapy. Different prognoses exist for intentional dental reimplantation and trauma-related reimplantation. This is due to such important variables such as the level of cellular vitality in the periodontal ligament; the degree of trauma to surrounding tissues, and the degree of asepsis when a tooth is removed. Surgical extraction is more favorable in this regard compared to a traumatic avulsion scenario." Although this method is not yet widely used, the reported success rates are noteworthy. Reported are also autogenous and allogenic transplantation of a healthy natural tooth into the extraction socket for parodontal/periodontal integration. A disadvantage relating to all such techniques is certainly that the specific tooth to be reimplanted or transplanted still needs an overall reasonable condition and prognosis to justify an intentional re-implantation and that only certain root and root canal deficiencies can be repaired this way.

Various publications reporting that the prognosis of intentional reimplanted or transplanted teeth is significantly better than the reimplantation after a traumatic extraction, since the extraction is surgically controlled and relatively aseptic techniques are utilized. Spouge writes in his Oral Pathology, Mosby, Saint Louis 1973; "The majority of reimplantations however are clinically successful, and the teeth are retained firmly in the socket for the appropriate 5 year period. However, despite the apparent success, most of them show localized ankylosis and gross resorption of the root at the end of this time. The fibrous attachment that develops in the new periodontal ligament area often involves the formation of an immature type of connective tissue whose fibers remain tangential to the root surface rather than becoming physiologically oriented. There is experimental evidence to suggest that formation of a physiologic periodontium is more easily achieved in condition where the viability of the original periodontal ligament is maintained. In keeping with this, the prognosis for clinical success in a reimplanted tooth fall rapidly if is have been completely dislocated from its socket for more than 24 hours." Wong suggests in Quintessence International, Vol. 33. No. 2, 2002 a surgical "exarticulation" method, where the removal of the tooth from its socket is achieved "(after the incision of the crestal periodontal ligament fibers with micro-blades) with a combination of luxation and gentle, rotary, reciprocating movements" in order to minimize physical trauma to the excising periodontium. Goerig et al. recommends in Quintessence International, Vol. 19, No. 8, 1988 a sectioning procedure where a molar tooth is cut in half dividing the roots in order to minimize the damage of the existing periodontal ligament. The Ogram System (www.ogramsystem.com) provides a tooth removal protocol promising no or very little trauma of the surrounding tissue.

EI-Bialy et al. from the University of Alberta, Canada report the stimulation of jaw growth and tissue healing by directly applying ultrasound vibes to the tooth of interest. In this context it is known to those skilled in the art that the alternating "load" of dental structures in patients' day-to-day use of their dentition activates healing processes while a protection against or the avoidance of such alternating load causes resorption of roots, bone and soft tissue.

U.S. Pat. No, 5,562,450 references as prior art the German application DE 27 29 969 A1, which is incorporated herein by reference in its entirety, describing the osseintegration of, an implant that is substantially a copy of an extracted human tooth fabricated by a process involving copy milling. In order to be successfully osseointegrated the connective tissue (e.g., ligament) remaining in the extraction socket needs to be removed by being scraped out or curetted. The '450 patent recognizes the need to create a compression pressure between the bone and the implant in order to reach reasonable primary stability of the implant and teaches therefore to dimensionally enlarge the anatomical shape of the implant over the extracted tooth to fill the extraction socket.

Rubbert and Berndt reference in the article "Topologically Structured Surfaces and Coating Treatments for Periodontal and Osseo-Integration" published on Apr. 7, 2009, which is incorporated herein by reference in its entirety, various aspects of surface condition and treatments of dental implants and prostheses.

U.S. Pat. No. 6,099,313 discloses a dental implant for osseointegration having a bone-contact section which is root-shaped with an apical extension and an abutment described as a build-up section for fastening a crown.

All such restorative and prosthetic options and methodologies are deficient—being heavily invasive and/or limited in their respective scope. There has not been recognition, until now by the inventors, of the need for a product, systems, and methods related to the integration of dental prosthesis such as artificial tooth, bridges, or segments of the dentition that includes (a) custom-shaped root structures to be osseointegrated as one piece, (b) custom-made positioning and fixation splints for achieving primary stability, and (c) even more beneficial, parts to be integrated into the existing periodontal structure of an individual patient, having the desirable broad scope and reduced invasive requirements. There is also no prior recognition of fabricating the root-shaped custom portions of the prosthesis based on anatomical imaging data prior to the extraction of the tooth or of the teeth of interest or directly of the alveolar situation.

In addition, the inventors disclose the use of advanced ceramic materials, manufacturing technologies to increase the density of ceramic materials to its theoretical degree to be considered fracture-safe for use as dental implants or prostheses, metal-ceramic diffusion bonding technologies to overcome bacterial issues developing on the sub-gingival joints of traditional 3-part implant designs, and tissue engineering methods for osseo-integration and perio-type integration to enhance the clinical integration of prostheses designed and manufactured according to the inventions disclosed herein as further advantageous embodiments not previously recognized until now.

The product, and related systems and methods provided by embodiments of the present invention or inventions comprise several independent inventive features providing substantial improvements to prior art. The greatest benefit will be achieved for dental treatments—especially for patients requiring tooth replacement.

SUMMARY OF THE INVENTION

In view of the foregoing, various embodiments of the present invention beneficially provide customized dental prosthesis and implants based on a process or processes that include copying a significant portion of the original root geometry of a human tooth, to be integrated after extraction of the original tooth either in the existing biological cell structure of the periodontal ligament or as one piece into the embedding bone structure of the respective jaw. In an embodiment, primary stability is favorably achieved by a custom made splint that connects the prosthesis with the adjacent tooth or teeth or other dental structures like existing implants, bridges and the like. According to various embodiments of the present invention, an artificial root of the prosthesis or implant can be osseointegrated—embedded into the natural extraction cavity. According to various embodiments of the present invention, the principle of the natural mechanism of holding the teeth in the jaw structure of a dental patient is maintained and preserved, whereby a customized dental prosthesis is integrated into, healed in, and at least partially adopted by the fibrous connective tissue interface of the anatomical structure of an individual patient that is naturally holding the tooth.

The concept of periodontal integration of an artificial tooth uses the existing human periodontal ligament for integration and is certainly less invasive than the integration of osseointegrated implants. The concept of integrating a one-piece prosthesis that includes a root-shape part, an abutment and a crown combines the two clinical episodes of integrating the root-shaped part and adapting the crown into one clinical event. Even if such one-piece prosthesis would include an assembly of two or more parts, the assembly would be fabricated in the controlled environment of a dental laboratory or an industrial fabrication. As a result, the quality of the interface sealing between such parts can be expected to be of higher quality as produced in the mouth of the patient. This would reduce the infection rate so that the success rate of the one-piece prosthesis according to an embodiment of the invention would be higher as achieved with implementations according to the prior art. The concept of a splint that is custom made in the laboratory in advance serves two purposes: the correct positioning of the prosthesis, and the achievement of reasonable primary stability. The concept of using in-vivo imaging data in order to design and fabricate the prosthesis prior to the extraction of the teeth of interest enables a laboratory lead time prior to the invasive clinical event. The concept of using data to design a root-shaped portion or portions of the prosthesis not actually of the tooth or teeth extracted or to be extracted, but of the anatomical alveolar structure, allows the prosthesis to adapt to the post-extraction or even post-surgical—in case of, for example, surgical extensions to the extraction socket—shape of the alveolar situation.

Any combination of the aforementioned concepts of the invention can be used in embodiments of efficient and/or less-invasive clinical methods according to the invention. One of such clinical methods, for example, includes the immediate placement of a one-piece prosthesis—allowing immediate loading. In another embodiment, these concepts can be combined with methods of ultrasonic or other vibrations applied to the prosthesis or adjacent tooth/teeth after placement in order stimulate bone and tissue healing. In another embodiment, the extraction of the tooth might be performed using ultrasonic or other vibrations applied to the tooth of interest to facilitate the extraction.

All such methods can be also favorably combined with laboratory methods according to the invention. One of such laboratory methods might be the coating of the root portion of the prosthesis with engineered tissue that is grown in the laboratory from autologous tissue, bone or root material samples of the patient of interest. Alternatively to the aforementioned use of autologous material, human allogenic bone, root or tissue material can be used. Alternatively to the use of human bio material, tooth, bone or tissue material of animals, for example, bovine or even synthetic materials can be used for the process step of tissue engineering. Tissue engineering includes the use of a combination of cells, engineering materials, and suitable biochemical factors to improve or replace biological functions. In the context of certain embodiments of the invention disclosed herein, this would include the growth of soft tissue or bone structures in a controlled laboratory environment.

The term regenerative medicine is often used synonymously with tissue engineering, although those involved in regenerative medicine place more emphasis on the use of stem cells to produce tissues. This is an additional approach that can be favorably combined with other specific embodiments of the invention disclosed herein.

The various embodiments of this invention described herein are not only substitutive but additive to the available options in the field of restorative and prosthetic dentistry with the result that in most cases the need to use removable dentures will be significantly postponed.

In this context, embodiments of the invention described herein relate to fabricating customized segments of the dentition, single teeth, roots and crowns or parts of those. The artificial reproduction of the original root will be inserted into the alveolus, the natural cavity of the root of the tooth to be replaced. It will either be adopted by the periodontal ligament of the patient or osseointegrated if the periodontal ligament is no longer functional. The shape of the root can be a substantial copy of the root to be replaced or may be intentionally smaller, for example, to compensate for measurement or manufacturing tolerances or inaccuracies. The shape of such roots may alternatively be a direct copy of the root to be replaced, or it may be directly adapted to the alveolar situation, or any combination thereof. In certain cases it is advantageous to modify the shape to be integrated. For instance, it may be appropriate to conjoin the two or three roots of a molar to gain additional stability or enable the manufacturing of such. Also, strongly bent root tips may be reduced or left away in order to ease the insertion of the prosthesis. In cases of root resorption, it may be appropriate to re-establish a shape close to the estimated shape of the original shape of the root before the resorption clinically occurred. Even imaging data of an earlier clinical situation or imaging data of mirrored or un-mirrored data of the same or a similar shaped root of the same or the other (right-to-left, left-to-right) side of the jaw or of an opponent jaw of the patient may be favorably used in this context. It may be additionally possible to consider and use generic (averaged) root shapes in the process designing the target shape of the prosthesis. The extraction socket may be enlarged to accommodate for a bigger or different root shape compared to the extracted root shape.

Various embodiments of the present invention avoid or postpone the need of or for conventional heavily invasive implants for a significant time by using at first the natural periodontal structure as long as possible and afterwards by customized osseointegrated artificial roots or teeth. No such approach in dentistry based on design and manufacture of customized teeth including the root, or only roots suitable to be used in conjunction with off-the-shelf or customized components (typically for the visible part like veneers or complete crowns) used in the field of implantology for an individual patient, and design and manufacture of such customized tooth, has been proposed to date. The implants widely used in dental treatment today are off-the-shelf products. Because teeth have to fit properly for comfort and healing after surgery in the periodontal ligament of a patient, some commonly used implants do not constitute an optimal replacement.

The shape design of mass-produced implants shows a standardized joint between the implant and the crown portion. While the crown is usually custom-shaped to the adjacent and opposite teeth, the implant is not Therefore, the joint between such traditional crowns and implants is non-customized. Such joints are usually shaped with standardized cylindrical, hexagonal, and conical shape portions. In order to try to obtain a positive lock between the implant and the crown, numerous standard form joints are manufactured in order to try to cover a majority of the possible crown designs. This, however, results in significant additional manufacturing costs and difficulties in inventory management. Alternatively, a smaller number of "standard" designs are manufactured designed to cover most cases. Although the smaller number helps reduce inventory management problems and manufacturing costs, it has been found too often to lead to inadequate joint connections and in an increased number of collisions between components, as the clinician is often provided an improperly fitting connection. That is, the joint having a smaller footprint than ideal is often employed in order to allow for adjustments due to the inadequate connection. Recognized, therefore, by the inventors is the need for a custom joint which can provide a good positive lock between the implant and the crown/intermediate abutment, and which can maximize the "footprint" between the connecting pieces.

Accordingly, various embodiments of the present invention provide dental implant apparatus and methods of manufacturing or otherwise providing a custom prosthesis interface having a three-dimensional surface shape positioned and formed to create a form locking fit with respect to the crown/abutment and the implant body, which can maximize or at least significantly increase the footprint of the locking fit, which can reduce and/or eliminate collisions between manufactured components, and which allows individualized stocking—eliminating the need to manufacture multiple potential versions of the joint.

For example, various embodiments to the present invention include methods of manufacturing a dental implant to replace a non-functional natural tooth positioned in a jawbone of a specific pre-identified patient. An example of such a method can include the steps of receiving data describing a three-dimensional X-ray image of at least portions of the patient's dentition defining x-ray image data, and receiving data describing one of the following: a physical impression of a dental anatomy and a surface scan of the dental anatomy, defining impression image data made prior to removal of the non-functional natural tooth from the jawbone of the specific patient. The steps can also include forming at least one three-dimensional virtual model of at least portions of the non-functional natural tooth to include combining the x-ray image data and impression image data, and forming the at least one three-dimensional virtual model of the non-functional natural tooth including a modeled virtual root portion and a modeled virtual crown portion responsive to the x-ray image data and the impression image data.

The steps can also include designing a dental implant based upon the at least one virtual model of at least portions of the non-functional natural tooth. The step of designing the dental implant includes the steps of forming a virtual dental implant body modeling a dental implant body having a virtual prosthesis interface modeling a prosthesis interface of the dental implant body to receive an occlusally-facing dental prosthesis component. The step of forming a virtual dental implant body can include forming the virtual prosthesis interface to have a three-dimensionally contoured implant body surface shape at least partially correlated to a surface shape of an occlusally-facing surface of the modeled virtual crown portion.

According to a two-piece dental implant body configuration, the step of forming a virtual dental implant body includes separating a portion of the at least one three-dimensional virtual model (including the modeled virtual root portion and modeled virtual crown portion) along a virtual outer gum line representation. Beneficially, cutting along the gum line representation can have the effect of shaping an outward-facing circumferential edge of a virtual prosthesis interface of the virtual dental implant body to substantially match a shape of a corresponding outer gum line surrounding the non-functional natural tooth prior to removal of the non-functional natural tooth from the jawbone of the specific pre-identified patient.

The step of forming the virtual dental implant body can also include copying at least portions of the modeled virtual crown portion to form a base shape of the virtual prosthesis interface, reducing dimensions of the at least portions of the modeled virtual crown portion to define a virtual prosthesis interface model, and combining the virtual prosthesis interface model with the virtual root body portion model to form the virtual dental implant body.

According to this configuration, the steps can also include forming a virtual occlusally-facing dental prosthesis component modeling an occlusally-facing dental prosthesis component, such as, for example, a virtual crown component. According to such configuration, the step of forming the virtual crown component includes forming a complementing virtual dental implant body-receiving surface to define a complementing virtual interface surface modeling a complementing interface surface to receive occlusally-facing portions of the dental implant body, such that the prosthesis interface and the complementing interface surface create a form locking fit therebetween. This can be accomplished by copying at least portions of the modeled virtual crown portion to form a base shape of the complementing interface surface of the virtual crown portion, reducing dimensions of the at least portions of the modeled virtual crown portion, and combining the virtual crown portion model with the complementing interface surface model to form the virtual crown portion.

According to a three-piece dental implant body configuration, the step of forming a virtual dental implant body includes separating a portion of the at least one three-dimensional virtual model (including the modeled virtual root portion) along a virtual bone-facing gum line representation (e.g., effectively shaping the outward-facing circumferential edge of the prosthesis interface), copying at least portions of the modeled virtual crown portion to form a base shape of the prosthesis interface, reducing dimensions of the at least portions of the modeled virtual crown portion to define a prosthesis interface model, and combining the virtual prosthesis interface model with the virtual root body portion model to form the virtual dental implant body.

According to this configuration, the steps can also include forming a virtual occlusally-facing dental prosthesis component modeling an occlusally-facing dental prosthesis component, such as, for example, a virtual crown component and/or a virtual transgingival cap component. The virtual crown component can be formed by employing the procedures described with respect to forming the virtual crown component in the two-piece configuration, to include copying at least portions of the modeled virtual crown portion to form a base shape of a complementing interface surface of the virtual crown portion, reducing dimensions of the at least portions of the modeled virtual crown portion, and combining the virtual virtual crown portion model with the complementing interface surface model to form the virtual crown portion.

According to this configuration, the transgingival cap can be formed using a similar set of procedures. For example, the step of forming the transgingival cap component can include forming a complementing virtual dental implant body-receiving surface to define a complementing virtual interface surface modeling a complementing interface surface to receive occlusally-facing portions of the dental implant body. This can be accomplished by copying at least portions of the modeled virtual crown portion cut along the bone-facing gum line representation to form a base shape of the complementing interface surface of the transgingival cap portion, reducing dimensions of the at least portions of the modeled transgingival cap portion, and combining the virtual transgingival cap model with the complementing interface surface model to form the virtual transgingival cap.

According to various embodiments of a method of manufacturing a dental implant, the steps of receiving data, separating the portion of the at least one three-dimensional virtual model along the virtual outer/inner gum line representation, copying at least portions of the modeled virtual crown portion, reducing dimensions of the at least portions of the modeled virtual crown portion, and combining the virtual prosthesis interface model with the virtual root body portion model to form the virtual dental implant body, and the steps of forming the virtual occlusally-facing dental prosthesis component(s), in both the two-piece and three-piece configuration can be performed on a graphical user interface operably coupled to a computer responsive to user manipulation of an input device.

Further, the computer can produce a set of digital data virtually defining the three-dimensionally contoured implant body surface shape, which can be utilized by a manufacturing apparatus. As such, the design and manufacturing/fabricating steps can also include employing a machine process performed by a computer numerical control (CNC) based machining apparatus to form substantial portions of the dental implant body including the prosthesis interface responsive to the set of digital data, and/or employing a rapid prototyping process performed by a computer numerical control (CNC) based rapid prototyping apparatus to form substantial portions of the dental implant body including the prosthesis interface responsive to the set of digital data.

The machine process employed to fabricate the dental implant can include shaping the outward-facing circumferential edge of the prosthesis interface of the dental implant to substantially match a shape of the corresponding outer gum line surrounding the dental implant described in the received data for the two-piece dental implant design, and shaping the outward-facing circumferential edge of the prosthesis interface of the dental implant to substantially match a shape of the corresponding bone-facing gum line for the three-piece dental implant design. The shaping process can also include shaping the prosthesis interface to have the three-dimensionally contoured surface shape at least partially correlated to a surface shape of an occlusally-facing surface of the crown of the nonfunctional tooth to thereby create the form locking fit with the complementing interface surface of the occlusally-facing dental prosthesis component when positioned therein, and shaping the complementing interface surface of the occlusally-facing dental prosthesis component to have a three-dimensionally contoured surface shape substantially dimensionally matching the three-dimensionally contoured surface shape of the prosthesis interface to thereby create/enhance the form locking fit therebetween.

The three-dimensionally contoured implant body surface shape of the prosthesis interface can be formed to include a substantial asymmetric positive raising extending from the dental implant body. Such a shaping process can include shaping the substantial asymmetric positive raising to have a first rising contour extending from portions of the occlusally-facing surface of the root body portion adjacent a center of the lingual-facing side portion and a second rising contour extending from portions of the occlusally-facing surface of the root body portion adjacent a center of the labial-facing side, with the second rising contour being substantially different than the first raising contour when viewed along a cross-section of the dental implant extending between the lingual-facing side portion and labial-facing side portion and vice versa.

The shaping process can further include shaping an outer surface of the root body portion of the dental implant body to have a custom three-dimensional surface shape approximately dimensionally matching a three-dimensional inner-surface shape of corresponding surface portions of one or more intra jawbone anatomical features associated with the non-functional natural tooth of the specific pre-identified patient. Also or alternatively, the outer surface shape of the dental implant body can be shaped to match a three-dimensional outer surface shape of the root portion of the non-functional natural tooth of the specific pre-identified patient, a three-dimensional inner surface shape of a bone socket for the root portion of the non-functional natural tooth of the specific pre-identified patient, and/or a combination of the three-dimensional outer surface shape of the root portion and three-dimensional inner surface shape of the bone socket for the root portion of nonfunctional natural tooth of the jawbone of the specific pre-identified patient.

According to an embodiment of the process related to the three-piece design, the root body section of the implant is made of a titanium or other bone friendly material and the transgingival cap and crown portion are made of a ceramic material. In such configuration, implementation of the dental implant is generally performed by connecting the dental implant body with the transgingival cap at the prosthesis interface, normally prior to insertion of the root body section into the jawbone of the specific pre-identified patient. In such application, the transgingival cap is generally designed and fabricated so that when connected to the dental implant body and when the root body section is inserted into the jawbone of the patient, the outward-facing circumferential edge of the prosthesis interface is substantially below an outer gum line of the specific pre-identified patient surrounding lingual-facing, labial-facing, and proximal-facing surfaces of the non-functional natural tooth as determined prior to extraction thereof from the jawbone of the patient. Such configuration enhances osseointegration between the titanium root portion and the surrounding jawbone, with the gum being in contact with the ceramic portions.

In an embodiment of the present invention, a dental prosthesis is assembled as a one-part ceramic implant body with a translucent glass-ceramic cap. To achieve a qualitatively high one-piece dental implant, the white body of the root portion body is finished in a hot isostatic pressing process. Hot isostatic pressing (HIP) describes compression of materials to almost its theoretical density, by applying high temperatures and high pressure to the work piece of interest, i.e., the prosthesis or parts thereof. Therefore, firstly, the ceramic implant is covered with a customized metallic coating, or sintered to a density that the gas used for the later process step of hot isostatic pressing cannot transpire or migrate into the object to be pressed. In a further step, the coated or tightly sintered implant is placed in an oven with a temperature closely under the melting point of the ceramic material of the dental implant. Furthermore, an increased pressure is applied to the coated implant, thereby eliminating certain defects and flaws. After this process step (often called hot isostatic pressing), the coating is removed from the body by e.g., an etching process. The removal of the coating from the ceramic body can also be achieved by mechanic means. In an alternative embodiment, the ceramic implant is sintered in a first process step form its porous structure to be dense to a degree that the gas media of the following hot isostatic pressing process cannot invade into the material itself, so that the compressing, and therefore the elimination of internal defects, can take place.

In a further embodiment, the implant body is made of two or more different materials being assembled and connected by a soldering process and/or by diffusion bonding. Diffusion bonding may include technologies connecting different materials on an atomic level without a facilitating third material. Diffusion bonding may be facilitated by hot isostatic pressing to provide the required connection of the adjacent materials to the degree where diffusion bonding takes place.

In another embodiment of the present invention, the dental prosthesis provides a porous outer surface of the root body portion. Such a porous surface acts as a biocompatible and cell pleasing environment. Thereby, the process of osseointegration of the dental prosthesis into the jaw bone or the process of integration into the periodontal ligament is promoted. The porous outer surface can be achieved by, e.g., applying ultra-short laser pulses onto the surface eroding the material without a remnant of scoria or thermally altered adjacent surface material. Ultra short means time pulses having a length in time measured in the range of 1 to 1000 pico-seconds or 1 to 999 femto-seconds. Alternatively, the porous coating can be achieved by milling the outer surface of the root body portion. Moreover, the porous outer surface can be achieved by covering the outer surface of the root body portion with a ceramic porous coating which is applied or assembled in a customized and well controllable process.

In another embodiment of the present invention, the prosthesis comprises a customized form with an upwardly directed convex surface in the area between the roots of the prosthesis. Such a form prevents air inclusions from being enclosed in the area between the roots of the prosthesis.

In a further embodiment of the present invention, the one-part implant and the cap are separated by a customized joint. This customized joint is embodied as a three-dimensional surface comprising a form that is individually fitted to the design of the prosthesis and the course of the patient's gingival.

In another embodiment of the present invention, the overall fabrication is simplified. In this method, firstly, an impression is made of the patient's tooth. Moreover, a scan is obtained from a computed tomography device. Both types of data are combined and CNC-instructions (CNC: Computerized Numerical Control) are generated for the fabrication of the milling of the prosthesis and the dedicated splint. As another enhancement of the present invention, the overall fabrication process can partly or totally be executed at the chair side of the dentist executing the treatment of the patient.

In yet another embodiment of the present invention, the surface data obtained from the impression of the tooth and the surface data obtained from the computed tomography device are combined utilizing statistical methods.

According to various embodiments of the present invention, the manufactured includes a dental implant body having a prosthesis interface formed therein to receive an occlusally-facing dental prosthesis component. The prosthesis interface has a three-dimensional, e.g., asymmetrically contoured, surface shape positioned and formed to create a form locking fit with respect to the occlusally-facing dental prosthesis component when positioned thereon. The prosthesis interface also has an asymmetrically contoured outward facing edge having a shape correlated to a shape of a gum line of the specific pre-identified patient. The three-dimensional surface shape of the prosthesis interface is also substantially asymmetrically shaped and substantially devoid of concentric convolutionally shaped segments with respect to a longitudinally extending axis of the dental implant.

According to this exemplary configuration, the dental implant body includes a root body portion having an occlusally-facing surface, a lingual-facing side portion, a labial-facing side portion, and a pair of proximal-facing side portions. The three-dimensional surface shape of the prosthesis interface includes a substantial asymmetric positive raising extending from the dental implant body. The asymmetric positive rising has a first rising contour extending from portions of the occlusal facing surface of the root body portion adjacent a center of the lingual-facing side portion and a second rising contour extending from portions of the occlusal facing surface of the root body portion adjacent a center of the labial-facing side, with the second rising contour being substantially different than the first raising contour when viewed along a cross-section of the dental implant extending between the lingual-facing side portion and labial-facing side portion and visa versa.

According to another embodiment of the present invention, the dental implant can include a dental implant body having a prosthesis interface having a three-dimensional surface shape positioned and formed to create a form locking fit with respect to the occlusally-facing dental prosthesis component when positioned thereon, whereby the prosthesis interface also has an asymmetrically contoured outward facing edge extending along labial-facing, lingual-facing, and first and second proximal-facing portions of the dental implant body. According to this exemplary configuration, the asymmetrically contoured outward facing edge follows a gum line of the specific pre-identified patient surrounding the dental implant body when the dental implant body is operably positioned within the jaw bone of the pre-identified patient. The outward facing edge can be configured such that each of a plurality of spaced apart points located along an extent of a proximal-facing portion of the asymmetrically contoured circumferential outward facing edge asymmetrically vary in axial distance from a common reference point located along a longitudinally extending axis of the dental implant body. According to this exemplary configuration, each of the plurality of spaced apart points located along the extent of the proximal-facing portion of the asymmetrically contoured circumferential outward facing edge asymmetrically vary in both radial distance from the common reference point located along the longitudinally extending axis of the dental implant body and in the axial distance from the common reference point. Similar asymmetric variations can exist on the lingual and labial-facing portions.

According to another embodiment of the present invention, the dental implant can include a dental implant body having a prosthesis interface formed therein to receive an occlusally-facing dental prosthesis component and to create a form locking fit with respect to the occlusally-facing dental prosthesis component when positioned thereon. According to the exemplary configuration, the three-dimensional surface shape of the prosthesis interface is correlated to a three-dimensional surface shape of an occlusally-facing surface of the occlusally-facing dental prosthesis component. Additionally, the three-dimensional surface shape of the prosthesis interface is devoid of concentric convolutionally shaped segments with respect to a longitudinally extending axis of the dental implant body, substantially rotationally symmetrically shaped segments with respect to the longitudinally extending axis of the dental implant body, substantially symmetrically shaped segments with respect to the longitudinally extending axis of the dental implant body, substantially symmetrically shaped segments with respect to a point adjacent to the longitudinally extending axis of the dental implant body, and substantially symmetrically shaped segments with respect to a plane substantially parallel to the longitudinally extending axis of the dental implant body. Further, according to the exemplary configuration, the prosthesis interface can have an asymmetrically contoured outward facing edge substantially matching labial, lingual, and first and second proximal portions of a gum line of the specific pre-identified patient when the dental implant body is operably positioned within the jaw bone of the pre-identified patient.

According to another embodiment of the present invention, the dental implant body includes a prosthesis interface having a substantially non-planar surface shape correlated to a surface shape of an occlusally-facing surface of the occlusally-facing dental prosthesis component, and having an outward facing circumferential edge having in its dimensional extension at least four substantial extrema in a direction of the longitudinally extending axis of the dental implant body. The dental implant body also includes a transverse-section that when taken perpendicular to the longitudinally extending axis and adjacent to the prosthesis interface has a first dimension in a first direction and a second dimension in a second direction such that the first dimension is substantially bigger than the second dimension.

According to this exemplary configuration, a center portion of the prosthesis interface is substantially raised in a direction of the longitudinally extending axis over the outward facing circumferential edge to create a male portion of a form locking fit with respect to the occlusally-facing dental prosthesis component when positioned thereon. Alternatively, a center portion of the prosthesis interface is substantially indented in a direction of the longitudinally extending axis over the outward facing circumferential edge to create a female portion of a form locking fit with respect to the occlusally-facing dental prosthesis component when positioned thereon. According to this exemplary configuration, a shape of the outward facing circumferential edge can substantially match either a shape of a corresponding outer gum line surrounding the dental implant body or a shape of a corresponding bone crest line surrounding the dental implant body when the dental implant is operably positioned within the jaw bone of the pre-identified patient.

A further embodiment of the present invention relates to the wet delivery process of the presented dental prosthesis. In the first step, the prosthesis is placed in an open container which is filled with an isotonic liquid, thereby coating the whole body of dental implant. Then ultraviolet electromagnetic radiation is applied onto the prosthesis to enhance the biocompatibility of the outer surface. In another step the container is closed, placed in a high temperature oven and loaded with a high external pressure. The pressure keeps the container from breaking during the increase of temperature up to values at which the liquid would start to boil (under normal pressure circumstances). By this step, a sterilization process is applied on the prosthesis which leaves the prosthesis in its moisturized environment and, thereby, keeps the biocompatibility of the outer surface active.

Directly after placement, the prosthesis may be tied, glued or otherwise fixated for several weeks to adjacent original or artificial teeth or tentative implants like mini-screws likewise with the custom splint according to the invention. In an embodiment of the present invention, a splint is provided which comprises recesses formed as holes. These holes enhance the adhesive in attaching the splint to the prosthesis and its adjacent teeth. In a further embodiment of the present invention, the aforementioned splint which is attached only to one of the adjacent teeth. This splint can be used in cases where only one of the adjacent teeth is capable of providing primary stability to the prosthesis via the splint. If the other adjacent tooth is not qualified for a splint to be attached, this splint design can be utilized.

For a situation in which the directly adjacent teeth of the prosthesis are both not capable for a splint to be attached to, a splint is proposed which attaches to the teeth next to the adjacent teeth. This specifies a possibility for providing primary stability to the prosthesis by utilizing the teeth next to the adjacent teeth. Such a splint can be on particular importance if the directly adjacent teeth are not capable of providing sufficient primary stability.

As an exemplary embodiment of the present invention, the crown portion of the aforementioned prosthesis forms one part with the aforementioned splint. I.e., the crown comprises wings reaching to the adjacent teeth in a way that the wings can be attached to the adjacent teeth of the prosthesis. In a further embodiment of this crown with splint wings, the crown portion is attached to the one-part implant by utilizing a screw. Thereby, the crown portion with the splint wings can be removed when the implant is fully integrated in the alveole. After removing the crown portion with splint, a final cap can be placed on the one-part implant.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 6 shows an artificial tooth having a root portion and a crown portion, the portions representing the root being coated in order to promote periodontal integration.

FIG. 7 is a view of an artificial tooth being made from a material promoting periodontal integration, the crown being coated with another material having optimized esthetic and/or mechanical properties.

FIG. 8 shows an artificial tooth, the portion representing the crown being made from a material having optimized esthetic and/or mechanical properties, while the portion representing the root is made from a material promoting periodontal integration.

FIG. 9 is a view of an artificial tooth being made from a material having optimized esthetic and/or mechanical properties, the portions representing the root being coated in order to promote periodontal integration.

FIG. 32 shows an arbitrary portion of an STL file in ACSII format.

FIG. 33 shows an arbitrary portion of an IGES file in ACSII format.

FIG. 34 shows an implanted artificial tooth, the voids between the root portion and the extraction socket filled with a bone promoting substance.

FIG. 35 is a cross-sectional view of the components of a segmented artificial tooth, the segment representing the root being expandable by being slotted and having a conical thread.

FIG. 36 is the artificial tooth of FIG. 35 inserted into the extraction socket and being expanded by inserting screw into the conical thread.

FIG. 37 is a known two-part implant for osseointegration.

FIG. 38 is a known three-part implant for osseointegration.

FIG. 48 shows the process steps of clinically preparing an extraction socket with a laser technology based device.

FIG. 80 illustrates the combining of virtual models to form a virtual crown portion.

FIG. 81 illustrates the combining of virtual models to form a virtual dental implant body.

FIG. 82 illustrates the attachment of a crown portion of a dental implant to a dental implant body to form the dental implant.

FIG. 85 illustrates the combining of virtual models to form a virtual dental implant body portion.

FIG. 86 illustrates the combining of virtual models to form a virtual transgingival cap portion.

FIG. 87 illustrates the combining of virtual models to form a virtual crown portion.

FIG. 88 illustrates the attachment of a transgingival cap portion of a dental implant to a dental implant body and attachment of a crown portion to the transgingival cap portion to form the dental implant.

FIG. 89 illustrates a completed three-piece dental implant.

DETAILED DESCRIPTION

The present invention will now be described more fully hereinafter with reference to the accompanying drawings, which illustrate embodiments of the invention. The invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Figure 1:
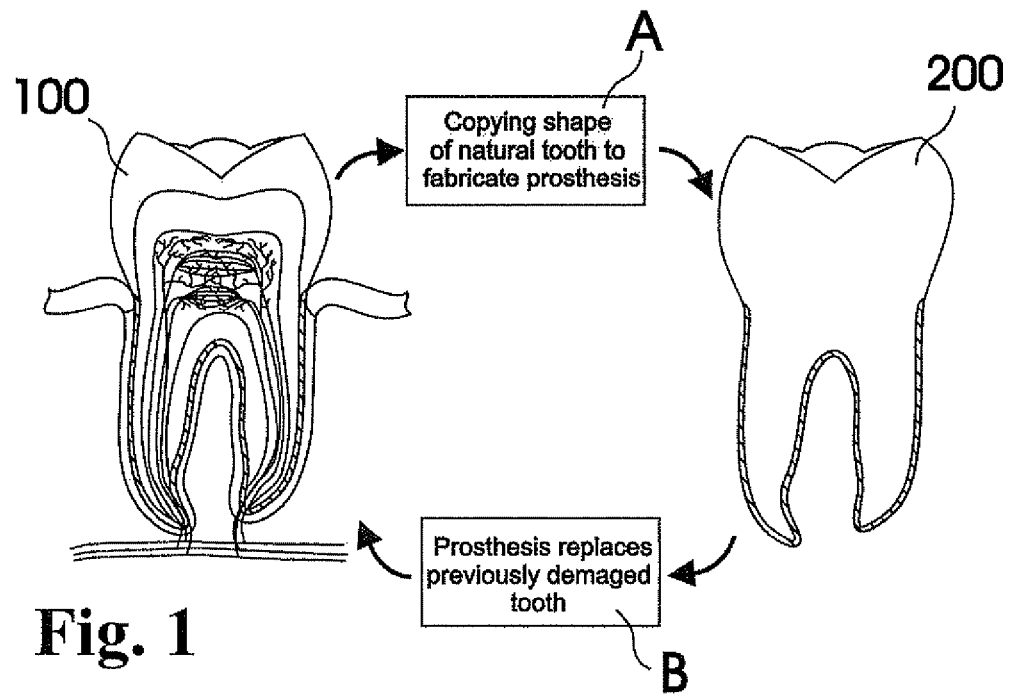
FIG. 1 shows a procedure of replacing a human tooth with a prosthesis in accordance with an aspect of the invention.
Figure 28:
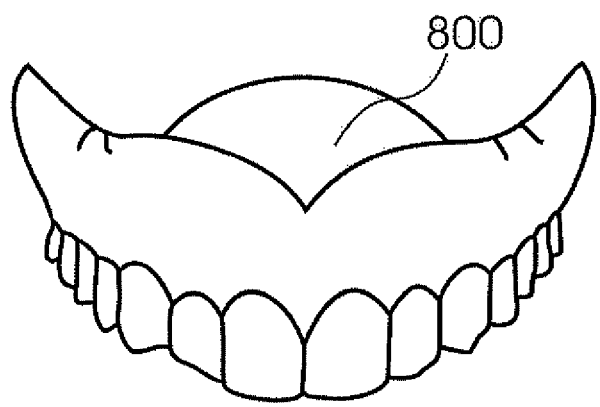
FIG. 28 shows a removable denture according to prior art.

Current methods for replacing damaged teeth have several disadvantages. For example, conventional bridge implants require healthy teeth to be ground, and osseointegrated implants are drastically invasive. Additionally, these prostheses have a limited average lifetime. Removable dentures (800) as shown in FIG. 28 are certainly the final prosthetic option. An object of the invention is to design and manufacture customized dental prosthesis for replacing human teeth. FIG. 1 illustrates a method of replacing a human tooth with a customized dental prosthesis according to an embodiment of the invention. First, in step (A) a copy (200) of the natural tooth (100) to be replaced is fabricated. Then, in step (B) the natural tooth (100) is replaced with the prosthesis (200).

Figure 2:
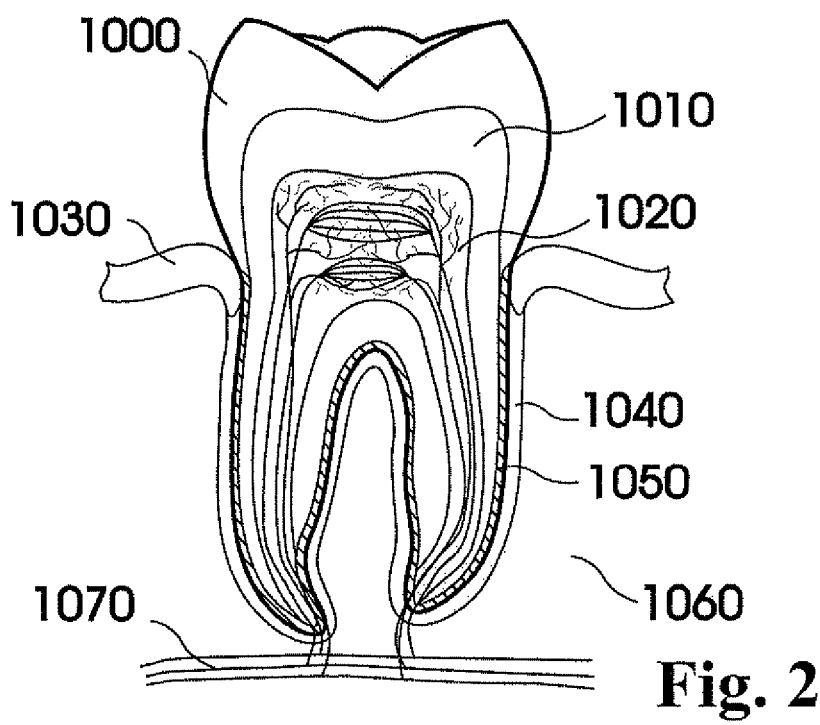
FIG. 2 is a detailed cross-sectional view of a natural tooth.

FIG. 2 shows a natural tooth embedded in its socket. The pulp (1020) holds nerves and blood vessels (1070). It is surrounded by dentine (1010), which is covered with enamel (1000). The root portions have a thin layer of cement (1050) providing connection to the ligament (1040), which serves to anchor the tooth to the bone (1060). The outside of the bone is covered with gum (1030).

Figure 26:
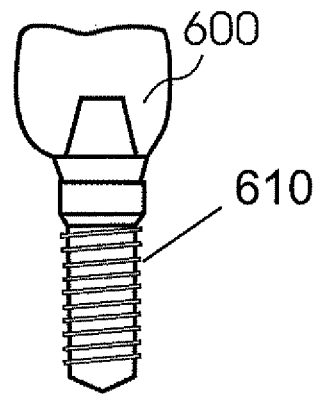
FIG. 26 shows a dental implant according to prior art.
Figure 27:
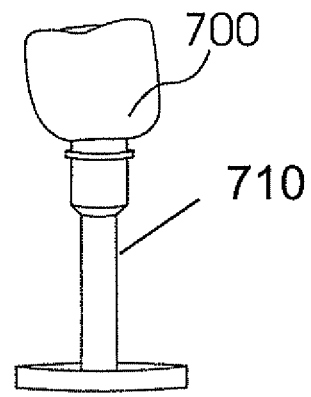
FIG. 27 shows another implant according to prior art.

FIGS. 26 and 27 show conventional implants. The implanted portion (610 and 710) is an off-the-shelf part to be inserted into a hole drilled into the jaw bone. The crown (600 and 700) is generally customized to the individual tooth it is replacing.

According to an embodiment of invention, a dental prosthesis is individually shaped and integrated into the natural extraction socket of an individual specifically identified patient. The shape of the portions of the prosthesis representing the root substantially copies the natural root of the tooth that was located in the socket. However, the shape may be modified in order better adapt to the natural socket or to ease insertion of the prosthesis. Also, the socket may be surgically adapted for the same reasons. For example, damaged and infected soft tissue, tooth or bone substances would not allow for immediate implantation. Then, a dental laser may be used to remove the damaged structures. The most commonly used dental lasers are diode, carbon dioxide, erbium YAG, erbium YSGG, Nd:YAG, and argon lasers. The applications for each wavelength depend on the absorptions of laser energy by different tissue types. The Erbium family can be used for caries removal, bone surgery, mucosal surgery and gum surgery. While other laser families are mainly used in soft tissues surgeries. Benefits in laser assisted dental treatment include decreased morbidity after surgery, hemostasis, and a reduction in the need for anesthetics in selected cases.

A Erbium laser, for example, emits light with a wavelength of 2940 nanometers, which is primarily absorbed by water. Decayed material has an extremely high water content so that the laser light energy evaporates the damage and is able to cut very precisely with little or no collateral damage depending on the settings used during the surgery. When used on hard tissues the Erbium laser energy that touches the hard tissue heats up the water within the hard tissue and causes that water to be turned into steam. That causes a mini-explosion to occur and the hard tissue is "ablated" (removed). Diode lasers in general use as an active medium, a semi-conductor P-N junction made in a GaAlAs crystal. A flexible fiber is used to transmit the laser energy to the surgical site.

According to an embodiment of the present invention, a segmented prosthesis can be used. A segmented, also referred to a segment, prosthesis is one in which a first segment is implanted into the extraction socket and second segment, for example, a portion representing the crown of a tooth, is attached to the segmented portion. Accordingly, segmented prosthesis include at least two separate portions which may be manufactured and implanted at separate times. The segment which is implanted into the extraction socket is a representation of the root of the natural tooth and can be manufactured based on 3D imaging data. The segment representing the crown can be manufactured according to standard procedures known in the art.

An embodiment of the present invention comprises the following steps: (i) Recording and digitizing (scanning) the three-dimensional anatomical shape of a human tooth or dentition; (ii) Obtaining a virtual model of the tooth as data record; and (iii) Manufacturing of the prosthesis, based on the three-dimensional data that have been obtained by the scan and if applicable, optimized.

The data may either be recorded intra-orally from the patient, such as with a 3D camera, a micro laser optical device, a computerized tomography apparatus, or an ultrasound apparatus, or be recorded extra-orally by scanning an extracted tooth. If required, the model can be modified in order to ease insertion or to receive aids for the final correct positioning of the fabricated prosthesis. The prosthesis can be directly produced by milling, grinding or rapid prototyping, for example, at a dentist's office or in a laboratory. It can also be produced using conventional laboratory procedures like casting. Preferably, the implant portion representing the root is manufactured using CAM methods, e.g., based on an acquired virtual model, while other portions of the prosthesis, for example, representing the crown or bridge, can be manufactured using standard procedures known in the art.

The process of milling or grinding dental crowns and inlays from ceramic material based on digital data was successfully introduced to dentistry approximately twenty years ago by SIEMENS (now Sirona, Bensheim, Germany) under the brand name CEREC. A modification of the SEREC system as would occur to one of ordinary skill of the use of suitable similar CAD/CAM and CNC design and manufacture as would occur to one of ordinary skill in the art, can be utilized. Although conventional prosthesis manufacturing systems, such as the CEREC system, are generally closed systems, one skilled in the art would readily appreciate these closed systems can be modified such that they may be readily integrated into the methods of the invention. Furthermore, certain embodiments of the invention disclosed herein relate to standard off-the-shelf CAD/CAM and CNC components that can be readily integrated into the disclosed methods Preferably, at least the customized implant portion of the dental prosthesis is fabricated using a CAD/CAM based method and system, wherein the three-dimensional shape of an extracted tooth is scanned and substantially copied, using a 3D scanner, multi-axes CNC machinery and biocompatible material or material later to be covered with a thin layer of biocompatible material that is suitable to be integrated into and adopted by the existing periodontal ligament cell structure of an individual patient.

Figure 5:
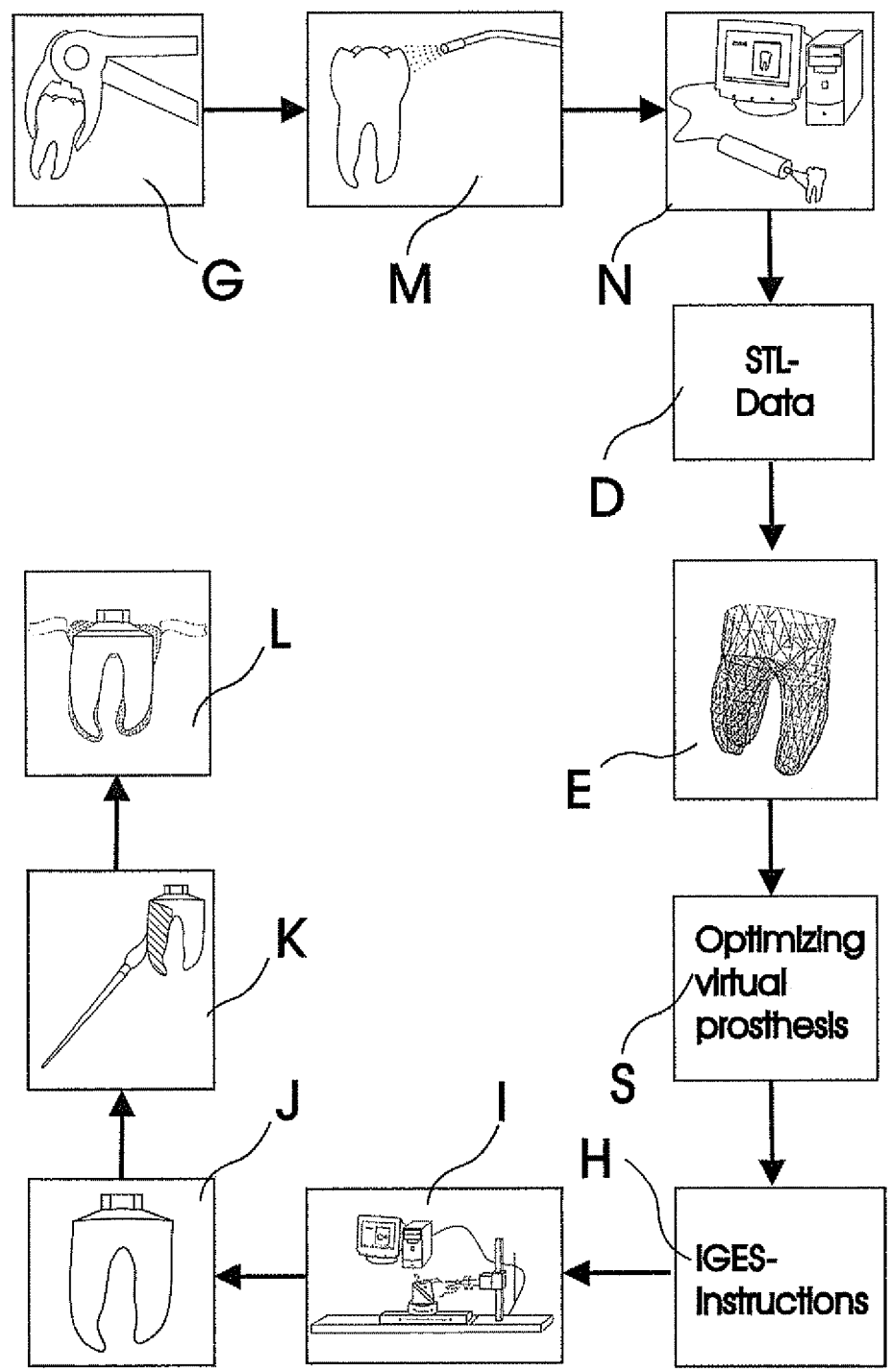
FIG. 5 shows the process steps of acquiring three-dimensional data of the root of an extracted human tooth, processing and completing the resulting 3D data with features for connecting an off-the-shelf abutment and inserting the prosthesis into the socket of the natural tooth according to an embodiment of the invention.

An overview of a method for replacing a tooth according to the invention is shown in FIG. 5. First, the tooth to be replaced is extracted (step G) and properly cleaned (step M). Then 3D imaging (step N) is performed in order to obtain 3D data (D) representing the three-dimensional shape of the root of the tooth. The resulting 3D data is imported into CAD software and displayed to an operator (step E). At this point, the 3D data may be modified, for example, to alter the shape of the root of the virtual model. It should be noted that although FIG. 5 contemplates possible interaction with an operator, one skilled in the art would readily appreciate that this functionality may be fully automated. Additional features may be added from a digital library and merged into the 3D root data (step S). The resulting 3D data is converted into JOBS format and exported (step H) to a CAM system for fabricating (step I) the prosthesis (J). The fabricated prosthesis is then coated with a substance promoting bone ingrowth (step K). It should be noted that coating the prosthesis is an optional step. The prosthesis is then implanted into the extraction socket (step L).

The tooth to be replaced, for instance, a lower left incisor (having an envelope volume of approximately 7 mm×8 mm.×23 mm) is extracted in a surgical environment, then disinfected and cleaned in a solution of hydrogen peroxide. The three-dimensional shape (scanning) of the extracted tooth may be obtained using, for example, a light-based scanner like ATOS II SO (gom GmbH, Braunschweig, Germany). In a first step, the root of the tooth is scanned. To achieve an optimal surface for optical scanning, the root is covered with a thin layer of $TiO_2$ powder (like CEREC powder from Sirona, Bensheim, Germany) that is applied with an atomizer using compressed air. Other coatings are also applicable that can for instance be applied by air-brush painting or a regular brush. For example, it is possible to "shake-up" $TiO_2$ powder in alcohol applying a uniform thin layer of $TiO_2$ by airbrushing generating this way high-precision data during scanning. A portion of the crown of the tooth is attached to the turntable of the scanner using a removable adhesive material (like for instance wax used in dental laboratories).

The turntable is then rotated in 15 degree increments step-by-step for a 360 degree view. The scanner scans at each of the 15 degree increments the optically accessible root surface of the tooth and is thus generating and exporting digital surface data representing the scanned portions of the three-dimensional shape of the surface of the root. The turntable is controlled by the software delivered with the scanner.

The digital surface data consists of multiple measurement data points each having an x, y, and z coordinate and together having a density better than 0.1 mm and an accuracy noise of less than 0.05 mm. Alternatively, other resolutions, accuracies, and coordinate systems including but not limited to cylindrical or spherical coordinate systems can be employed by those skilled in the art. The data points are exported in STL format. This widely used file format describes a surface or portions of a surface by interconnected triangles. STL files can be encoded either binary or in ASCII format. FIG. 32 shows an arbitrary example of a portion of such a file in the easily readable ASCII format.

Reference elements that are fixed to the turntable are additionally scanned at each increment. The ATOS II scanner software is able to detect such reference elements in the STL data of each incremental scan. Based on the reference elements it automatically transforms, superimposes and combines the incremental scans. The result is a comprehensive STL file describing the surface of the root of the tooth.

Other suitable imaging methods include but are not limited to CT, CBCT, MRT, ultra sound, destructive scanning, active triangulation, passive triangulation, confocal scanning, and TOF (Time-of-Flight). Such methods are generating either surface descriptions, for example, in STL-format or volumetric data for example, in a so called "voxel"-format that can be transformed into surface data by generally available software applications known to those skilled in the art, and vice versa.

Figure 29:
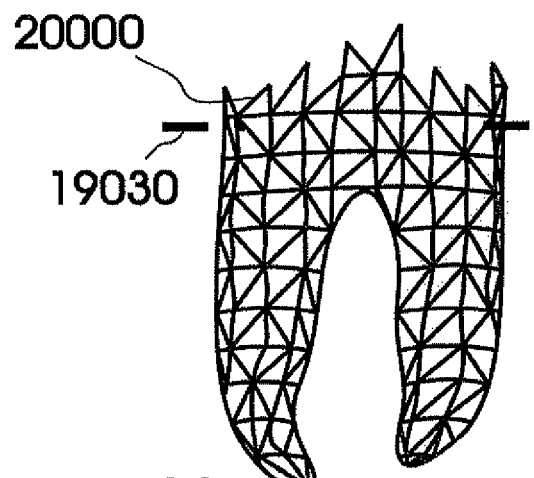
FIG. 29 shows 3D data resulting from the imaging of the root of a natural tooth.
Figure 30:
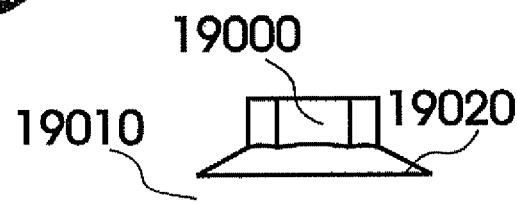
FIG. 30 shows the 3D data of FIG. 29, but cleanly cut at the top, and a virtual hexagon socket from an electronic library.

The scan of the root is then loaded into a CAD software application called MAGICS (Materialise, Leuven, Belgium). Using the cutting features of MAGICS, the occlusal facing edge of the virtual root model (FIG. 29, 20000), which will be uneven and "frayed" in the original scan data, will be straightened in order to receive a clean contour. A straight cut will be performed at a location (19030) where scan data is substantially complete. This is demonstrated in FIGS. 29 and 30. Then, from an electronic library, a virtual hexagon socket is selected and additionally loaded into MAGICS and placed on top of the virtual root, as shown in FIG. 30. Note, when terms like "top" and "bottom" are used in this context, it is always assumed the root tip points downwards. The hexagon socket consists of the hexagon shape (19000) fitting to the off-the-shelf abutment that will later be mounted to the artificial root, and a junction portion (19020) providing the transition to the virtual root. Since there is a significant variation in root thicknesses and shapes, a selection of hexagon sockets is available in the electronic library, each having a different junction portion in order to receive a minimal gap between the virtual root and the virtual socket.

In a next step, the so-called "stitching" functionality of MAGICS is used to close the gap (19010) between the virtual root and the virtual socket and, if applicable, also other gaps that may be a result of incomplete scanning. The outcome of this step is a virtual representation of a solid. In this context, a three-dimensional solid is an unambiguous numerical description of the surface of the geometrical shape of a three-dimensional object, the numerical description showing no holes and clearly identifying the inside and the outside of the surface.

Figure 31:
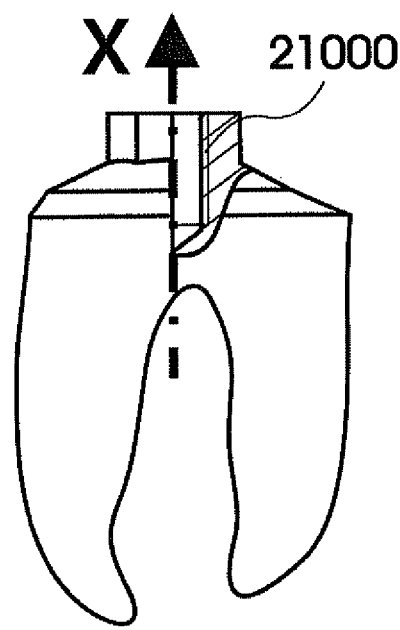
FIG. 31 shows a partial cross-section of an implant having a hexagon socket and a thread for attaching the abutment.

The hexagon socket of the actual prosthesis also needs to have an inside thread (FIG. 31, 21000) to receive the screw used for mounting the crown. In the illustrated embodiment, this thread is not part of the virtual model. Rather, the first step of manufacturing is to cut this thread into the workpiece used for fabricating the prosthesis, and then to use it to mount the workpiece to the machine table of the milling machine. To ensure spatial integrity, the coordinate system of the virtual solid must be placed properly. Preferably, the origin of the coordinate system will be placed in the center of the hexagon, one of the main axes running parallel to the midline of the thread as shown in FIG. 31.

The STL data describing the solid representing the tooth are then converted to an IGES data format. This is performed using, for example, a software named SolidWorks (Solid-Works Corp., Concord, Mass. USA). The IGES file allows generating a CNC sequence to machine an artificial tooth from a piece of biocompatible material like titanium or a titanium alloy (like $Ti_6Al_4V$), that consists, for example, of more than 60% of titanium. FIG. 33 shows an arbitrary example of a portion of such a file. Ceramic material and other biocompatible materials (including but not limited to stainless steel (like 1.4435, 1.4542 or 1.4548), synthetics, elastics, plastics, resin-modified glass-ionomer cement, hybrid-ionomer cement, resin-enforced cement, and other synthetic and plastic materials) are also applicable. For manufacturing the prosthesis for the above mentioned lower left incisor a workpiece having a size of 20 mm.×10 mm.×10 mm is adequate. For machining, a traditional 5-axis CNC milling device with a high-speed spindle is used. Other workpiece sizes and multi-axes CNC machining devices can be employed in this context by those skilled in the art.

After cutting the thread that will be located in the center of the hexagon of the finished prosthesis, the workpiece is screwed to an adapter on the machine table of the milling machine by using said thread. The adapter is either shaped so that it leaves sufficient clearance for the milling spindle and the cutter, or a disposable adapter is used so that portions of the adapter itself may be milled off. After teaching the machine the position and inclination of the workpiece, entering the machine and process parameters and overlapping the physical workpiece with the virtual shape, the root shape of the left lower incisor is machined by grinding the workpiece down layer-by-layer to the desired shape.

After manually cleaning, removing the excess, if applicable, polishing, degreasing, etching rinsing, disinfecting and drying the workpiece, it is ready for insertion. In order to improve the integration of the implant into the bone, further treatments according to the prior art, are possible. Sand-blasting with ceramic particles for instance creates a rough, and thus, significantly enlarged surface. Other porous-surfacing technologies can be used in this context too. Coating the surface with hydroxylapatite stimulates bone formation promoting a physico-chemical bond. Other coatings suitable to facilitate include but are not limited to pharmaceuticals, ancestral cells (e.g., multi-potent cells, fat-derived stem cells and other stem cells), and proteins. Instead of coating, the aforementioned substances can be applied by others means including but not limited to adjunction and injection.

Before inserting the prosthesis, the extraction socket will be properly scraped out or curetted and cleaned. In another embodiment, the socket will then be filled with Bioplant (Kerr Corporation, Orange, Calif.). Bioplant is a bone promoting substance. It is hydrated with marrow blood from the extraction socket and then injected into the socket using a special syringe delivered with Bioplant. Bioplant fills any voids present between the socket and the implant. After insertion of the implant, additional Bioplant may be applied in order to fully embed the implant below the hexagon socket. FIG. 34 shows the prosthesis embedded in the extraction socket, the voids being filled with Bioplant (13000). Alternatively, or in addition, bone demineralized matrix proteins, bone growth stimulating proteins, or other growth stimulating substances may be applied or otherwise used to facilitate the osseointegration and the building of the secondary stability of the prosthesis. The application of growth stimulating substances can be combined with antibiotic substances to avoid or suppress infection or inflammation. Drug releasing surfaces can be loaded with the aforementioned medical substances or any combination thereof releasing such substance(s) over a period of time. Growth stimulating substances can include or be derived from autologous, allogenic, or animal-derived cells or tissue. In order to avoid the growth of the gum into the void between the implant and the extraction socket, membrane techniques known to those skilled in the art can be employed. Also, the top of the implant excluding the hexagon has been covered with Bioplant. A healing cap is placed on top of the implant. The implant is then secured to the adjacent teeth for about six weeks by means of a light-curing resin strip known to those skilled in the art.

After the implant is healed in, standard procedures of prior art can be performed. After an alginate impression has been taken, a customized tray is fabricated, reinforced and perforated where the implant is located. An impression post is screwed onto the implant, and the customized tray is placed onto the dentition. The void between the perforation in the tray and the impression post is filled with impression putty. After the putty has set, the screw attaching the impression pin to the implant is unscrewed, and the impression is removed from the patient's dentition and sent to a specialized laboratory. Based on the impression and an impression of the opposing jaw, the technician will fabricate a crown. When the crown is delivered, the abutment is screwed to the implant, and the crown is cemented onto the abutment.

Another substance suitable to promote bone regeneration is CERASORB DENTAL (curasan AG, Kleinostheim, Germany). It consists mainly of pure phase beta-tricalcium phosphate (beta-TCP). CERASORB is completely resorbed and replaced by natural bone structure. Collagen fibers and blood vessels invade the interconnecting micro-pores of the CERASORB granules (micro-pores) and the inter-granular cavities (macro-pores). The primary-grain size of 10-63 µm does not provoke phagocytosis by macrophages.

Patent Application publication number 2005/0084513, which is hereby incorporated by reference in its entirety, discloses a coating for an implant surface. The coating promotes characteristics on the implant surface such as reducing protein unfolding, preventing inflammatory and fibrotic cell accumulation, reducing the number of such cell attachment sites and preventing other adverse biological reactions. The coating may be applied on any material via physical and/or chemical binding. It may also be used for in vitro purposes.

Another option is to apply nano-crystalline diamond coating. A coating named r-BeSt (Hartstoffbeschichtungs GmbH, Innsbruck, Austria) shows 100% biocompatibility due to the pureness of the diamond coating, an optimal interconnection between substrate and diamond coatings, good tribological properties due to the smoothness of the layer and an active surface for bio-chemical reactions. Another option is to apply inert coating with pyrolyt-carbon, which includes isotropic and non-isotropic structures.

In yet another embodiment sputter technologies are used to apply, for example, zircon-oxide surface on a custom-made titanium body to prepare adventurous surface features. For example, it is known that zirconium-oxide is tissue friendly. Sputter technologies include but not limited to ion sputtering, plasma sputtering and other sputtering technologies used under vacuum.

In another embodiment of the invention, an unsegmented prosthesis will be fabricated as shown in FIG. 9. The steps of the process are outlined in FIG. 4. The tooth to be replaced is extracted (step G) and properly cleaned (step M). Then 3D imaging (step N) is performed in order to obtain 3D data representing the three-dimensional shape of the complete tooth. The resulting 3D data (D) is imported into CAD software and displayed to the operator (step E). The shape is modified and optimized as needed (step F, see also FIGS. 23 and 24). The resulting 3D data is converted into IGES format and exported (step H) to a CAM system for fabrication of the prosthesis (step I). The finished prosthesis (J) may be coated with a substance promoting bone ingrowth (step K) and is then implanted into the extraction socket (step L). It should be noted that although FIG. 4 contemplates possibly interaction with an operator, one skilled in the art would readily appreciate that this functionality may be fully automated.

The prosthesis is preferably made from a material supporting osseointegration, such as, for example, porous calcium phosphate ceramic. This material provides a scaffold for bony ingrowth. In order to fabricate a complete prosthesis, the shape of the crown must also be available. Therefore, after the imaging of the root portion has been completed as described above with respect to FIG. 5, the crown is scanned. It will also be covered with $TiO_2$ powder. A portion of the root of the tooth is attached to the turntable of the scanner while the crown is optically exposed in order to be scanned in the same incremental manner. A second comprehensive STL file is accordingly generated describing the surface of the crown of the tooth. The scan of the root as well as the scan of the crown is performed in a way that a significant overlapping area of the surface of the counterpart is included in each scan.

The scan of the root and of the crown are then loaded into MAGICS and manually maneuvered to a best fit using the overlapping areas of both scans, and merged into one. STL data file. In order to increase accuracy, software detecting best fit for two independent surfaces can also be used. After manually removing outliers of the scanned measurement data and identifying and correcting deficient triangles and adding missing parts (if required), the resulting STL surface data forms a three-dimensional solid representing the overall shape of the extracted tooth.

The STL data is then converted to an IGES data format. For fabricating the above mentioned lower left incisor, a piece of calcium phosphate ceramic having a size of approximately 25 mm×10 mm×10 mm can be worked using a traditional 5-axis CNC milling device with a high-speed spindle (about 60.000 rpm), a spherical diamond cutter having a diameter of the tip of the cutter of 1 mm, and water cooling. The ceramic workpiece is clamped to the machine table of the milling machine. After teaching the machine the position and inclination of the workpiece, dialing in the machine and process parameters, and overlapping the physical workpiece with the virtual shape, a first portion representing the root shape of the lower left incisor is machined by grinding down layer-by-layer the workpiece to the shape of interest. Then, a fixture is made for that specific workpiece to clamp the workpiece at the already machined first portion, for instance by grinding a portion of the geometrical negative shape of the first portion into the receiving part of the fixture.

After teaching the machine position and inclination of the reoriented workpiece clamped into that customized fixture, entering machine and process parameters, and overlapping the physical second part of the workpiece with the virtual shape of the second portion to be machined, the crown shape of the left lower incisor is machined by grinding the workpiece down layer-by-layer to the desired shape. After properly cleaning, removing the excess, and degreasing, the prosthesis is ready for insertion into the extraction socket. After the implantation, the artificial tooth is fixed substantially to the same position and inclination of the extracted tooth by being bonded with light curing resin strip to the adjacent teeth.

Figure 17:
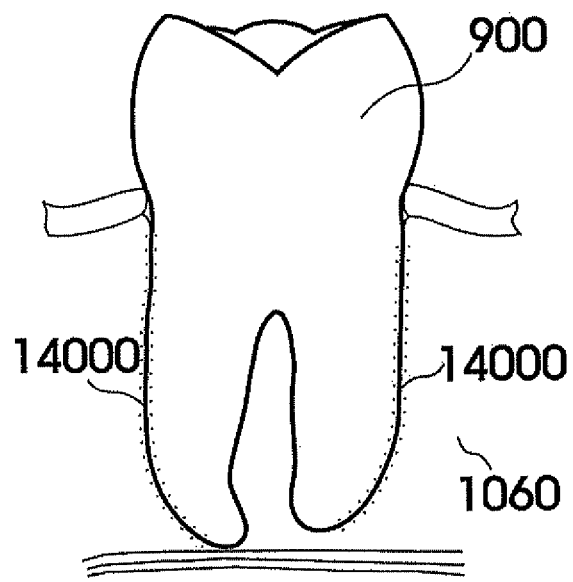
FIG. 17 shows an artificial tooth inserted into the extraction socket and firmly pressed against the walls of the socket in order to promote osseointegration into the bone.

An advantage of this embodiment of the invention is that the complete replacement of the natural tooth is performed in one appointment. After the prosthesis has healed in, only the resin strip initially securing the prosthesis to the adjacent teeth must be removed. A significant amount of laborious steps can thus be avoided. FIG. 17 shows an osseointegrated unsegmented tooth (900). Osseointegration is achieved in marked areas (14000).

Using computer networks, all process steps may be carried out by different and independent parties. The imaging part can for instance be performed at the dentist's office, at a hospital or at a location specialized in imaging. The imaging data can then be transferred to a location where the imaging data are further processed in order to ready them for manufacturing. After the design is finished, the data can again be transferred to the dentist for further optimization and/or approval. Consulting a remote specialist in difficult cases using data transfer may also be applicable. Such a remote specialist may be a clinician or an expert in manufacturing or laboratory procedures. Then, the data can be transferred to a remote manufacturing location. All these data transfers can for instance be performed via the Internet, using preferably Virtual Private Network channels to secure privacy, or through a local area network.

In yet another embodiment shown in FIG. 7, the implant will be made by one type of biocompatible material (9020), for instance, titanium or a titanium alloy, and the portion representing the crown will be coated with another biocompatible material (9010), for instance, ceramic to support both optimal physical strength and esthetics, Alternatively, the crown portion is not coated, but is made from a material different from the material used for the root portion. FIG. 8 shows an artificial tooth, with the portion representing the crown being made from a material having optimized esthetic and/or mechanical properties, while the portion representing the root is made from a material promoting periodontal integration. Both portions can be attached to each other by a variety of connection methods: They can be bonded, cemented, fixed mechanically (either by a screw or an interlocking surface), or they can be fabricated from a workpiece that is already comprising different materials. Sintering would be one of the suitable processes. Therefore, the prosthesis can be fabricated either segmented, with the parts being connected to each other either before or after implantation or the complete prosthesis is made in a single process. In another embodiment, a material promoting cell growth and providing good adhesion for cells is used for the root portions. FullCure 720 may serve as an example of such a material. This is an acrylic based photopolymer and distributed by Object Geometries Ltd., Hebron, Israel. This material can be processed by a rapid prototyping process named "Object Print". Devices for this process are also distributed by Object Geometries Ltd.

In another embodiment, the prosthesis is made from stabilized tetragonal zirconium oxide polycrystalline or another aluminum oxide or zirconium oxide material known to those skilled in the art (inCoris ZI, inCoris AL, VITABLOCS, and CEREC Blocs distributed by and Ivoclar Vivadent and SIRONA). Alternatively, the prosthesis can be made of titanium or a titanium alloy and surface coated with zirconium oxide for example, in sputtering technologies (as offered by Clinical House Europe GmbH).

In case of the osseointegration of a prosthesis according to an embodiment of the invention disclosed herein, INFUSE® can be used. Bone Graft (Medtronic Sofamor Danek) can be applied to stimulate bone formation. INFUSE® Bone Grafts consists of two parts—a solution containing rhBMP-2 (recombinant human bone morphogenetic protein 2) and the ACS (absorbable collagen sponge). The protein is a genetically engineered version of a natural protein normally found in small quantities in the body. The stimulation of bone formation is key to develop osseointegration, and to fill voids in between the extraction socket and the actual prosthesis in an accelerated manner. Other growth aiding proteins like bone morphogenetic protein (BMP), dentin matrix protein (DMP), platelet-derived growth factor (PDGF) and/or other bone growth stimulating proteins may be applied or otherwise used additionally or instead in order to facilitate integration, healing, and rebuild of the bone structure of the patient.

In another embodiment of the invention, cell attracting cytokines are attached or applied to the implant surface to be integrated. For example, that cytokine material InductOss (Wyeth) attracts bone building cells (i.e., osteoblasts) to enhance osseointegration. In contrast specific cytokine material can be applied to attract cementoblasts and/or fibroblasts to regenerate the perio-type membrane and avoid osseointegration.

In a further embodiment of the invention, cells (including but not limited to autologous and/or allogeneic cells) are attached or applied adjacent to or contained in a gel-type scaffold. Agarose gel scaffolds, platelet gel and/or fibrin (Baxter) based scaffolds are used. In order to create a geld type fibrin scaffold, the two components of fibrin sealant are mixed in a ratio 80:20 instead of 50:50.

In yet another embodiment, the prosthesis will not be osseointegrated, but adopted by the ligament of the extraction socket. In this case the prosthesis is coated with a material promoting periodontal adoption. A thin layer of about 0.05 mm to 0.2 mm of resin-modified glass-ionomer cement (FIG. 9, 9000) is applied to the surface of the part of the workpiece being inserted into the extraction socket. FIG. 6 shows a segmented artificial tooth, the crown (10000) being made from a material having optimized esthetic and/or mechanical properties, and the root portion (10010) being coated with a substance (9000) promoting periodontal integration, for instance, glass ionomer cement. FIG. 9 shows an artificial tooth (9030) made from a material suitable for crowns like ceramics, the root portion being coated with a substance promoting periodontal integration. Substances promoting periodontal integration include but are not limited to pharmaceuticals, ancestral cells, proteins, and cell parts of a human tooth.

The meaning of "ancestral cells" shall include but shall not be limited to multi-potent and stem cells, as such cells have the ability to further differentiate.

The meaning of "cell parts of a human tooth" shall include but shall not be limited to PDL-fibroblasts, non-PDL-fibroblasts, cementoblasts, osteoblasts and ancestral cells, having the ability to differentiate into PDL-fibroblasts, non-PDL-fibroblasts, cementoblasts and osteoblasts. "PDL" shall mean in this context "periodontal ligament".

Glass ionomer cement is composed of a calcium-aluminosilicate glass powder and an aqueous solution of an acrylic acid homo- or co-polymer. It is a biocompatible material widely used for tooth restorations and provides good adhesion to the ligament. Resin-modified glass ionomer cement can be light-cured. The light activates a catalyst in the cement that causes it to cure in seconds.

After curing, the artificial tooth is implanted and integrated into the existing periodontal tissue formation of that lower left incisor of the patient and fixed substantially into the same position and inclination of the extracted tooth by being bonded with light curing resin strips to the adjacent teeth.

Another option is coating the portion to be implanted with Ca(OH)2-cement. This is a well known substance in dentistry also used to fill root canals. After setting, EMDOGAIN (Institut Straumann AG, Basel, Switzerland), a substance containing the enamel matrix protein Amelogenin, will be applied. EMDOGAIN is resorbed naturally during the normal healing process, leaving only a residue of enamel matrix protein on the coated surface. This natural and insoluble surface layer encourages the population of cementum-forming cells from the surrounding tissues. Other proteins aiding the growth of dentin, bone or tissue structures like bone morphogenetic protein (BMP), dentin matrix protein (DMP), platelet-derived growth factor (PDGF) and/or or other tissue growth stimulating proteins may be applied or otherwise used additionally or instead in order to facilitate integration, healing, and rebuild of the periodontal ligament. The newly created surface also functions as an interface between the tooth and the surrounding tissues, preventing down-growth of the epithelial tissues. Again, instead of coating, all the aforementioned substances can be applied by other means including but not limited to adjunction and injection. It may be advisable to prescribe antibiotic pharmaceuticals to reduce the infection risk during the healing process. In another embodiment of the invention, the root portion(s) of the prosthesis are coated with a drug releasing surface that releases the aforementioned proteins and antibiotic and other inflammation reducing substances or any combination thereof over time. The drug releasing surfaces can be made, for example, of materials that can be completely resorbed and replaced by natural bone structure or soft tissue.

Especially in the context of periodontal integration, it might be advisable to utilize an absorbable collagen membrane to separate the faster gum growth from the healing process of the periodontal ligament.

In another embodiment, an undersized customized root representation of a ceramic prosthesis is coated with a thin layer of mineral trioxide aggregate (ProRoot MTA, Dentsply) while potential socket irregularities are prepared with calcium sulphate (Capset, Lifecore Biomedical) in order to promote the selective formation of new periodontal tissue (i.e., cementum, periodontal ligament, Sharpey's fibers and alveolar bone) and to build a barrier against an overgrowth by gingival tissue. The thickness of the coating layer should match the undersizing of the root shape and would preferably be chosen to be about 0.2 to 0.3 mm. It would furthermore be advantageous to insert the prosthesis into the socket as soon as possible, but no more than 24 hours (see respective reference re: Spouge, Oral Pathology, Mosby, Saint Louis, 1973 above), after extraction.

Figure 10:
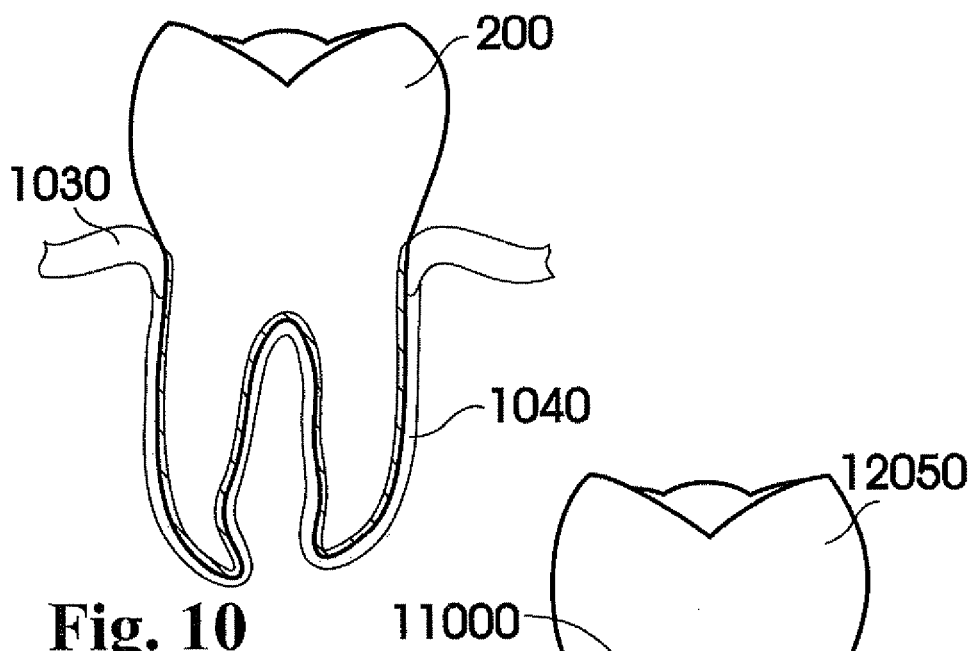
FIG. 10 shows an artificial tooth being embedded in the socket of the natural tooth.

Periodontal integration (FIG. 10) has the advantage that the anchoring of the prosthesis (200) is not stiff as with osseointegrated implants, but shows the elasticity of the natural tooth. The ligaments (1040) are providing support to the teeth in a viscoelastic manner. Furthermore, forces applied to the tooth. and thus, to the ligaments, create tension which is actually the stimulus for bone growth. Another function of the periodontal ligaments is to serve as a method for sensation. To support periodontal integration, the implantation of the prostheses should be performed shortly after extraction of the natural tooth, preferably not more than 24 hours after extraction. A key to success is the preservation of cellular vitality in the periodontal ligament and performing the extraction in a surgical environment under conditions of asepsis. Further below, other embodiments of the invention are disclosed providing instant replacement of the natural tooth.

In another embodiment, suitable pre-determined generic root shapes can be selected and employed for fabricating the portion of the implant to be osseointegrated or integrated into the periodontal ligament. A variety of generic shapes may be stored on a computer-readable media and accessed by the CAD/CAM system.

Another product that is helpful in adapting an implant into the extraction socket is Atrisorb (CollaGenex Pharmaceuticals, Inc., Newtown, Pa.). It helps regrow healthy bone and soft tissues and forms a barrier creating a space in which tissue can grow. Atrisorb is applied as a gel and forms a barrier membrane when sprayed with sterile water. It maintains structural integrity for approximately six months. Complete bioabsorption is achieved within nine to twelve months.

In order to assure that only the desired portions of the prosthesis are adopted by the periodontal tissue, other portions, like the surface intended to carry the crown later to be attached to the implant, may be covered with a substance preventing such adoption. Silver is, for instance a biocompatible material suitable for that purpose. The Fraunhofer Institute for Manufacturing Technology and Applied Materials Research (IFAM) has developed a nano-composite plasma coating technology that can be used for applying a thin layer containing silver.

In yet another embodiment, the crown of the extracted tooth or the tooth to be extracted is not only subject to 3D imaging, but additional color data are obtained. Depending on the scanning method, color data can already be contained in the scan data, or a separate imaging is performed to record the color of the crown. It is possible to obtain a uniform overall color representing the average color of the crown, or alternatively, different shadings for different portions of the crown can be recorded. Based on the color data, the color of the crown can be adapted to the color of the original tooth. The lab technician manufacturing an artificial crown can, for instance, be provided with the color data and select the most appropriate color for the prosthesis. If a complete prosthesis is manufactured using CAM methods, a material best fitting the original color can be used, or a coating can be selected that matches the original color.

In another embodiment, no fixture is used to manufacture the second portion of the artificial tooth. Instead, dedicated feature elements can be added to the shape of the root, such as small holes or posts sticking out, allowing for precise positioning of the artificial tooth for the second step, which is manufacturing the crown portion. These dedicated features can be removed or closed after the complete tooth has been fabricated.

In yet another embodiment, a rapid prototyping process is used for fabricating a prosthesis from hybrid materials. The rapid prototyping process may build the prosthesis layer-by-layer. For instance, a powdery layer of a substance can be applied on top a workpiece, and then portions of the new layer are hardened by a controlled laser beam, while the other unhardened portions are later be removed. In this manner, different substances having different properties (stiffness, hardness, biological properties etc.) can be applied and therefore different portions of the workpiece be made from different materials. In one embodiment, the crown is made from a material different from the one used for the root. In yet another embodiment, the portions representing dentine are made from a material different from the one used for the portions representing enamel.

In another embodiment, the three-dimensional data used to fabricate the dental prosthesis is not acquired from an extracted tooth, but rather, obtained intra-orally with the tooth to be replaced still in place. The advantage of this embodiment is that the complete digital preparation and also the manufacturing steps of the artificial replacement can be performed prior to the extraction. Only when the artificial tooth or segment to be implanted is ready for insertion, the original tooth is extracted. Immediately after extraction, the artificial tooth can be implanted. This contributes to a better healing of the trauma, FIG. 3 outlines the process steps. A CT scan (steps C, Q) is made of the dentition of the patient. The resulting 3D data (D) is imported into CAD software and displayed to the operator (step E). The shape is modified and optimized as needed (step F). The resulting 3D data is converted into IGES format and exported (step H) to a CAM system for fabricating the prosthesis (step I). The process may include coating the finished prosthesis (step J) with a substance promoting bone ingrowth (step K). Only after the prosthesis is ready for insertion, is the natural tooth extracted (step G), and the implant is placed into the extraction socket (step L). It should be noted that although FIG. 3 contemplates possibly interaction with an operator, one skilled in the art would readily appreciate that this functionality may be fully automated.

A NewTom 3G-MF12 Cone Beam CT (NewTom Deutschland AG, Marburg, Germany) can be used to acquire the imaging data. The accuracy of the measurement data will be better than 0.2 mm and therefore highly sufficient for the process. A spline CT with a small envelope dedicated to dentistry like the Morita can deliver 3D data with even better resolution.

The in-vivo structures represented by CT raw data (for example, in DICOM format) can be analyzed by voxel-based software platforms (IVS Solutions AG; Germany) where 3D objects are separated to be distinguished from "grey scale" data. In another embodiment, adaptable algorithms can be used to analyze the dental structures of interest. Such adaptable algorithms can use known data of for example, generic shapes to drive the adoption of "grey scale" filters.

Further, methods for intra-oral imaging include but are not limited to CT, CBCT, MRT, ultra sound, active triangulation, passive triangulation, confocal scanning, and TOF (Time-of-Flight). The anatomical structures obtained by intra-oral imaging include but are not limited to periodontal structure, the alveolus, and the jaw bone of the patient.

Using intra-oral 3D imaging, it is even possible to perform a scan of a patient long in advance and to file the personal imaging data of the dentition of the patient. In case of an injury or accident where teeth get lost or busted or are not available for a scan for any other reason, a fabrication of individual prostheses can be initiated immediately, using the previously collected imaging data.

Figure 14:
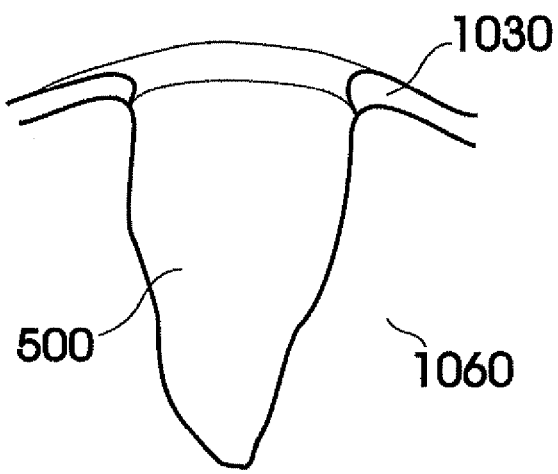
FIG. 14 shows an extraction socket.

Instead of 3D imaging and digitally processing imaging data, copy milling or copy grinding from the original tooth or parts or the tooth can be performed. The root can also be shaped according to an impression made directly from the alveolus of the extracted teeth as shown in FIG. 14, using a specialized material or using standard impression materials separated from the surface (periodontal ligament or bone) of the alveolus (500) by a very thin film of plastic or another material suitable for the purpose. Alternatively an impression can be taken from the extracted tooth. Laboratory methods for fabricating dental prostheses basing on impressions are readily available. These methods mostly involve using casting processes or employing light curing or chemical curing processes where monomer components are polymerized to molecular networks. Further, methods of fabricating a substantial copy of the original tooth include but are not limited to depositing, sintering, 3D printing, molding, curing, grinding and milling. The ongoing progresses made in rapid prototyping, that is, fabricating individual parts directly basing on digital data, will strongly contribute to this invention.

Figure 23:
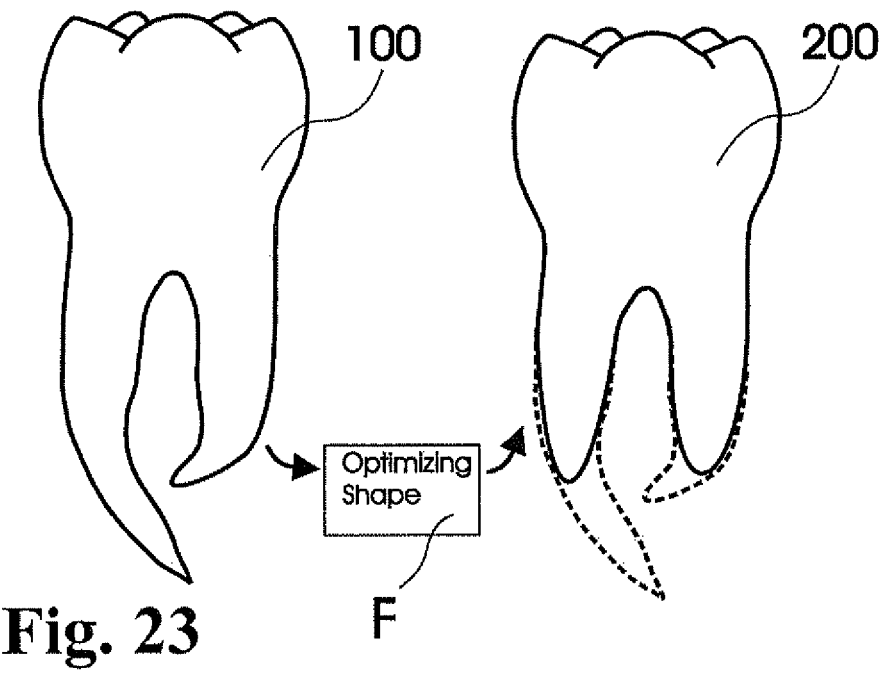
FIG. 23 shows a natural tooth having strongly crooked roots and the artificial substitute, wherein the shape of the substitute has been altered in order to allow for simplified insertion into the natural socket.
Figure 24:
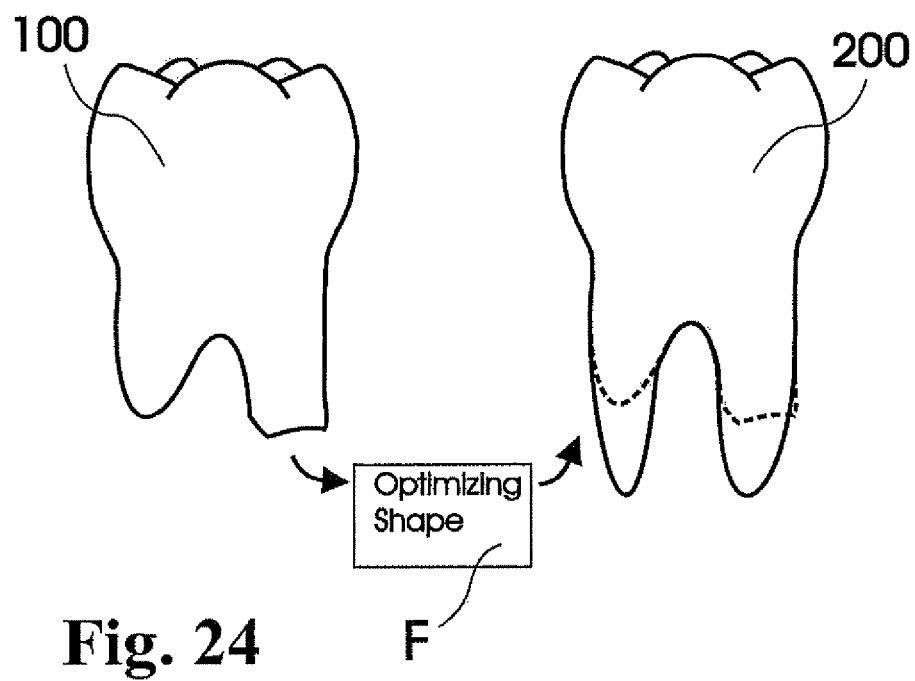
FIG. 24 shows a natural tooth suffering from partial root loss due to root resorption or a surgical procedure and an artificial substitute, the shape of the artificial tooth being optimized for better adaption to the natural socket.
Figure 25:
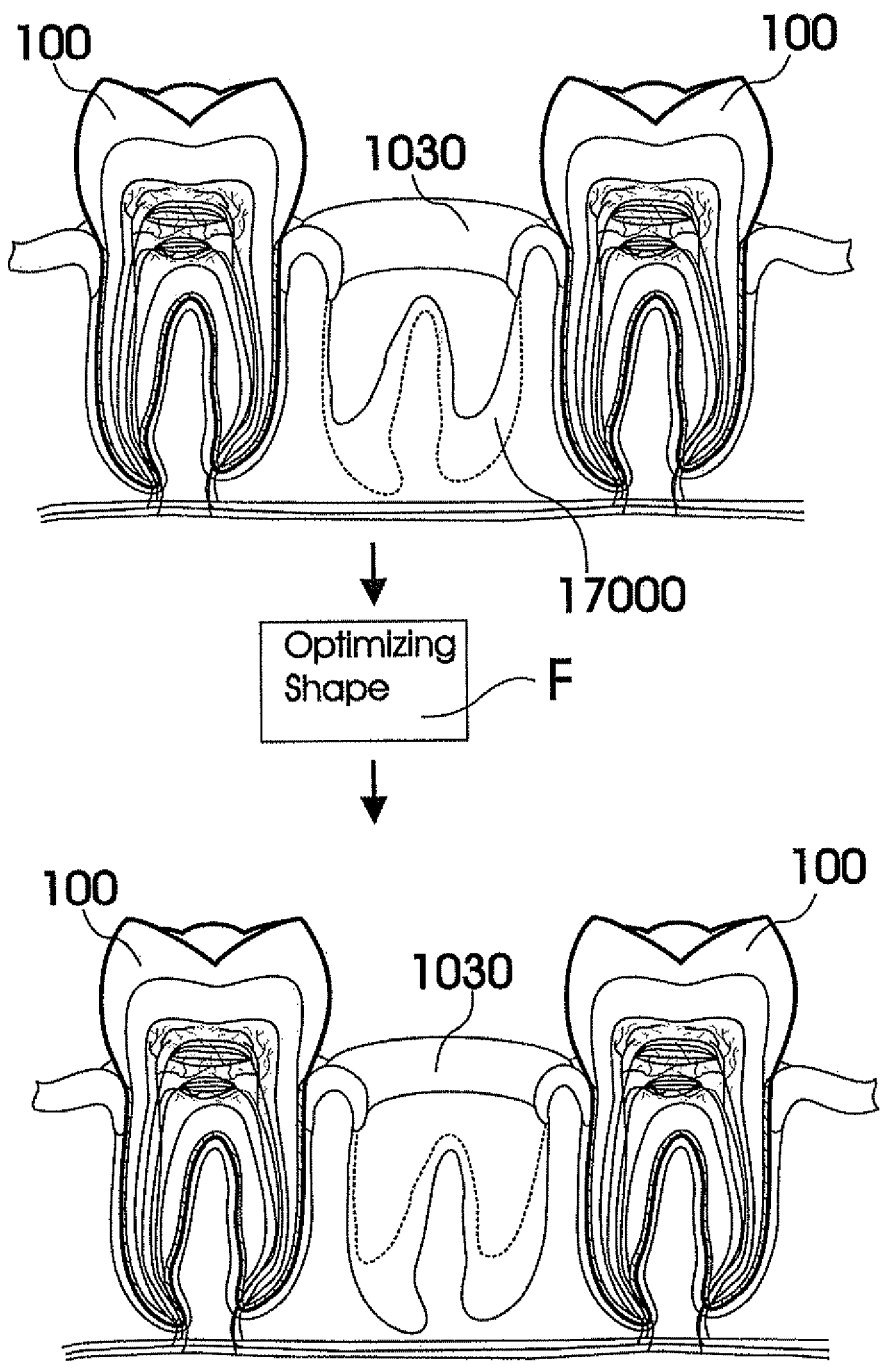
FIG. 25 shows a tooth socket after extraction. Due to root resorption, the size of the socket has been reduced over time. In order to enhance anchoring, the artificial replacement will have a root portion of greater size. Therefore, the socket is surgically enlarged.

In some cases the shape of the original roots will present difficulties on the insertion of the artificial replacement. In such cases, a proper modification and optimization of the shape of the artificial root according to FIG. 23 is applicable. In other cases, the root of the natural tooth may be suffering from partial root loss due to root resorption or a surgical procedure. In these cases, the root of the replacement may be adapted to the extraction socket as demonstrated in FIG. 24. For example, the customized portion includes a substantial copy of at least 60% of the root shape of the natural tooth while the other portion of the artificial root is modified as described herein. In other cases, the size of the socket may have been reduced over time due to root resorption as displayed in FIG. 25. The size reduction has occurred in areas (17000). In such cases, it is advantageous to enhance anchoring by surgically enlarging the socket and to adapt the root of the artificial tooth to the enlarged socket. SolidWorks is a suitable CAD software to alter the shape of the implant with respect to the original imaging data.

Figure 22:
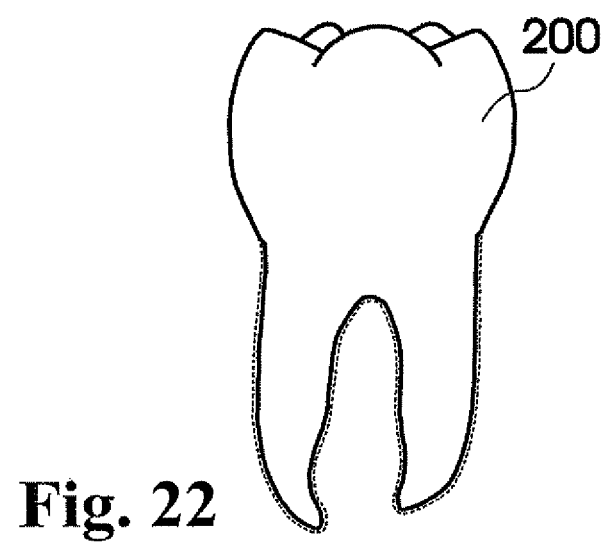
FIG. 22 shows an artificial tooth, the portion representing the root being slightly reduced in size compared to the natural tooth.

There are more reasons to modify the shape of the implant with respect to the original root. To ease insertion into the extraction socket, the shape of the implant may be slightly undersized as shown in FIG. 22. MAGICS provides a functionality allowing for a simple reduction of the overall size of a body. On the contrary, an oversized artificial root may be desirable in order to receive a very tight mechanical fit in the extraction socket to promote osseointegration as displayed in FIG. 17. This can also easily be achieved with MAGICS. This software has a couple of helpful features that have originally been developed to optimize plastic parts for injection molding, but turned out to be useful also for the processes of various embodiments of this invention.

In an exemplary embodiment, the root portion of the prosthesis adjacent to the bone socket of the extraction site substantially mimics either the root shape of the non-functional tooth to be replaced or the three-dimensional shape of the bone socket or any combination thereof, but will be dimensioned not to exceed the shape of the bone socket in order to avoid a conflict when positioning the prosthesis clinically in the pre-defined position and inclination. In a further embodiment, measurement and/or manufacturing tolerances are considered undersizing the root portion adjacent the bone socket in its design. Manufacturing tolerances are to be estimated between 10 and 50 micrometers. Measurement tolerances are to be estimated between 20 and 400 micrometers.

In yet another embodiment of the invention, original portions of the natural tooth will be integrated into the implant. Especially portions of the root still being covered with cement can greatly improve adoption into the ligaments of the extraction socket. On order to integrate those natural portions, they will be cleaned and prepared for imaging as described further above. The resulting 3D imaging data will be imported into MAGICS and processed like the data of a complete tooth. The three-dimensional virtual body will then be placed at the proper location with respect to the virtual body representing the shape of the implant to be produced. Using Boolean functions of MAGICS, the body representing the natural portion(s) of the tooth will be subtracted from the body representing the implant, thus, creating a cavity in the implant having the exact size and shape of the natural portion(s) of the tooth to be integrated into the implant. After the implant has been fabricated and processed, the natural portions of the tooth are cemented into the implant.

Figure 13:
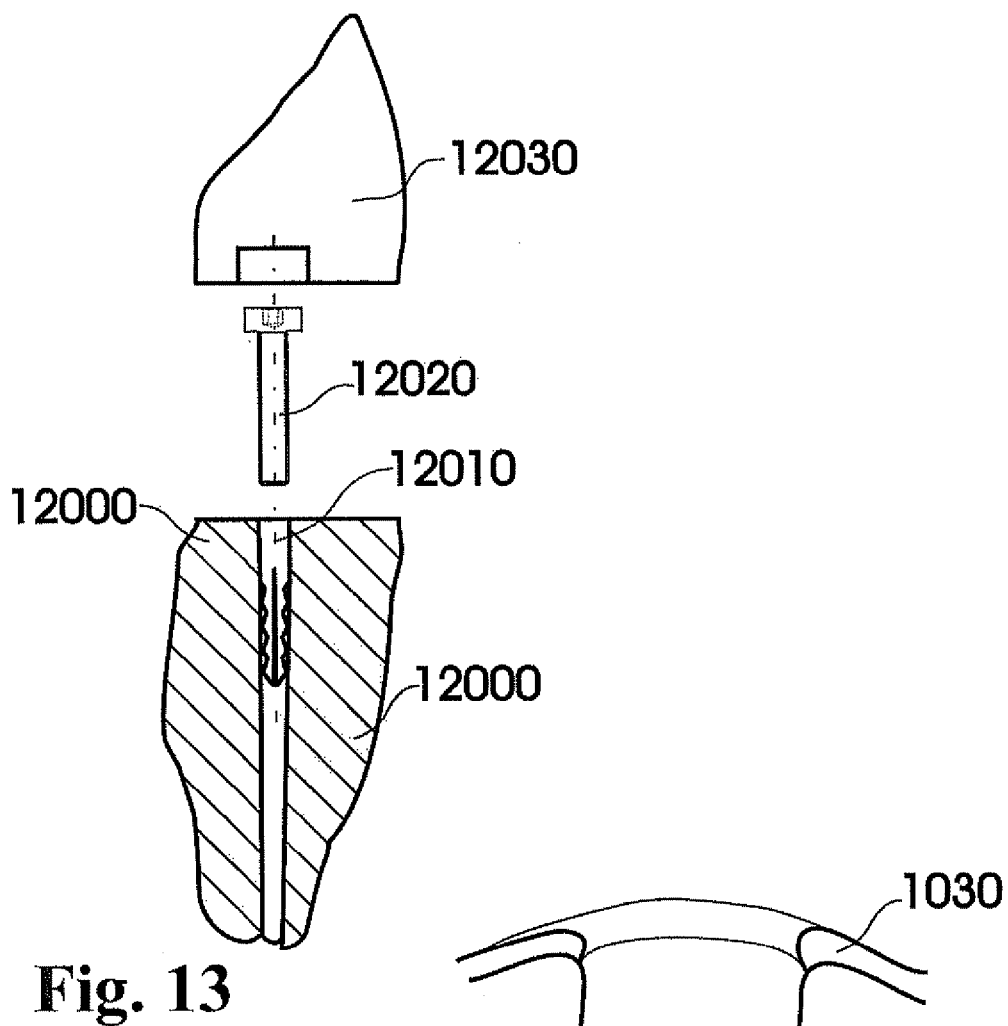
FIG. 13 is a cross-sectional view of a segmented artificial tooth, the segment representing the root being expanded using a screw and a dowel in order to support osseointegration and improve physical stability after implantation.
Figure 15:
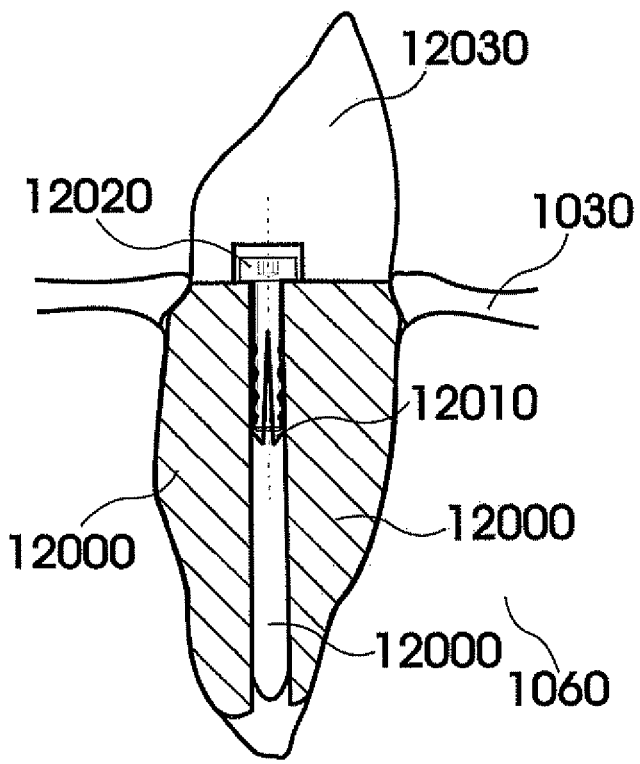
FIG. 15 is the artificial tooth of FIG. 13 inserted into the extraction socket and expanded.
Figure 16:
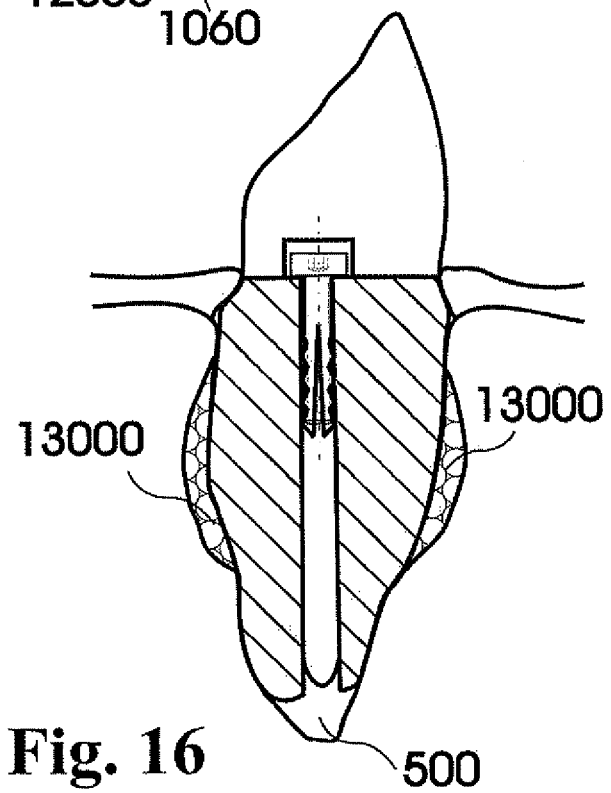
FIG. 16 is a view of an artificial tooth according to FIG. 15, wherein voids between the socket and the tooth are filled with a bone promoting substance.

In yet another embodiment of the invention, firm anchoring of the implant is achieved by expanding the portion being located in the extraction socket in order to support osseointegration and improve physical stability after the implantation. By expanding the implanted portion, forces are applied to the alveolus or bone. In this embodiment, the artificial root is shaped to form an expansion anchor. Expansion can be achieved by either using a material changing its shape due to temperature changes after insertion like SMA (shape memory alloy) or by using a material like shape memory polymers activated by electromagnetic radiation. Expansion can also be achieved mechanically by placing a dowel inside the artificial root. This is demonstrated in FIGS. 13 and 15. The root portion of the implant is slotted, thus forming posts or wings (12000) and made from a material providing sufficient elasticity in conjunction with the slots. When screw (12020) is inserted into dowel (12010), the posts are pressed against the walls of the extraction socket. The crown (12030) is attached to the implant after insertion, using standard procedures known in prior art. FIG. 16 displays such an implant located in an extraction socket where voids have been filled with a substance (13000) promoting bone growth like Bioplant or CERASORB. In FIG. 35 another embodiment is displayed. No dowel is used, but instead the thread is conical. When screw (12020) is inserted into the conical thread, the wings (12000) are accordingly expanded and pressed firmly against the extraction socket, as demonstrated in FIG. 36. Alternatively, the initial pressure supporting the fast integration into the bone may be performed by for example, three oversized small grooves positioned on the outer surface parallel to the longitudinal axis of the root causing pressure when the artificial root will be inserted.

To achieve a long living prosthesis, the size and the shape of the root and the socket needs to be appropriate to enable solid anchorage in the bone. If, for example, a root is too small to absorb the normal chewing forces it may be necessary to expand the size of the socket before designing and manufacturing the customized root. Other patients may not have enough bone material, so that the thickness of the bone gingivally and labially is not sufficient for the anchorage of an implant. In such a case, the root may be shaped like a clamp so that the corticalis is used for the anchorage. This approach is known as the "juxtaosseous" method (the implant adapts to the bone and not the bone to the implant). If an appropriate material like titanium in combination with biological ossifying substance is used, the bone adapts to the implant and so the implant becomes an osseointegrated implant. For abutments, this is already successfully being used by the San Babila Day Hospital in Italy. Even more solidity can be achieved by a "multi-legged" root shape combining an artificial root and clamp shaped outer part for the adaptation to the corticalis. This approach significantly increases the stability of the anchorage because no hollow or less stabile areas remain in the bone. If crown and root are manufactured as one part, the crown may be coated with an enamel-colored layer or multiple layers for aesthetic reasons. Such layer(s) can be, for example, translucent to a certain extent. During the healing process, appropriate measures need to be put in place to avoid early exposure of the implant to forces (bite bumpers, partials positioners, etc.).

Figure 20:
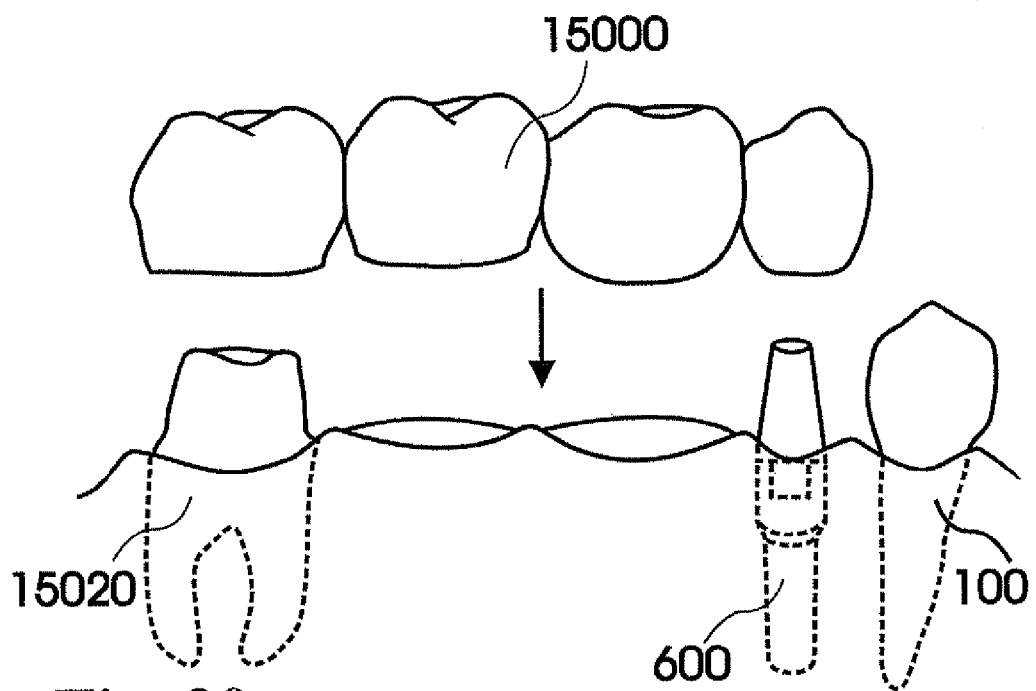
FIG. 20 is a view of a bridge according to prior art.
Figure 21:
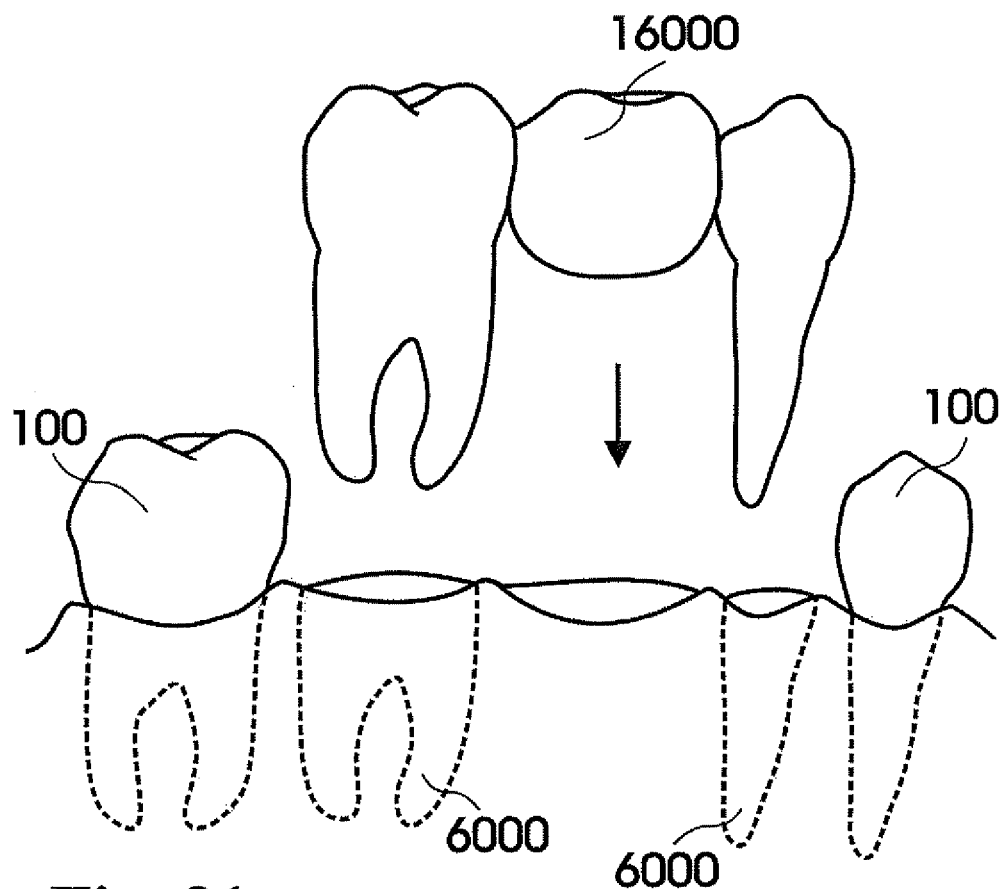
FIG. 21 is a view of a bridge according to an embodiment of the present invention.

The invention is not limited to the replacement of a single tooth. It is possible to manufacture dental bridges, whereby the lateral teeth have root features that can readily be implanted into an existing socket. Conventional dental bridges (15000) as displayed in FIG. 20 are cemented onto natural teeth with the crown being grinded down (15020) or onto conventional implants (600). According to this invention, the natural sockets (6000) can be used as shown in FIG. 21 for attaching the bridge (16000), with the adjacent teeth (100) staying healthy and complete. It is also possible to fabricate a partial prosthesis to be implanted into the natural socket, said prosthesis being the anchor for a later installment of a dental bridge. This embodiment is especially useful in cases where one of the two lateral supports of the bridge is already present, and the bridge therefore needs to be cemented.

According to various embodiments of the present invention, due to the ability of the suggested manufacturing processes, a respective embodiment of the invention allow the fabrication of prostheses representing crowns, roots, bridges, segments or any combination thereof, and also the entirety of a dentition.

In another embodiment, off-the-shelf abutments can be integrated into the artificial root using the intended connection method recommended by the manufacturer like screwing them into the artificial root with or without drilling a hole, clicking them onto a counter shape or others.

In yet another embodiment, the components will be molded directly into the artificial root.

Figure 11:
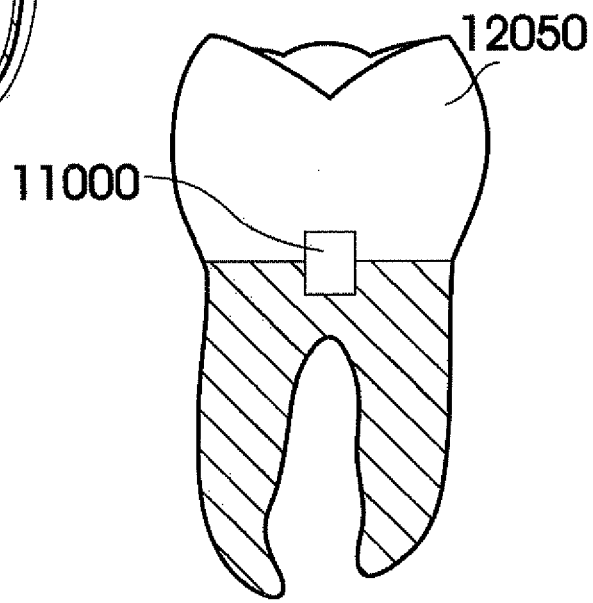
FIG. 11 shows a view of a segmented artificial tooth, the segment representing the root being connected to the segment representing the crown by a connecting element.
Figure 12:
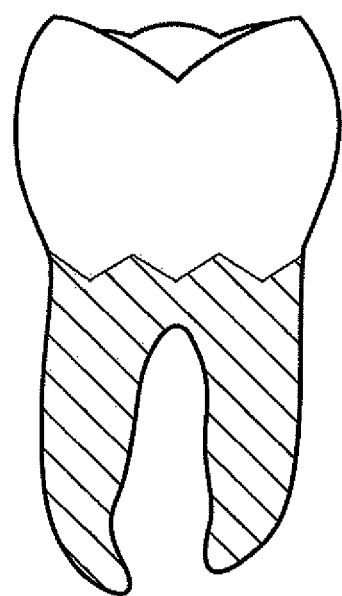
FIG. 12 is a view of a segmented artificial tooth, the segment representing the root and the segment representing the crown having an interlocking connection.

In yet another embodiment, the artificial root will comprise a feature on its occlusal-facing surface shaped in a way that it allows for assembly of a conventional veneer or a pre-manufactured veneer or crown to the root. The occlusal-facing surface can also be shaped to provide an interlocking connection to the crown as shown in FIG. 12. The occlusal surface can also have all kinds of connecting features (11000) symbolized in FIG. 11 to allow for attachment of a crown (12050).

Figure 18:
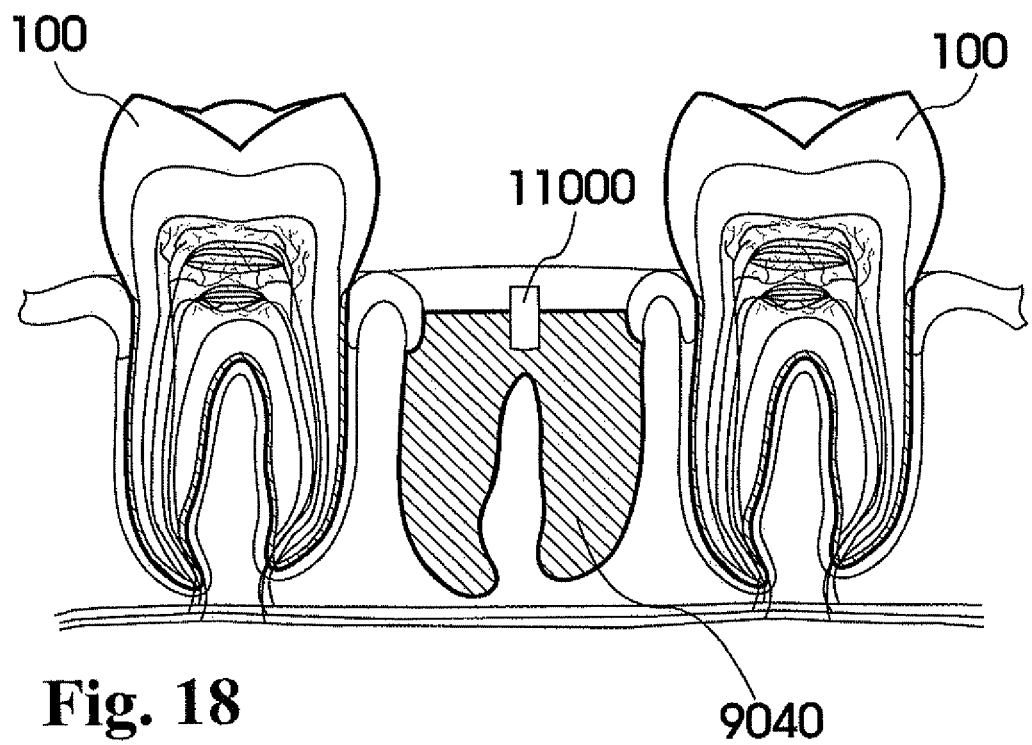
FIG. 18 shows an extraction socket of a patient, the socket filled with a bone promoting substance, and a connection element for the root being embedded into the bone promoting substance.
Figure 19:
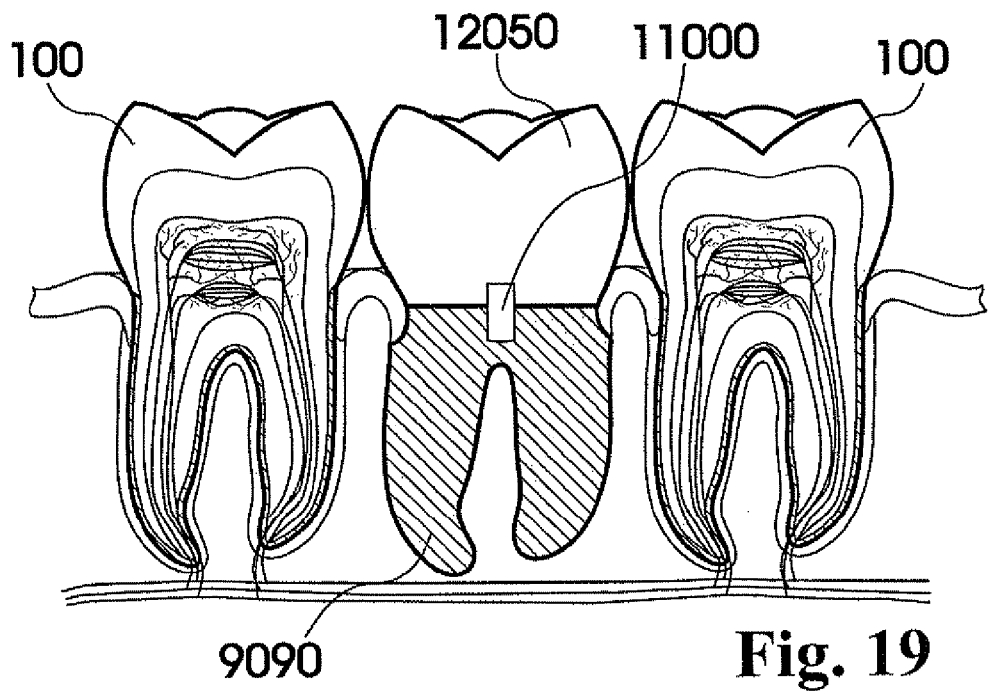
FIG. 19 shows an artificial crown attached to the connection element of FIG. 18 after the bone promoting substance has been replaced by newly grown bone.

In yet another embodiment as shown in FIG. 18, the extraction socket will be filled with a bone promoting substance (9040), and a connection element (11000) for the root is embedded into the bone promoting substance. FIG. 19 shows the artificial crown attached to the connection element of FIG. 18 after the bone promoting substance has been replaced by newly grown bone (9090).

In another embodiment, the time needed for the adoption into the periodontal ligament will be reduced and/or the strength and/or the life-time of the connection to the surface of the artificial root will be optimized by increasing the surface by sandblasting, adding a mesh or other suitable means, and/or adding pharmaceutics or other substances supporting the integration of the chosen material of the artificial root into the periodontal ligament such as, for example, the protein amelogenin. These pharmaceutics can be applied by conventional or state-of-the-art methods like dry or liquids suspensions to be painted onto the artificial roots before integration, or by injection with a hypodermic needle or intra-orally through pills. Also, ancestral cells may be used to support the rebuilding of the periodontal ligament.

Membrane techniques may be used to protect the area dedicated to the relatively slow growing periodontal ligaments from the fast growing gingival epithelium.

In another embodiment, decreasing the time needed for the osseointegration and/or increasing the strength and/or the life-time of the connection to the surface of the artificial root can be achieved by increasing the surface by sandblasting, adding a mesh or other suitable means, and/or adding pharmaceutics supporting the integration of the chosen material of the artificial root into the bone. These pharmaceutics can be applied by conventional or state-of-the-art methods like dry or liquid suspensions to be painted onto the artificial roots before integration, or by injection with a hypodermic needle or intra-orally through pill and/or ray treatment.

In another embodiment, the shape of the artificial root will not completely reflect the shape of the root to be replaced. In order to strengthen the connection with the periodontal ligament or the bone, the shape will be modified. If, for instance, the three roots of a molar are located very close to each other, the three roots will be replaced by only one root which will comprise parts of the original shape of the three original roots.

There is a lot of software readily available on the market that allows for easy and intuitive modification of 3D shapes, Both previously mentioned programs: MAGICS and Solid-Works are suitable for this task.

In another embodiment, the closure of remaining gaps between the artificial root and the socket used for implantation can be accelerated by suitable pharmaceutics and/or ray treatment.

In yet another embodiment, the prosthesis is an assembly of one or more parts where the interfaces between such parts are sealed in order to provide a barrier against bacteria infiltration. The sealing can include, for example, a labyrinth feature.

In another embodiment, the root portion of the prosthesis is an assembly that is configured to extend one or more barbed hooks which in a favorable embodiment are each connected to the root body with a hinge and activated by a leave spring.

Conventional two-piece implants as shown in FIG. 37 consist of an implant (600) to be osseointegrated that includes an abutment portion and an artificial crown (12030). Conventional three-piece implants as shown FIG. 38 consist of an implant (600) to be osseointegrated, an abutment (19000), and an artificial crown (12030). In either configuration these conventional implants (600) and the abutment (19000) are mass produced and have a generic shape. The artificial crown (12030) will be made in a dental laboratory based on impressions of the embedding dental situation which includes the abutment portion of the implant after integration into the dental anatomy of the patient. In other words, the crown will be made based on the geometrical relation between the implant and the abutment (portion) after placement.

Figure 39:
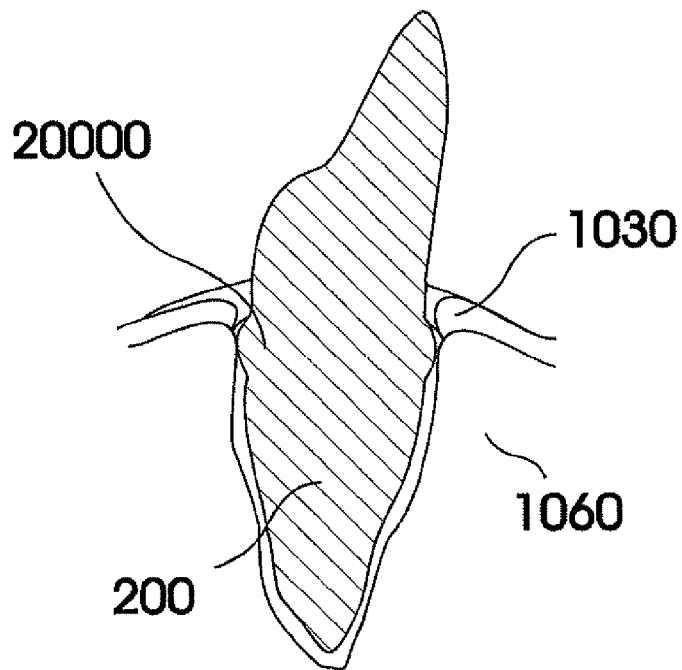
FIG. 39 is a single-tooth prosthesis for osseointegration showing a custom shaped torus as a barrier against tissue growth.

In contrast, the prosthesis according to an embodiment of the present invention is manufactured in all its parts or as a single piece in its entirety before being integrated into the dental anatomy of the patient of interest. FIG. 39, for example, shows a tooth-shaped one-piece prosthesis having an integrated root portion and an integrated crown portion (200). The prosthesis (200) can be shaped with or without a custom shaped torus (20000) that circumvents the prosthesis in a height of, for example, 0.5 mm below the line of gingiva (1030). The torus (20000) builds a barrier against in-growth of the gingival tissue. In case the prosthesis (200) is configured for osseointegration, the cavity in the bone (1060) is virtually sealed, and osseointegration will take place without being disturbed by isolating lobes of gingival tissue growing between the prosthesis and the cavity. In case the prosthesis (200) is configured for periodontal integration, the gap between the prosthesis and the extraction socket is sealed against fast growth of gingival tissue, so that the integration into the periodontal ligament structures, having a reduced growth rate in comparison, is protected.

In yet another embodiment, the prosthesis is an assembly (as shown for example, in FIGS. 5, 6, 8, 11, 12, 13, 15, 16, 18, 19, 31, 34, 35, 36, and 45) of two or more parts. The parts are, for example, glued, sintered, mounted by pressure, and/or screwed to each other. The interface between connecting parts needs to be sealed against bacteria infiltration. Special sealing concepts like O-ring sealing and labyrinth sealing may apply.

Figure 40:
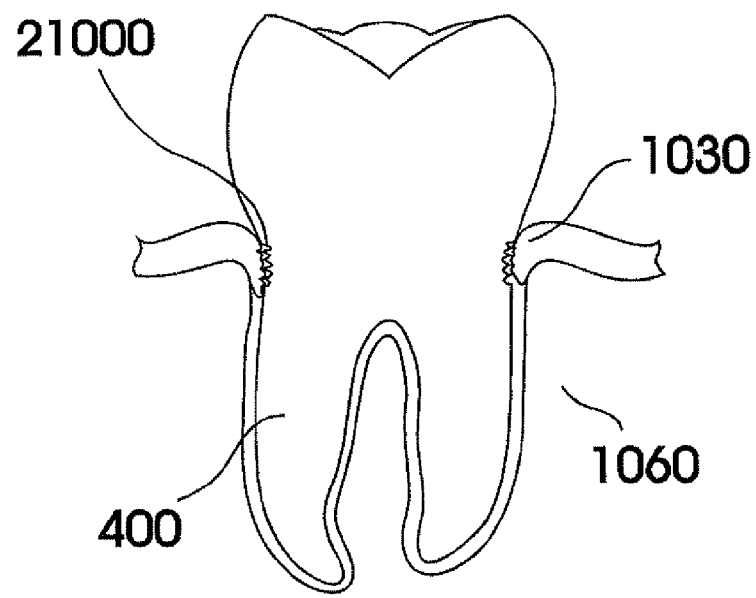
FIG. 40 is a single-tooth prosthesis showing a labyrinth-sealing feature as barrier against bacteria infiltration.

In another embodiment as shown in FIG. 40, the prosthesis (400) has a sealing feature (21000), which is circumventing or partially placed between the crown portion and the root portion of the prosthesis (400). The sealing feature (21000) is either simply an indent or a labyrinth feature that builds the interface between the material of the prosthesis and the gingiva (1030). The respective interface seals the structure between the prosthesis and the extraction socket against bacteria infiltration in order to gain long-term stability and to avoid pockets.

Figure 41:
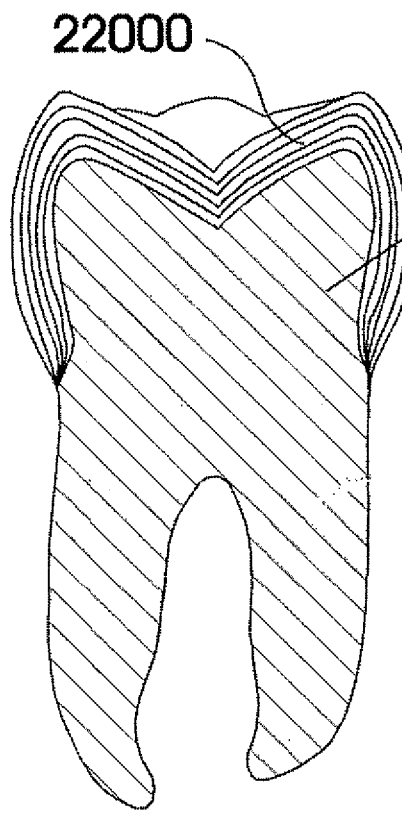
FIG. 41 is a single-tooth prosthesis showing a build-up of a crown portion of translucent ceramic layers.

In another embodiment, the crown portion of a prosthesis is fabricated in an undersized shape compared to the final shape of the crown. Single or multiple layers of translucent ceramics are added in a laboratory process to gain esthetic performance compared to the appearance of a natural tooth. FIG. 41, for example, is a single tooth prosthesis having an undersized crown shape (200) and a build-up of several ceramic layers (22000). It is also possible to use other esthetic materials having one or more than one layer. In another embodiment, the build-up (22000) is, for example, made of elastic materials (like an elastic cover) in order to soften early contacts and foster in this way the healing process after integrating the prosthesis.

Figure 42:
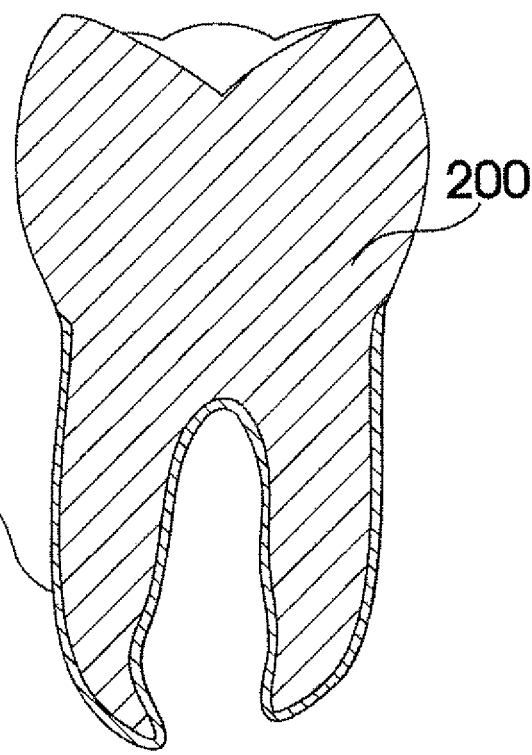
FIG. 42 is a single-tooth prosthesis showing a root portion having drug releasing surface.

In yet another embodiment, a prosthesis is at least partially made of one of the following: titanium, titanium alloy that consists of more than about 60% of titanium, cement, zirconium oxide, ceramics, synthetics, elastics, plastics, stainless steel, glasiomer cement, resin-ionomer cement, hybrid-ionomer cement, resin-enforced cement, and acrylic based photopolymer, or any combination thereof. In a further improvement, the prosthesis includes a drug releasing surface, releasing over time medical substances. Such substances include, for example, one of the following: Antibiotic or other infection suppressing pharmaceuticals, growth promoting substances (for example, ancestral cells, proteins, and cell parts of a human or animal tooth) or any combination thereof. FIG. 42 is, for example, a single-tooth prosthesis (200) having a drug releasing surface (23000) covering at least a portion of the root part of the prosthesis (200).

In yet another embodiment, a prosthesis is fabricated based on imaging data of the patients dental anatomy. The imaging data includes three-dimensional representations of one tooth or two or more teeth. Each tooth includes a crown portion and root portion. The imaging data can be made either prior to or after extraction of the tooth or teeth to be replaced. The imaging data can include in-vivo data or data made in-vitro from one tooth or two or more teeth after extraction. Other imaging data are derived from physical impressions made of a dental anatomy. Dental anatomy includes the occlusion, the articulation, the geometrical (spatial) relationship between the teeth within one arch or between upper and lower arch of a patient, or parts thereof.

Dental anatomy also includes the structures holding the tooth/teeth which include soft tissue structures and bone structures and any combination thereof. Imaging data can include two dimensional representations (for example, X-ray films, facial photos) or three-dimensional representations (like CT or MRT data). Imaging data can be any portion of the aforementioned data and/or any combination thereof. All these imaging data can be merged, overlaid and combined to derive shape data of a design of a prosthesis.

Figure 43:
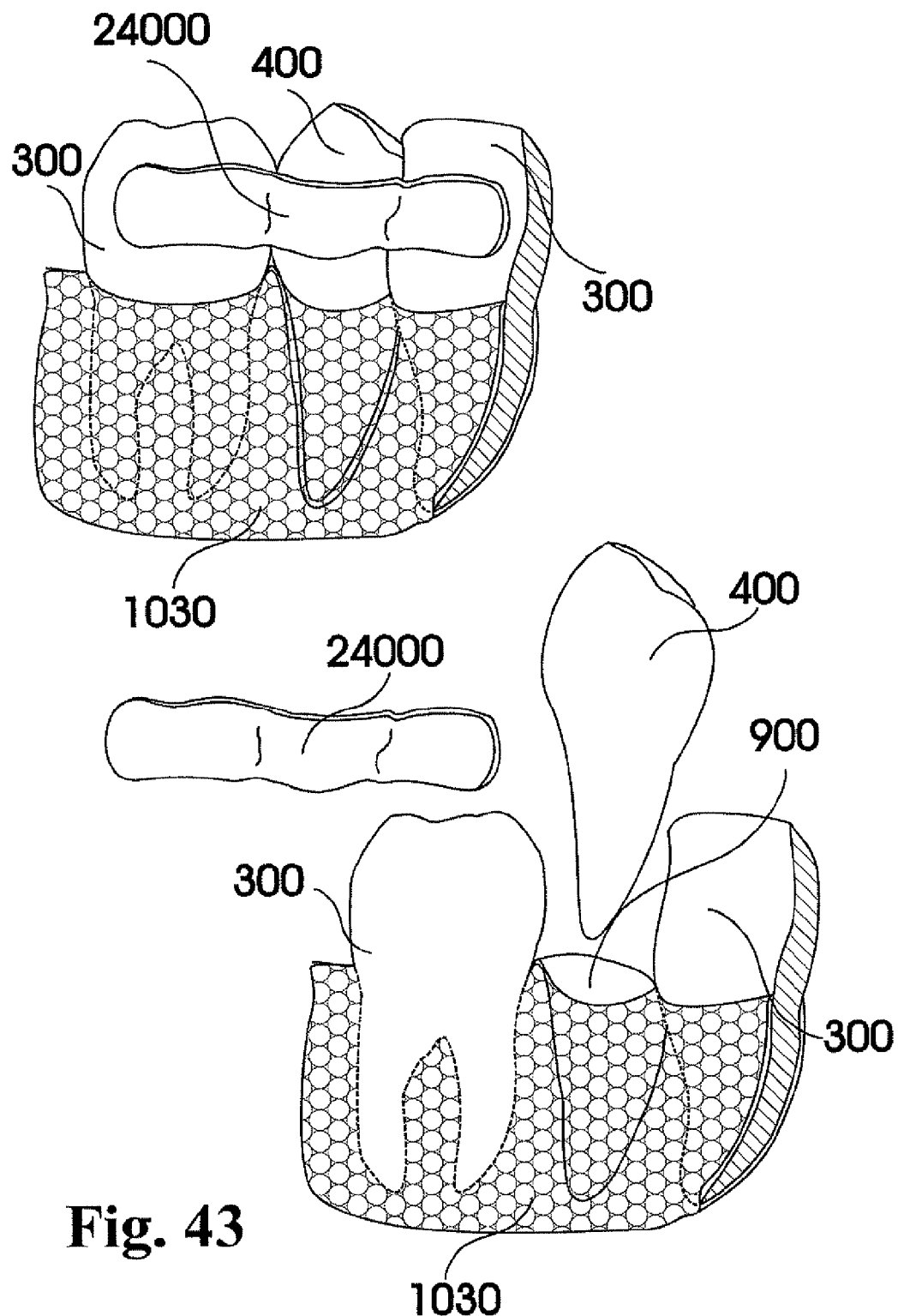
FIG. 43 is a single-tooth prosthesis and a custom-made splint for positioning and fixation of such to the adjacent dental structure.

In another embodiment, FIG. 43 is a single-tooth prosthesis (400), having a manufactured crown portion and a manufactured root portion. The shape of each is derived, for example, from in-vivo imaging data prior to the extraction of the tooth to be replaced. By extraction of said tooth to be replaced, the extraction void (900) was created. The adjacent teeth (mesial and distal of the extraction socket) are healthy natural teeth (300). The extraction was indicated, for example, due to a serious porosity of the root of the extracted tooth. The extraction socket was partially curetted by the doctor of record, removing damaged soft tissue. Antibiotic tablets are given orally to the patient in advance to suppress the inflammation and to avoid additional infection as a result of the clinical trauma of removing the tooth. The crown and the root shape are derived from the imaging data. In addition the crown shape of the adjacent teeth (300) and a desired position and inclination of the prosthesis are derived from the imaging data. Based on all this data a custom-shaped splint (24000) is designed and fabricated. The splint is used to position and orient the prosthesis (400) in the dental structure (1030) building the extraction void in geometrical relation to the adjacent teeth (300). Being held in the desired position and orientation, the custom-shaped splint (24000) is glued with adhesive means to the prosthesis (400) and the adjacent teeth (300). For example, light curing adhesives are used in that context. Finally, the prosthesis (400) is fixated in its desired position and the crown portion is thereby integrated into the occlusion and articulation of the patients dental anatomy. Slight corrections performed by the doctor of record with a high-speed rotating instrument may be necessary to optimize the occlusal contact points. The prosthesis can be immediately loaded by the patient for the day-to-day use of mastication. The custom splint glued to a prosthesis and adjacent teeth or other dental structures provides the primary stability while either the periodontal integration or the osseointegration takes place.

Although shown in FIG. 43, not to interfere with the occlusion of the upper and lower dentition of the patient receiving the appliance when inserted, the splint can also have an extension that covers, for example, not only the lingual crown portions of the prosthesis and of the adjacent teeth, but includes also incisal edges in the event anterior teeth are affected or cusps in the event posterior teeth are affected. In a further embodiment, significant occlusal surfaces of the teeth of interest can also be covered by the splint. In an exemplary embodiment, the design and the fabrication of the splint may include such contours covering additional surfaces or portions thereof to enable better positioning of the prosthesis, with such contours to be physically removed after bonding in the patient's mouth by the doctor of record.

Figure 44:
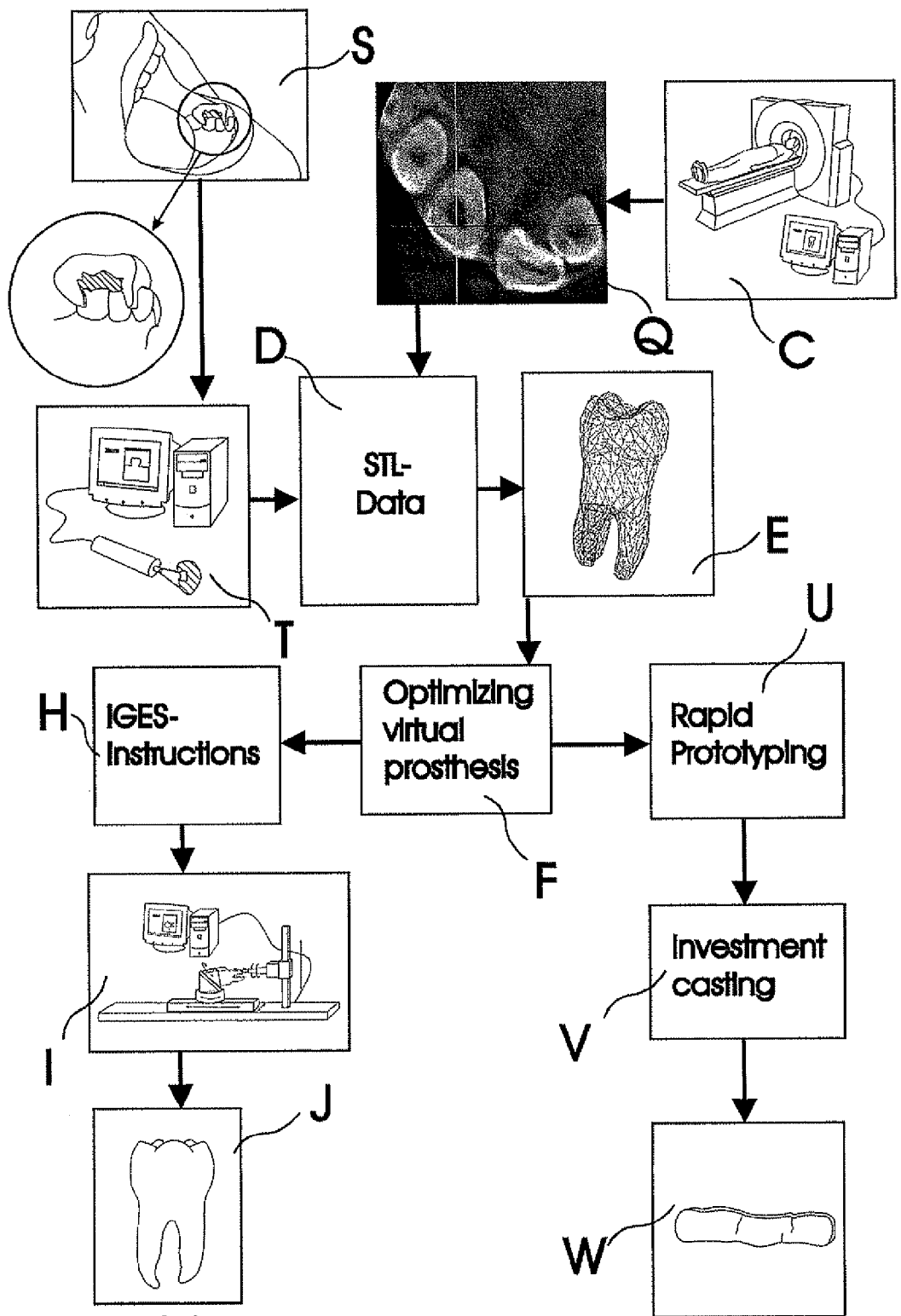
FIG. 44 shows the process steps of fabricating a one-piece prosthesis partially from in-vivo imaging data and partially from imaging data of impressions, merging those imaging data design a prosthesis and a custom splint, and fabricating the prosthesis and the splint by computer numerical control (CNC) machining.

In the context of the aforementioned custom splint, FIG. 44 shows, for example, the process steps of fabricating such a prosthesis and such a splint. A partial silicone impression is taken from the mouth of the patient representing the dental (occlusal) crown anatomy in the neighborhood where a prosthesis will be integrated (step S). The impression is scanned and three-dimensional STL data of the shape are derived representing the crown geometry of the tooth to be extracted, the crown geometry of the adjacent teeth, and the geometrical relation between those crown data (step T). Additionally, the patient's dental anatomy is imaged with a computed tomography device (step C). Computed tomography (CT) is a medical imaging method employing tomography where digital geometry processing is used to generate a three-dimensional image of the internals of an object from a large series of two-dimensional X-ray images taken around a single axis of rotation. The layered grey scale X-ray data in digitized format are then computer analyzed and voxel as well as three-dimensional STL data are derived representing the dental anatomy of the patient (step Q). All aforementioned STL data can be scaled, merged and/or combined to generate accurate three-dimensional shape data from tooth to be replaced and the adjacent dental anatomy (step E). Boolean algorithms can be used to generate combined data of high-quality. In a first design of the prosthesis, its position and orientation within the adjacent dental anatomy, especially in relation to the crown portions of the adjacent teeth, and a second design of a custom shaped splint that includes shape portions of the crown of the prosthesis and of the crowns of the adjacent teeth, are derived. The first and the second design may be modified and optimized (step F). This can be done automatically or interactively by having a technician operating the respective computer equipment. Computer numerical control data (CNC), for example, in IGES format for computer aided manufacturing (CAD) devices are derived from the final three-dimensional design data (step H). Usually rapid prototyping equipment is having the aforementioned step already integrated. The prosthesis is fabricated in response to the IGES data, for example, by a CAM high-speed milling/grinding machine (step I and J). Additionally, the rapid prototyping machine, such as, for example, a layer-by-layer wax printing machine, is fabricating a three-dimensional wax representation (sample) from the three-dimensional design data (step U). The sample is prepared and embedded for lost wax investment casting, whereby the wax sample is burned out and the investment mould is filled with liquid precious metal (e.g., dental gold alloy; step V). After cooling down to room temperature, the embedding material is removed, the runner is cut-off and the splint is polished and surface prepped for bonding (step W). It should be noted that while FIG. 44 contemplates possibly interaction with an operator, one skilled in the art would readily appreciate that certain steps are combined, further differentiated, and that this functionality may be partially or fully automated.

Figure 45:
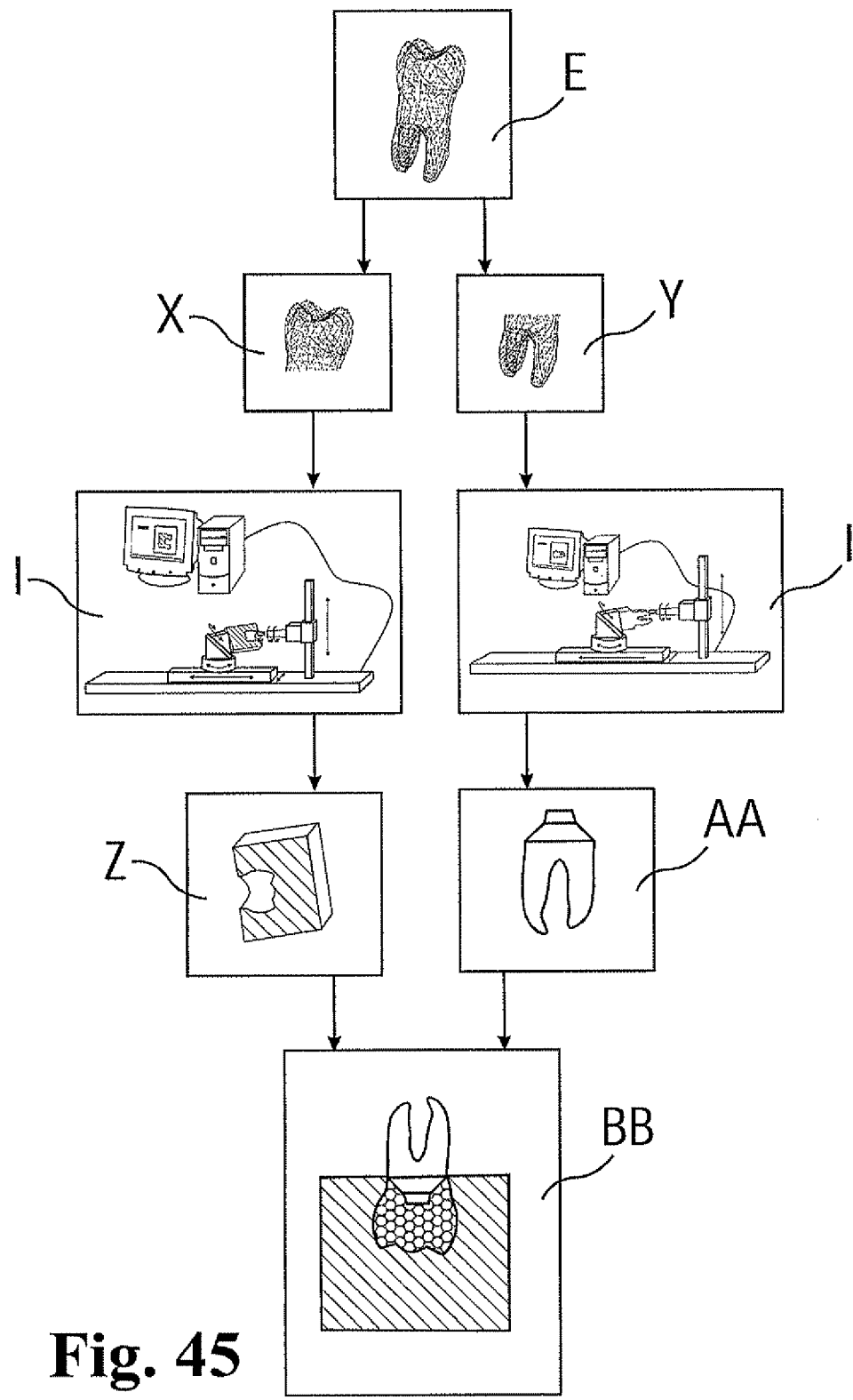
FIG. 45 shows the process steps of fabricating a one-piece prosthesis from design data, completing the design by segmenting the prosthesis in a root portion that includes an abutment and a crown portion, fabricate the root portion by computer numerical control (CNC) machining, fabricating a negative shape of the crown portion as a mould by computer numerical control (CNC) machining, and use the root portion and the mould to complete the one-piece prosthesis shaping the crown potion.

In yet another embodiment, a prosthesis is segmented and such segments are fabricated using different manufacturing technologies. FIG. 45 shows the process steps of receiving design data of a prosthesis in STL format (step E), separating portions in a computer aided design (CAD) process (step X and Y), deriving computer numerical control (CNC) data and utilizing computer aided manufacturing (CAM) machinery, for example, high-speed milling/grinding machines (step I) to fabricate the respective portions (step Z and AA) in response to the CNC data. The separated portions are combined to build the prosthesis (step BB).

A specific implementation of the processes of FIG. 45 is described hereinafter: A first segmented design portion, for example, the crown portion of the prosthesis (step X) is not fabricated directly. Rather an inverse shape (for example, the negative representation of the crown shape) is cut (step I) to build a separate work piece, for example, a mould (step Z). The second segmented design portion (step Y), for example, the root portion of the prosthesis, is cut as a positive representation is cut from a workpiece (for example, consisting of zirconium oxide) (step I) to build a portion of the prosthesis itself (step AA). The positive part of the prosthesis (e.g., the root portion) is combined with the negative representation (e.g., the mould carrying the inverse crown shape) to fabricate the missing portion of the prosthesis according to the first segmented design portion (step BB). In a more particular implementation, for example, the mould "Z" is made of a transparent material (acryl glass, polymethyl-methacrylate), prepared with a separating layer (silicone spray), filled with nano-composite usually used for crown restorations (BISICO, Germany), the root portion "AA" is placed in the designed position and inclination to conform to the overall design of the prosthesis and the composite is cured in a UV-light chamber widely used in dental laboratories (step BB).

Figure 46:
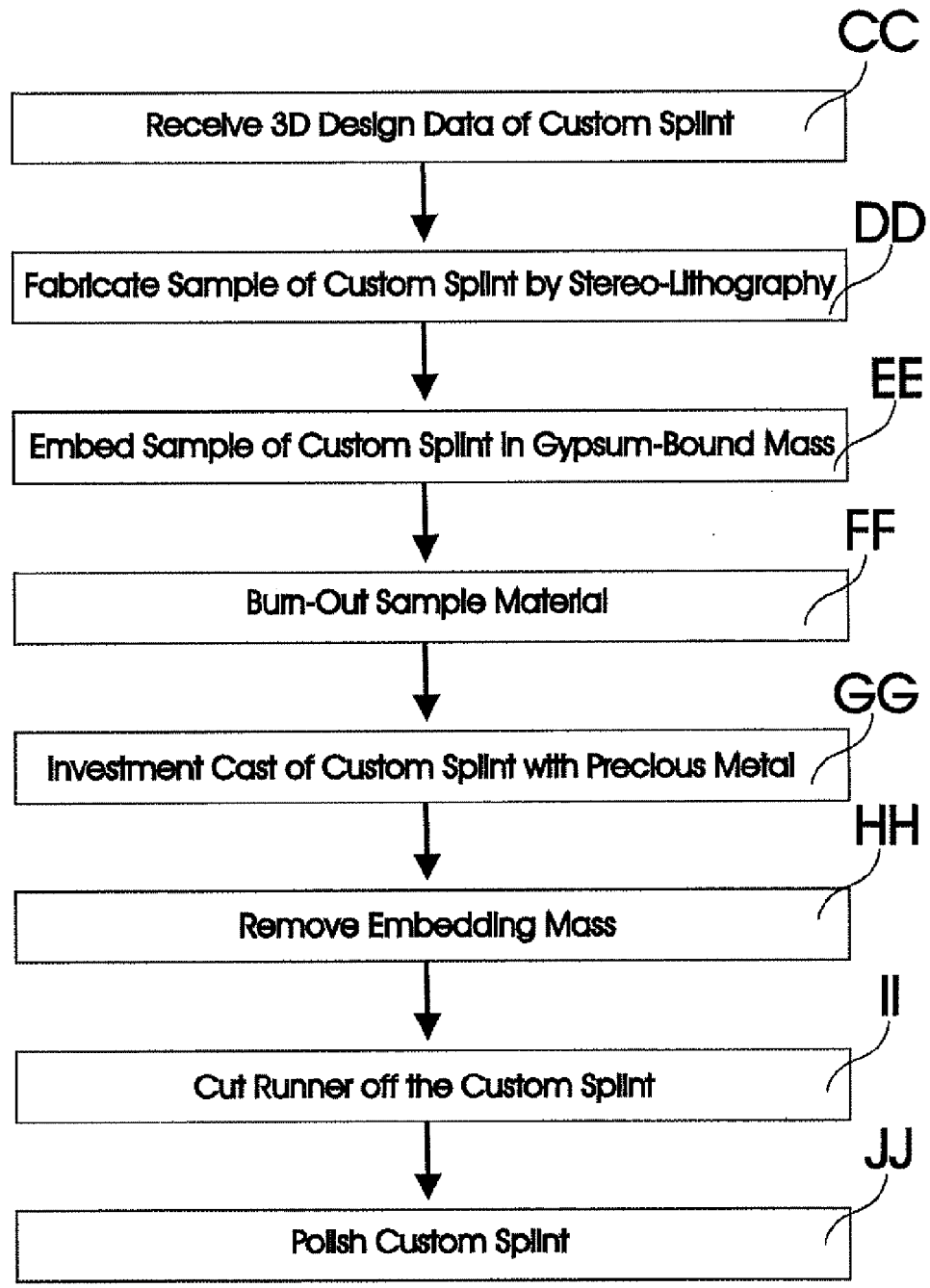
FIG. 46 shows the process steps of fabricating the custom splint from design data, and fabricating a model of the splint by rapid prototyping, build a mould around the splint, burning out the model and cast the splint by investment casting.

In another embodiment, the custom splint is fabricated in an indirect method for example, by lost-wax investment casting. FIG. 46 shows the process steps of fabricating the custom splint from design data, and fabricating a model of the splint by rapid prototyping, building a mould around the splint, burning out the model and casting the splint by investment casting. As shown in FIG. 46, the process starts with receiving the 3D design data of a custom splint (step CC), then a sample part of the custom splint is fabricated using stereo-lithography conforming to the design data (step DD). The sample part is embedded (step EE) in, for example, a gypsum-bound investment material (like Cera Fina, Whip Mix, U.S.A.). The investment mould is heated and the material of the sample part is burnt out (step FF). The mould filled by vacuum or centrifugal casting with liquid precious alloy (for example, Argenco 42 Type IV extra hard, The Argon Corporation, U.S.A.—step GG), and the embedding mass is removed (step HH). The casting runner is cut from the custom splint (step II), and the custom split is polished and prepared for bonding (step JJ). It should be noted that while FIG. 44 contemplates possible interaction with an operator, one skilled in the art would readily appreciate that certain steps can be combined, or further differentiated, and that this functionality may be partially or fully automated. Alternatively to the precious metal, the investment casting can be done with stainless steel or other suitable non-precious dental alloy known to those skilled in the art.

In yet another embodiment, the custom splint is perforated or prepared with retention features on the bonding surface (like a mesh) for better light curing capabilities and better bonding strength.

Figure 47:
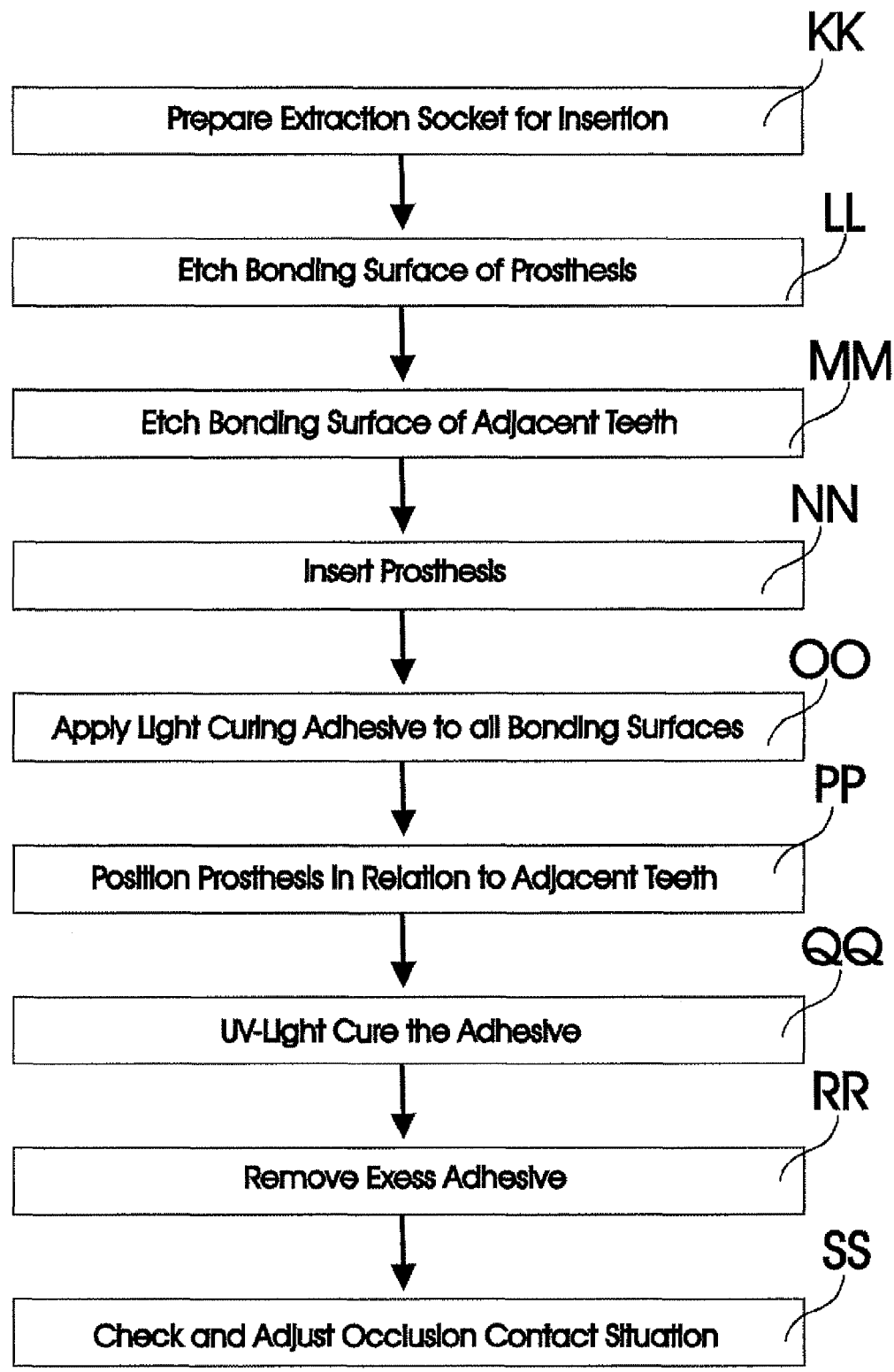
FIG. 47 shows the process steps of clinically inserting a one-piece prosthesis into an extraction socket, positioning the prosthesis in relation to the adjacent teeth with the custom splint and fixating the prosthesis in relation to the adjacent dental structure with adhesive means.

In another embodiment, the clinical process integrating the prosthesis is performed as shown in FIG. 47. The process begins by preparing the extraction socket for insertion, which may include rinsing (step KK), micro-etching (sandblasting) and/or etch (e.g., phosphoric acid) bonding the surface of prosthesis (step LL), micro-etching (sandblasting) and/or etch (e.g., phosphoric acid) bonding surface of the adjacent teeth or other dental structures (step MM). Once the extraction socket is prepared, the prosthesis is inserted (step NN), applying light curing adhesive to all bonding surfaces (step OO). The prosthesis is then positioned and oriented in the desired geometrical relation to the adjacent teeth or other dental anatomy of interest using the custom splint as a positioning aid or guide (step PP). The prosthesis and the splint are held firmly in position while the adhesive is light cured with a dental UV-light curing device (step QQ) in order to fixate the prosthesis in its desired position. Excess adhesive is removed (step RR), and a final check and adjust—if necessary—of the occlusion and articulation of the patient in respect to the contact situation of the prosthesis to the teeth or other dental structures of the opponent arch is performed (step SS).

The immediate implantation of a manufactured prosthesis designed and fabricated based on in-vivo imaging data (made prior to the extraction of one or more tooth/teeth of interest) directly after extraction may be challenged by non-healthy developments of bone or soft tissue in the extraction cavity. FIG. 48 shows the process steps of clinically preparing an extraction socket by removing decayed soft tissue (26000) and/or decayed bone (25000) with a laser technology based device (27000). The high water content of decayed structures is more absorbent for the laser light energy than healthy structures so that the decayed areas can be easily removed without serious collateral damage of adjacent healthy structures of the dental anatomy. The healing process is this way combined with the integration process of the prosthesis. Negative side effects of bone resorption are reduced by the immediate integration of a prosthesis according to an embodiment of this invention. The immediate implementation can be combined with both prosthesis configured for osseointegration and with prosthesis configured for periodontal integration.

In yet another embodiment, the healing and integration of a prosthesis is facilitated after insertion by using ultrasonic or other vibrations applied to the prosthesis by special dental devices.

Figure 49:
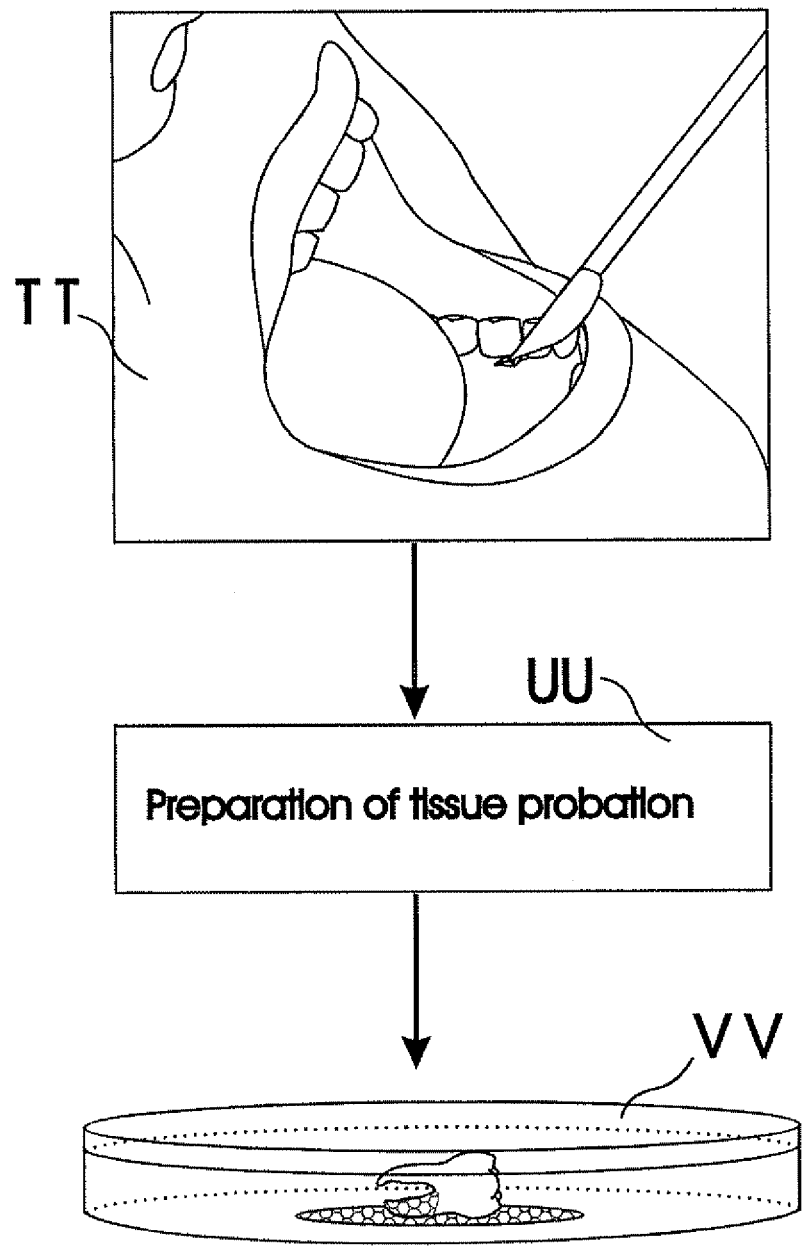
FIG. 49 shows the process steps of manufacturing a prosthesis where autologous biological tooth or tissue material is taken from a patient to be used in an tissue engineering process to configure the root portion of the prosthesis for periodontal integration.
Figure 50:
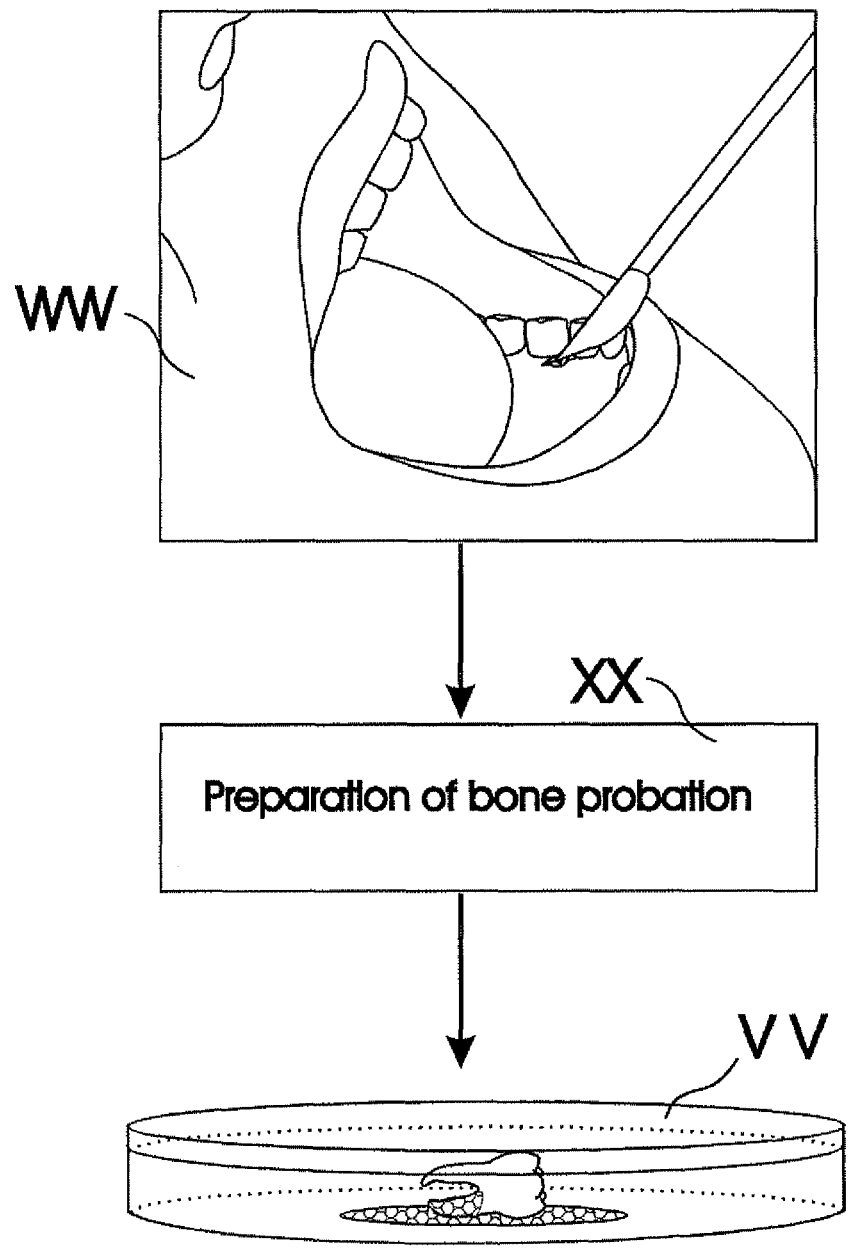
FIG. 50 shows the process steps of manufacturing a prosthesis where autologous biological bone material is taken from a patient to be used in an tissue engineering process to configure the root portion of the prosthesis for osseointegration.

The integration of the all prosthesis described herein can be facilitated and actually accelerated by techniques of surface coating based on tissue engineering. FIG. 49 shows the process steps of taking autologous soft tissue cells from the patient (step TT), culturing such soft tissue cells in an in-vitro assay system (step UU), and apply such cells with or without other tissue engineering materials to the root portion of the prosthesis (step VV). FIG. 50 shows the process steps of taking autologous bone cells from the patient (step TT), culturing such soft bone cells in an in-vitro assay system (step XX), and apply such cells with or without other tissue engineering materials to the root portion of the prosthesis (step VV). In both aforementioned scenarios the soft-tissue or bone structures are taken with a sharp instrument (for example, an exenteration scoop like a Chalazion curette). Other exenteration techniques may apply.

In another embodiment, human periodontal ligament (HPDL) fibroblasts are used and a prosthesis according to other embodiments of the invention is placed in tissue culture clusters, an amount of 1 ml of HPDL fibroblast cell suspension is placed over the root portion of the prosthesis and then placed into an incubator at 37 degree C. and 100% humidity for 72 hours. With that the cells of HPDL fibroblast are extending and attaching firmly to the prosthesis surface by cytoplasmic extension of the lamellipodia and microvilli to extend into porous (micro) surface structures.

In yet another embodiment, stem cells can be used to produce HPDL fibroblast or other acellular and cellular structures of the human dental anatomy (like acellular and cellular cementum, which is mineralized tissue covering the root dentin that serves to anchor periodontal ligament fibers, cementoblast, which are cells found on the surface of cementum being responsible for its synthesis).

Alternatively, to the aforementioned use of autologous material, human allogenic bone, root or tissue substances can be used. Alternatively, to the use of human bio material tooth, animal-derived bone or tissue material, for example, bovine cells or even synthetic materials can be used for in the various process steps of tissue engineering.

In yet another embodiment, the tissue engineering techniques include the coating of the root portion(s) of the prosthesis with collagen incorporating growth factor substance, for example, platelet-derived growth factor (PDGF).

The aforementioned tissue engineering technologies may employ in the aforementioned context living cells of various kinds as engineering materials, like autologous cells, which are obtained from the same individual to which they will be reimplanted, mouse embryonic stem cells, allogenic cells which come from the body of a donor of the same species, xenogenic cells which are isolated from individuals of another species, syngeneic or isogenic cells which are isolated from genetically identical organisms, such as twins, clones, or highly inbred research animal models, primary cells from an organism, secondary cells from a cell bank, and adult stem cells. In this context, tissue engineering shall also include the use of artificial structures capable of supporting three-dimensional tissue formation, called scaffolds, of various natural and synthetic, biodegradable and permanent materials (for example, collagen and aliphatic polyesters), on which cells are generally implanted or 'seeded' into to allow cell attachment and migration, to deliver and retain cells and biochemical factors, to enable diffusion of vital cell nutrients and expressed products, or to exert certain mechanical and biological influences to modify the behavior of the cell phase, or any combination thereof.

Figure 3:
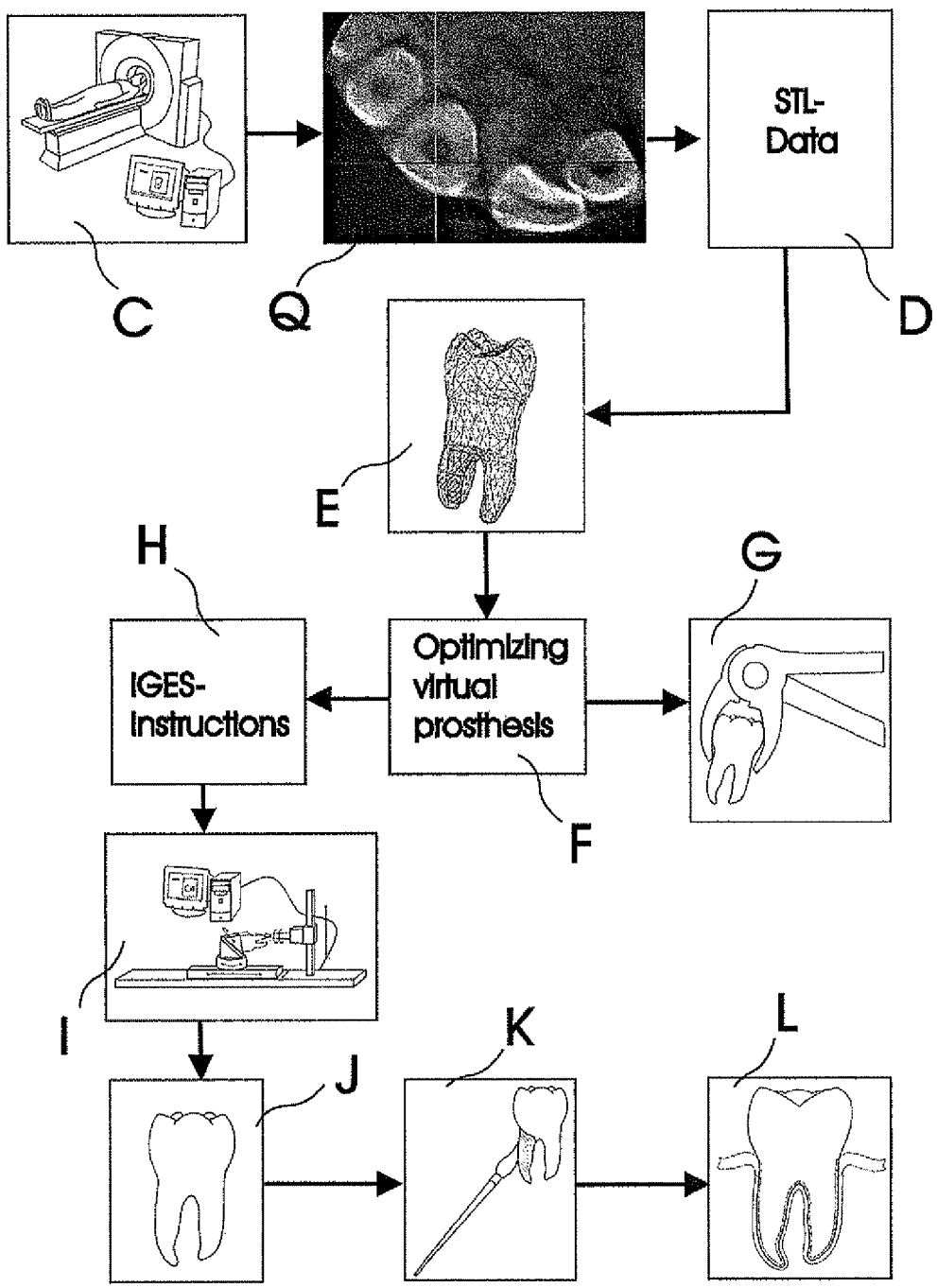
FIG. 3 shows the process steps of intra-orally acquiring three-dimensional data of a human tooth, fabricating an artificial copy, extracting the natural tooth and replacing it with the artificial copy according to an embodiment of the invention.
Figure 4:
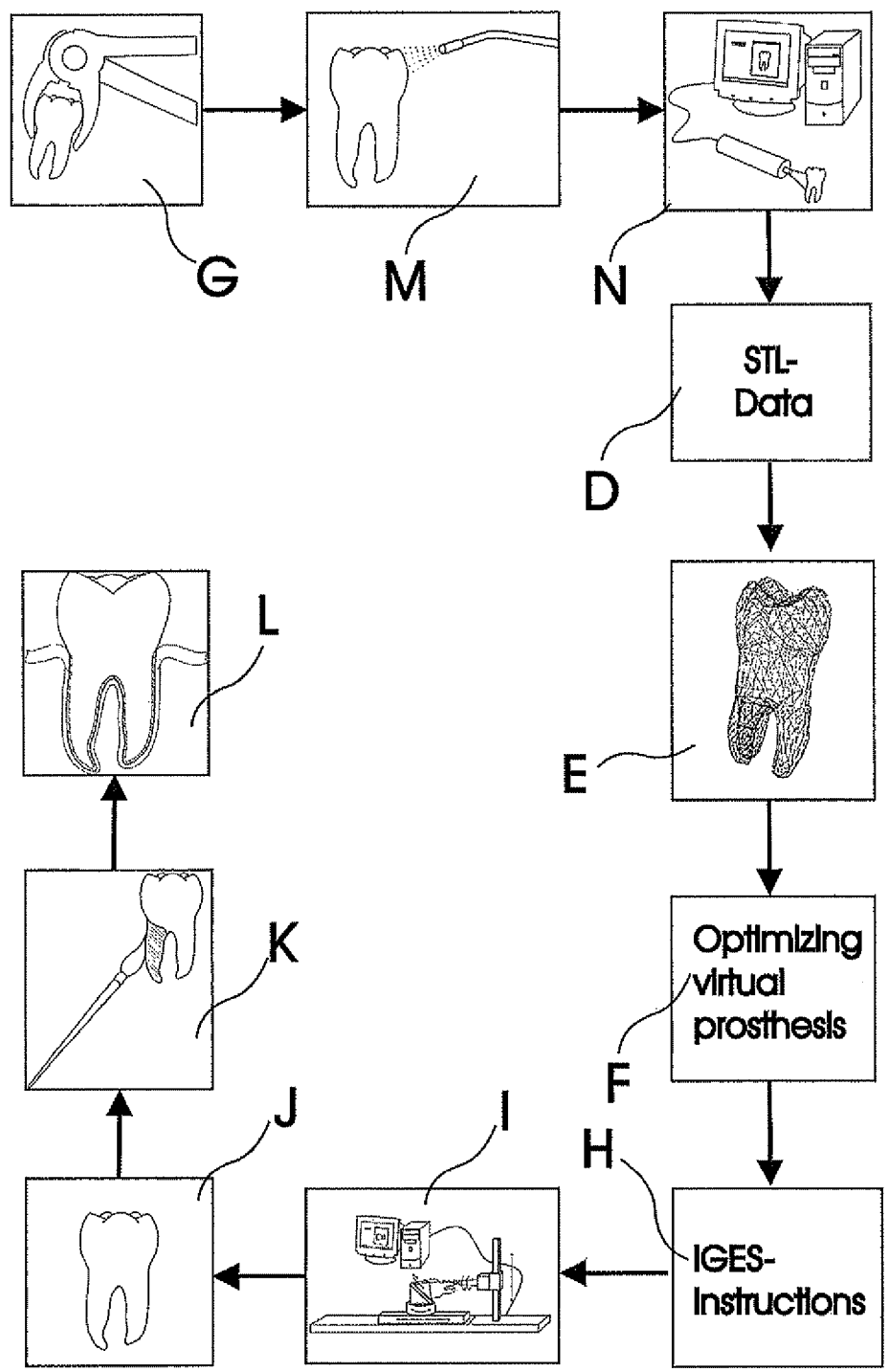
FIG. 4 shows the process steps of extracting the natural tooth, extra-orally acquiring three-dimensional data of that tooth, fabricating an artificial copy and inserting the copy into the socket of the natural tooth according to an embodiment of the invention.
Figure 51:
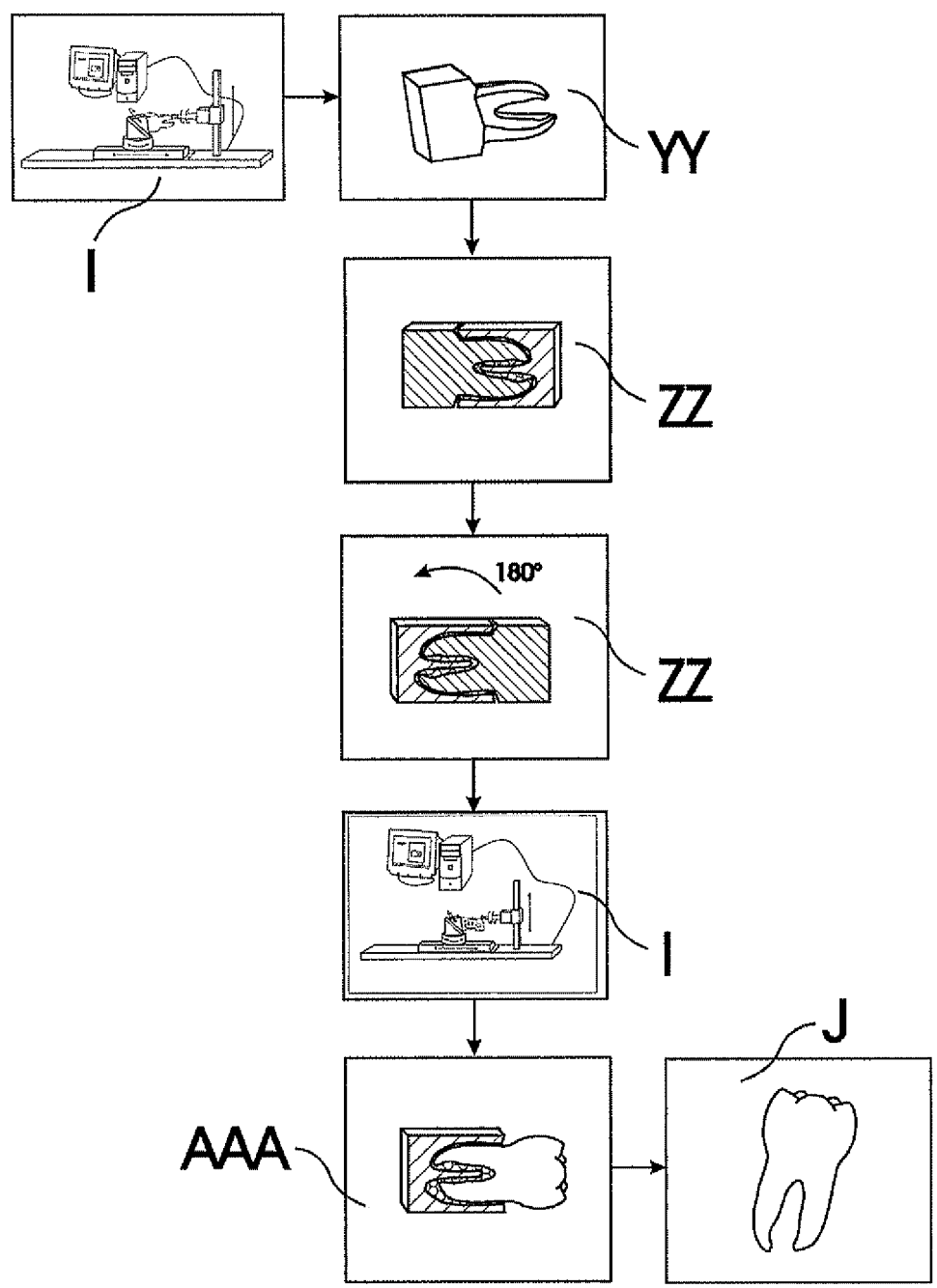
FIG. 51 shows the process steps of fabricating a one-piece prosthesis.

Several figures and several process steps described therein show a prosthesis or parts thereof (configured for example, as a single tooth prosthesis) being manufactured and shaped from all sides (for example, FIG. 1 part 200, FIG. 3 step J, FIG. 4 step J, FIG. 5 step J, FIGS. 6, 7, 8, 9, 10, 11, 12, FIGS. 13/15/16 part 12030 and part 12000, FIG. 17 part 900, FIG. 18 part 9040, FIG. 19 part 9090 and part 12050, FIG. 21 part 16000, FIG. 22, FIG. 31, FIG. 34, FIGS. 35/36 part 12030 and part 12000, FIG. 39 part 200, FIG. 40 part 400, FIG. 41 part 200 and part 200 including 22000, FIG. 42 part 200 and part 200 including 23000, FIG. 43 part 400 and part 24000, FIG. 44 step J and step U, FIG. 45 step I, Z and step M, FIG. 46 step DD). FIG. 51 outlines the process steps. After a design of such prosthesis is obtained and computer numerical control (CNC) data are derived and converted for example, into the IGES format and transferred to a CAM system for fabricating the prosthesis (step I), the prosthesis is shaped, for example, in regards to its root portion by milling one side of the workpiece (with the result shown in step YY). The side of the workpiece being already shaped will be temporarily embedded in adhesive materials (step ZZ) turned (step ZZ') and fed, positioned, orientated and clamped again into the CAM system (step I) to be shaped, for example, in regards to its crown portion by milling the opponent side to the aforementioned one side (with the result as shown in step AAA). After dissolving or otherwise removing the adhesive (shown in step ZZ and AAA) the all sides shaped workpiece is ready for use or for the following process steps of surface polishing, surface coating by, for example, plasma technologies, and tissue engineering. Drug releasing surfaces can be applied or porous surfaces may be loaded with growth hormones, proteins, antibiotic or other substances. It should be noted that while FIG. 51 contemplates possibly interaction with an operator, one skilled in the art would readily appreciate that this functionality may be fully automated.

Skiba discloses in U.S. Pat. Ser. No. 7,813,806, which is incorporated herein by reference, a surface coating and pattern of spaced dissimilar materials, whereby the pattern is designed to spontaneously produce electrical surface currents when brought into contact with an electrically conducting solution, i.e., body electrolytes, whereby the currents reducing infection and contamination. For example, when a single mass of silver ink is spaced from a single mass of zinc ink, a single voltaic cell is created when an electrolytic solution electrically connects the masses. In an exemplary embodiment, at least a root portion of the dental prosthesis is coated with at least one dot of each of at least two dissimilar materials. Such dots, have, for example, a diameter of 1 mm and an average distance between its centers of 1.5 to 3 mm, and are painted on by bubble jet printing or by other means, e.g., by hand painting. The materials are bio-compatible and, for example, even resorbable over time, so that the current producing effect when deployed for a period of time enhances the integration and would healing.

For achieving a certain solidity and resistance of the dental prosthesis, it is important to find a method for applying a finishing process to the body or a component of a dental prosthesis (200). It is known from US 2004/0168610 A1 that companies in the dental industry, for example, Metoxit, supply ceramic blocks treated by a hot isostatic process. However, it has not been recognized until now by the inventors that dental implants, abutments, prostheses or parts thereof are individualized in its three-dimensional shape prior to a hot isostatic pressing.

Figure 52:
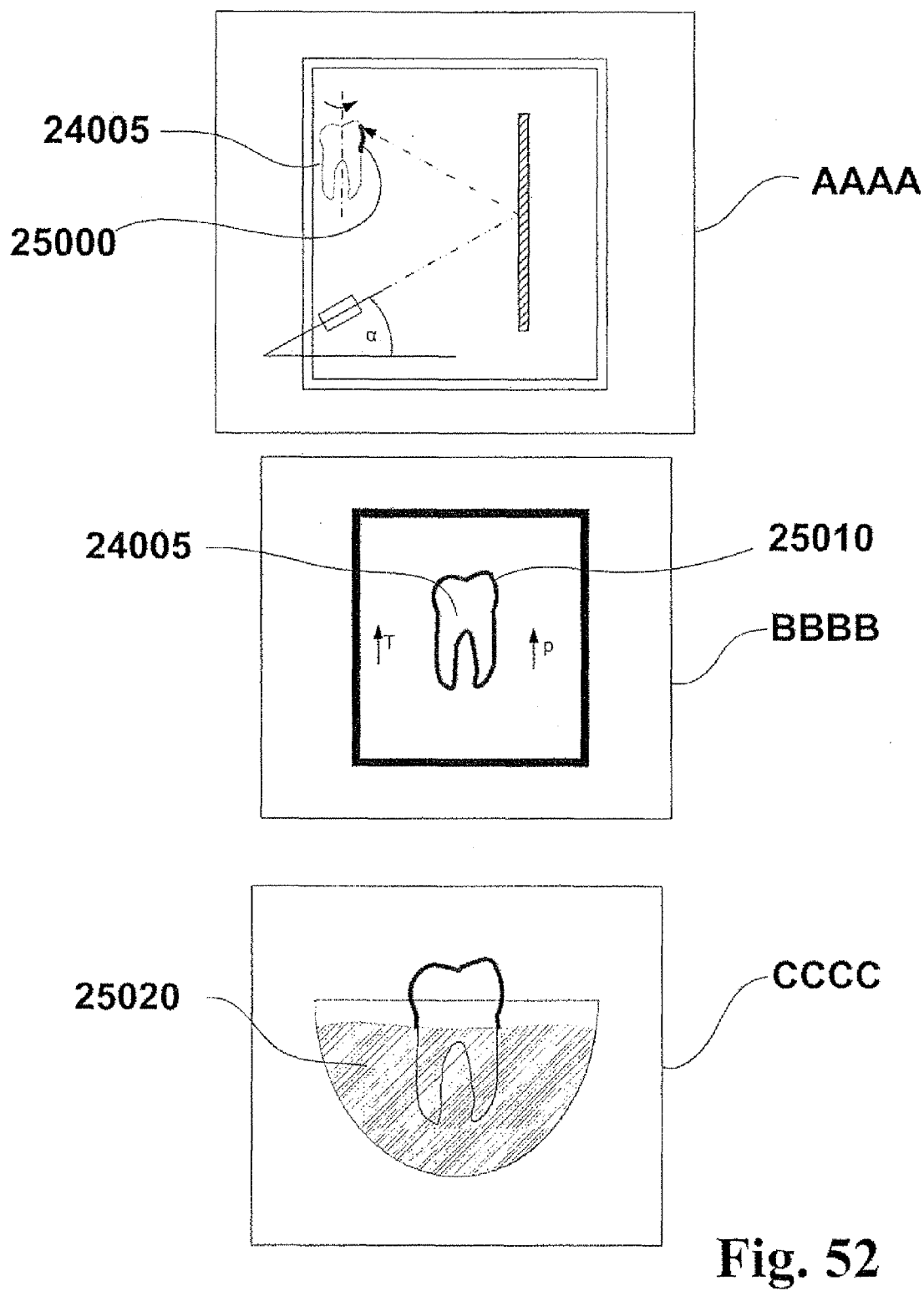
FIG. 52 shows the customized hot isostatic pressing method.

In an exemplary embodiment, the process depicted in FIG. 52 reflects the hot isostatic pressing of a customized dental prosthesis or its components. In the first step (AAAA), the body or a component of the dental implant (24005) is spattered with a metallic material (25000). Vacuum may be applied in the process of spattering. In a second step (BBBB), a hot isostatic pressing process is applied to the body or component (24005) with the coating (25010). Thereby, certain cracks, flaws and imperfections of the dental prosthesis body are compressed and eliminated. This leads to a reduction of porosity of the ceramic material and allows to compress the ceramic material close to its theoretical density. The pressures are preferred of approx. 100 MPa (but may range up to 300 MPa); temperatures of approx. 1,400 degrees Celsius (but may range up to 2,200 degrees Celsius). The hot isostatic pressing process uses inert gas such as Argon gas as compression media. In a further step (CCCC), the metallic coating (25000) is removed from the cooled-down ceramic body or component (24005) of the dental prosthesis. The removal of the coating (25000) is achieved by the use of an etching process in which the coated body is placed in an acidic liquid (25020) to totally remove the metallic coating. In an alternative embodiment, the aforementioned process steps are carried out on a body that consists of two or more parts. Those parts may have different materials. The hot isostatic pressing process will then facilitate an integration in the event of joints between similar or identical materials or a diffusion bonding in the event of joints between different materials. It is alternatively possible to pre-sinter the ceramic components gas-tight prior to the hot isostatic pressing in order to avoid process step (AAAA) and (CCCC).

Figure 53:
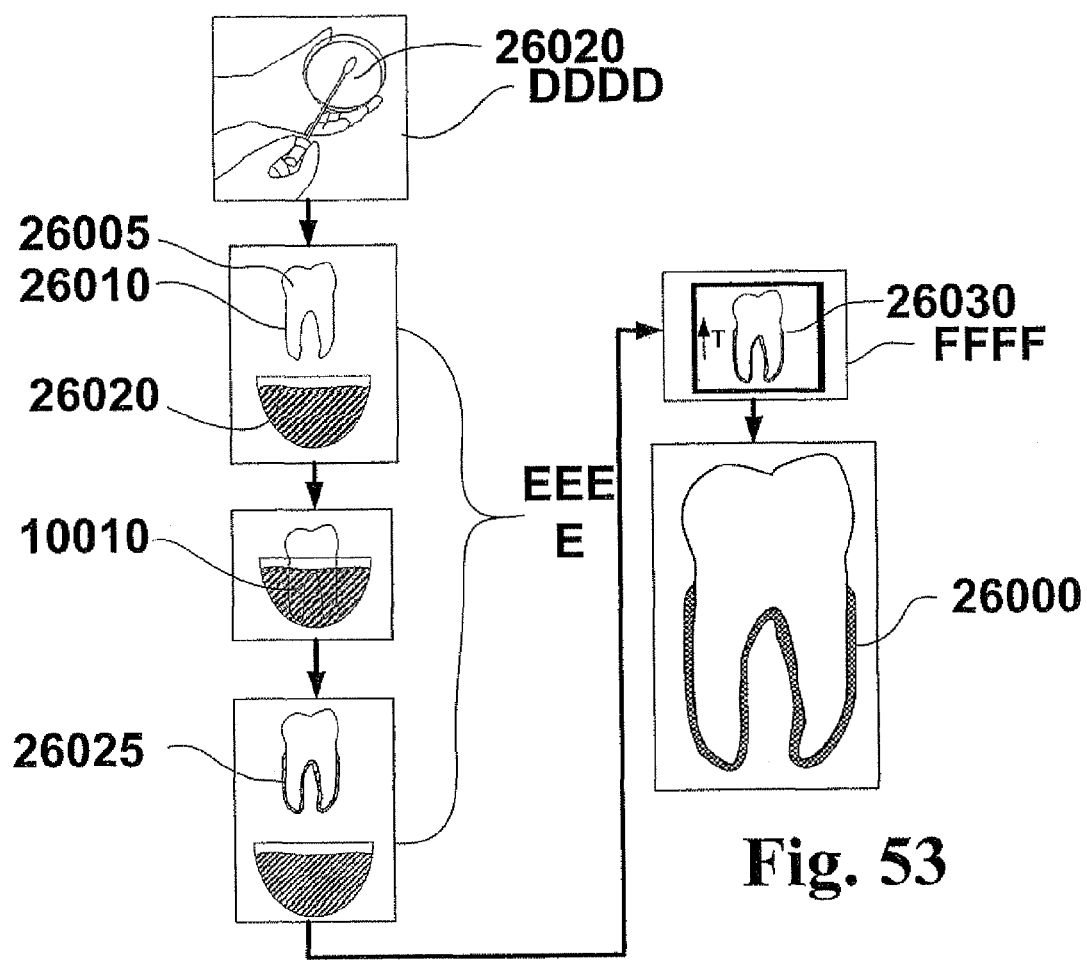
FIG. 53 shows the process of coating the one-piece prosthesis with a porous ceramic.

In a further embodiment, as shown in FIG. 53, a ceramic porous coating (26000) is attached onto the outer surface (26010) of the root portion body or a component of a dental prosthesis (26005). A method and an arrangement for attaching a ceramic porous coating to a dental prosthesis is known from US 2008/0213725 A1 in which the company Noble Biocare describes the coating of a dental prosthesis with a ceramic slurry. However, it has not been recognized until now by the present inventors that similar surface coating methods can be applied to dental implants, prosthesis, or parts thereof after the surfaces are designed and three-dimensionally shaped for a pre-identified patient. In the first step (DDDD) depicted in FIG. 53, a ceramic slurry (26020) is mixed comprising zirconia particles and wax particles or plastic particles such as Polyethylene powder, In the next method step (EEEE), the root portion body (10010) is dunked into the ceramic slurry (26020) and pulled out with, e.g., a constant moving velocity to receive a substantial uniform coating.

After pulling out the root portion body from the ceramic slurry (26020), a ceramic slurry coating (26025) is attached on the outer surface (26010) of the root portion body. In a further step (FFFF), the whole assembly (26030) is first dried in an environment with increased temperature. Then, the wax particles or Polyethylene-powder is removed from the ceramic coating (26025) and the coating particles are sintered together and connected by sintering with the body material by applying high temperature to the body. In another step, the connection between the root portion body and the ceramic coating is achieved by sintering both parts together and thereby forming one part. Thereby, a porous coating (26000) is produced with a surface and scaffold that attract biological tissue to form the desired periodontal integration of the proposed dental implant into the patient's alveolus.

Figure 54:
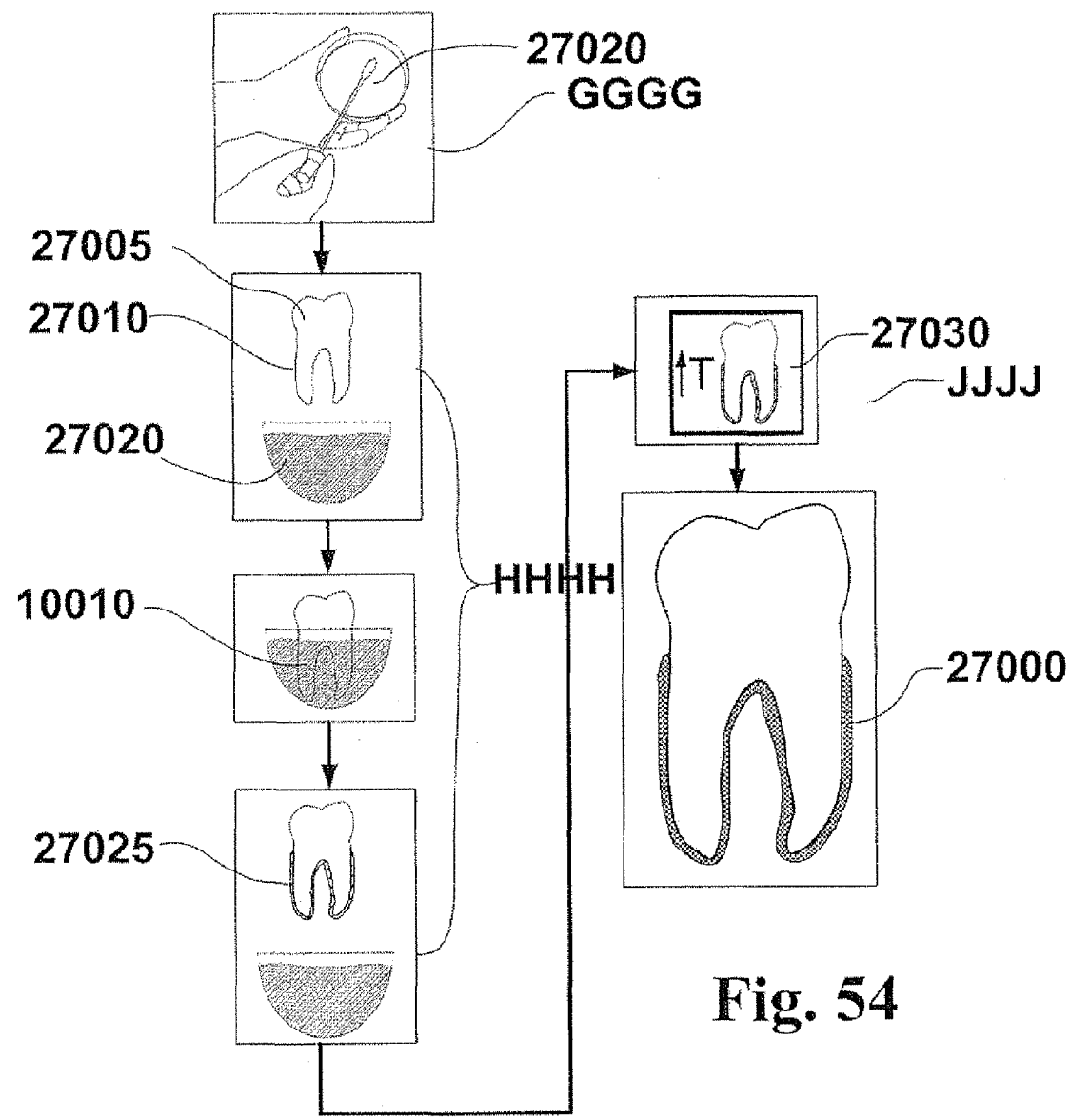
FIG. 54 shows the process of coating the one-piece prosthesis with a hydroxyapatite-layer.
Figure 55:
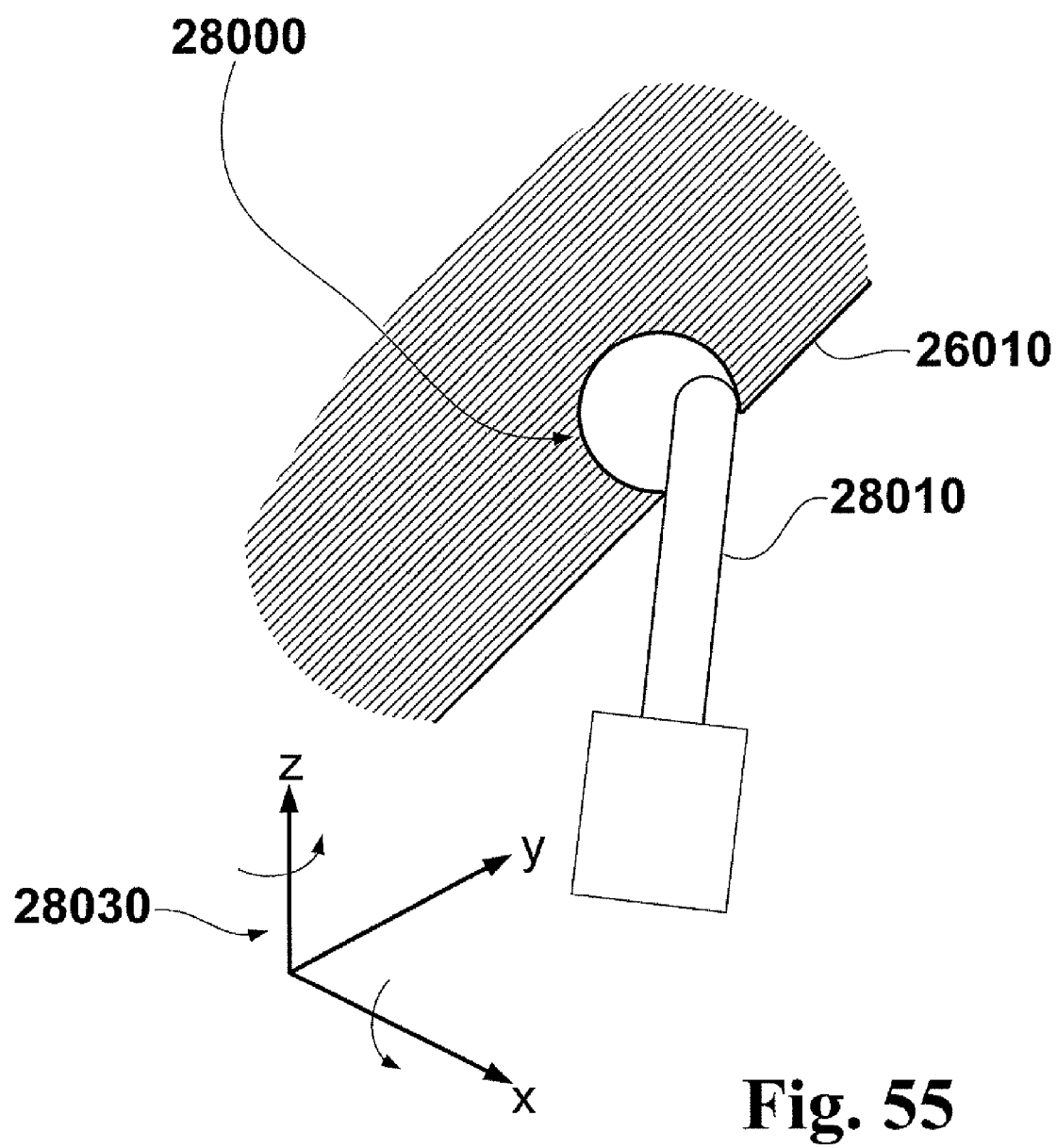
FIG. 55 shows a method for creating a porous outer surface on the root body portion of the one-piece dental prosthesis by utilizing pico/femto-laser pulses.

Another embodiment is shown in FIG. 54. Herein, the outer surface of the root body portion (27010) of the body or a component of a dental prosthesis dental prosthesis (27005) is infiltrated with an alcoholic Hydroxylapatite-suspension (27020). In the first step (GGGG), the Hydroxylapatite-suspension (27020) is mixed composing Hydroxylapatite, ethanol, Polyvinylpyrrolidon as a binder and Dolapix CE as a dispersant. In the second step (HHHH), the root portion body (27010) is dunked into the Hydroxylapatite-suspension and pulled out again. Thereby, the Hydroxylapatite-suspension (27025) adhesively attaches to the root portion body. After applying a burning procedure (JJJJ) on the whole body (27030), the outer surface is coated with a biocompatible Hydroxylapatite-layer (27000). Thereby, a coating is produced with a surface and scaffold which attracts biological tissue to form the desired periodontal integration of the proposed dental implant into the patient's alveolus In a further embodiment as depicted in FIG. 55, the porous outer surface (28000) in the area of the root portion body (26010) of the dental prosthesis is created by applying laser light pulses (28010) to the outer surface (26010) of the root portion body. Such light pulses have a pulse-duration in the pico-or femto-seconds range. Thereby, high energy pulses are created which are able to break apart parts of the ceramic body and produce small cavities. Bärsch suggested in Quintessenz Zahntech 2009 35(10): 1322-1332, the treatment of zirconia implants with femto-second laser pulses for enhancing the adherence. However, it has not been recognized until now by the present inventors, that the root portion of dental prostheses can be contoured individually for a pre-identified patient by laser shaping. The laser shaping can be used to polish certain surface portion, e.g., in the transgingival portion of the prosthesis, and to contrarily create a roughness, e.g., in the root portion to integrate with tissue, including a porous surface condition. In a further embodiment, single laser shaped cavities create the porous outer surface on the ceramic body. The laser pulses are emitted from a laser entity being able to move in three translation dimensions and two rotation dimensions (28030). Such a setting is often called 5-axis laser. In yet another embodiment, 5-axis laser (28010) is used to shape the individual three-dimensional contour of the prosthesis, at least partially.

Figure 56:
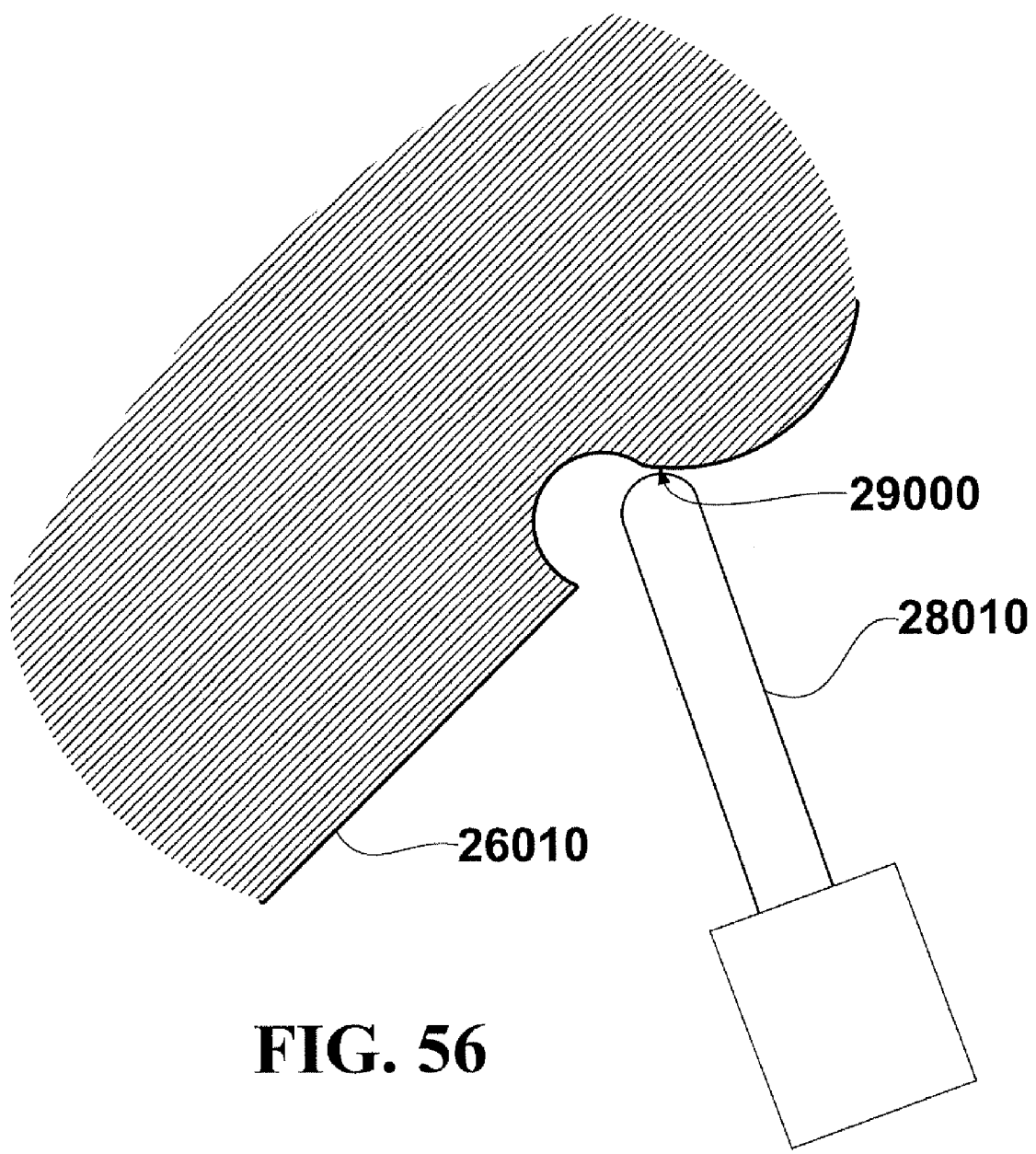
FIG. 56 shows a method for creating rounded edges in the porous outer surface on the root body portion of the one-piece dental prosthesis.

In an embodiment depicted in FIG. 56, the pico- or femto-laser pulses (28010) can also be utilized to create rounded edges (29000) on the porous outer surface on the root portion (26010). Such rounded edges are of special interest since they promote the biocompatibility and lead to an environment attracting biological tissue.

Figure 57:
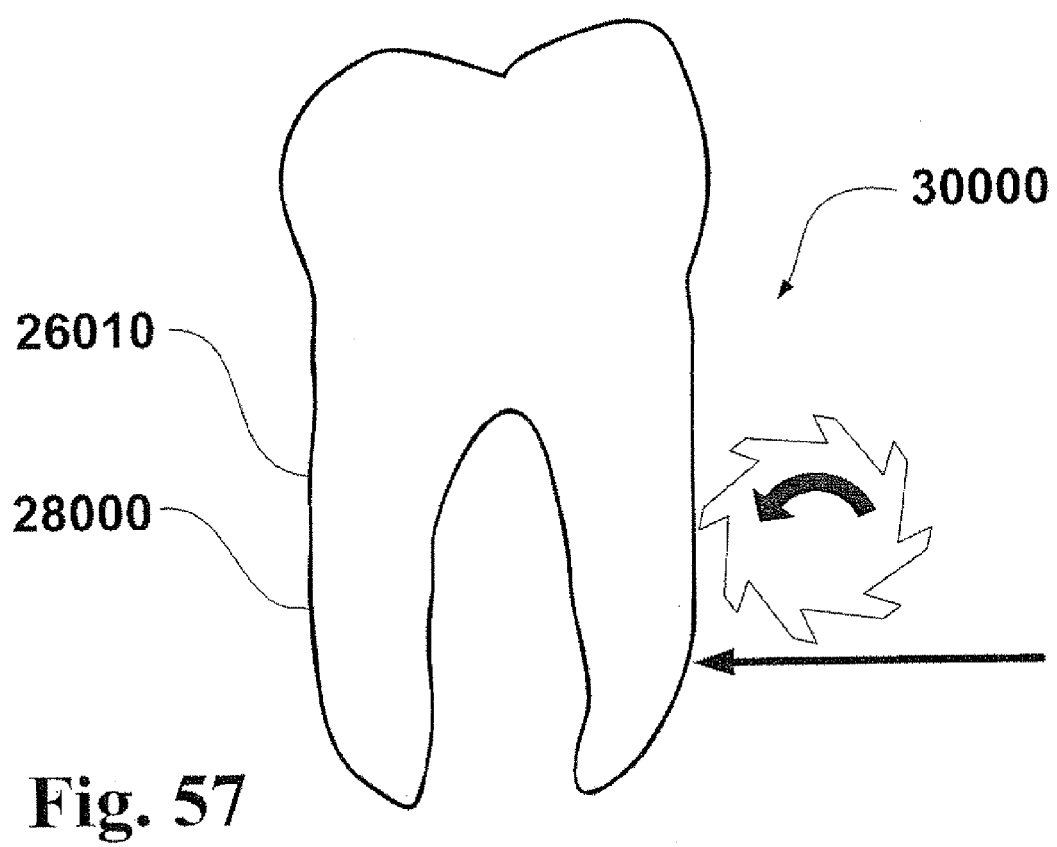
FIG. 57 shows a method for creating a porous outer surface on the root body portion of the one-piece dental prosthesis by milling.

In a further embodiment of the present invention shown in FIG. 57, a porous outer surface (28000) in the area of the root portion body (26010) of a dental prosthesis or implant is created by a CNC milling or a CNC driven sinker erosive process (30000).

Figure 58:
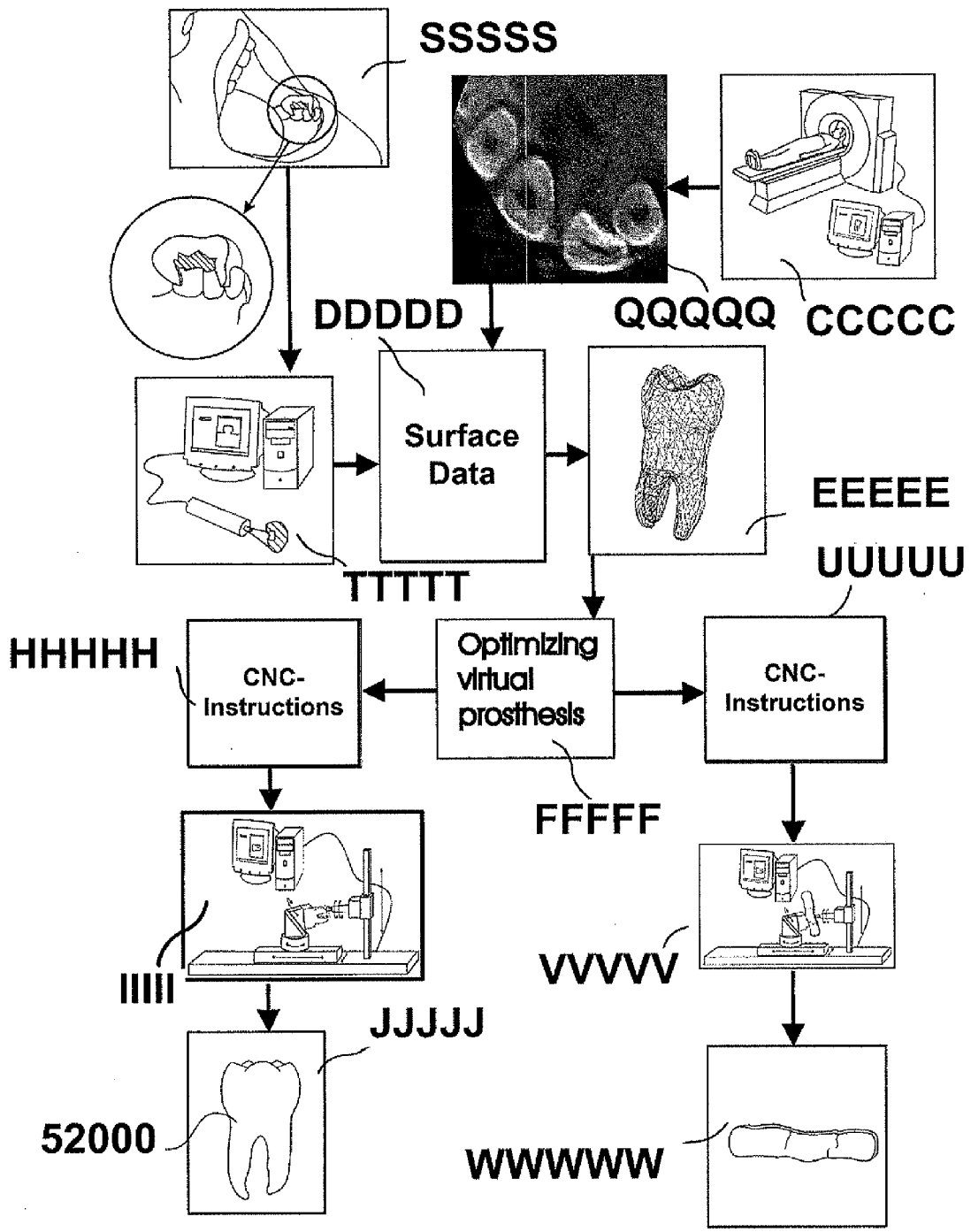
FIG. 58 shows an overall fabrication method of the prosthesis and its dedicated parts, including a splint.

In another embodiment shown in FIG. 58 of the fabrication process of a prosthesis (52000) together with a splint, in a first step (SSSSS) a physical impression of the denture of the patient is taken, e.g., with silicon material. In a further step (TTTTT), the crown geometry of the patient's crown is obtained from the denture and translated to three-dimensional STL-data. Additionally, the patient's dental anatomy is imaged with a computed tomography device (CCCCC). The layered grey scale X-ray data in digitized form (QQQQQ) are analyzed and voxels as well as three-dimensional STL-data (DDDDD) are derived representing the anatomy of the patient's denture. The grey scale X-ray (QQQQQ) data can be represented in the format of the DICOM standard (DICOM: Digital Imaging and Communications in Medicine). In a further step (EEEEE), Boolean algorithms are used to generate combined data of high quality of a virtual prosthesis. The data of the virtual prosthesis are optimized (FFFFF), e.g., automatically or interactively by a technician operating the respective computer equipment. From the data of the virtual prosthesis, computer numerical control (CNC) instructions are derived. These are CNC-instructions of two kinds. Firstly, CNC-instruction are derived for fabricating the dental prosthesis in a CAM (Computer-added Manufacturing) high-speed milling/grinding machine (IIIII and JJJJJ). Moreover, CNC-instructions (UUUUU) are derived for fabricating a splint in step (VVVVV and WWWWW) that individually fits to the corresponding prosthesis.

In a further embodiment of the aforementioned fabrication process, the two steps SSSSS and TTTTT can be combined to one step. Therefore, a three-dimensional camera can be used as known from the CEREC three-dimensional camera systems provided by the Sirona Group to avoid the process (SSSSS) taking a physical impression of the dental anatomy of interest. As in the fabrication process depicted in FIG. 58, a computed tomography device is used for imaging the dental anatomy of the patient's tooth to be replaced and its adjacent teeth.

From the surface data, the CNC-instructions can also be derived for a chair side fabrication device. Such a chair side fabrication device for dental prostheses is known from the inLab MC XL milling unit which is offered by the Sirona Group. Therewith, in an exemplary embodiment of the present invention, the prosthesis and the corresponding splint can be fabricated at the dentist's site. Firstly, this is a simplification of the overall fabrication and delivery process. Especially, for dentists that have their own milling unit for fabricating crowns etc., the chair side production enhances the overall treatment process and saves time, e.g., in cases where fast replicas are needed by a patient.

Figure 59:
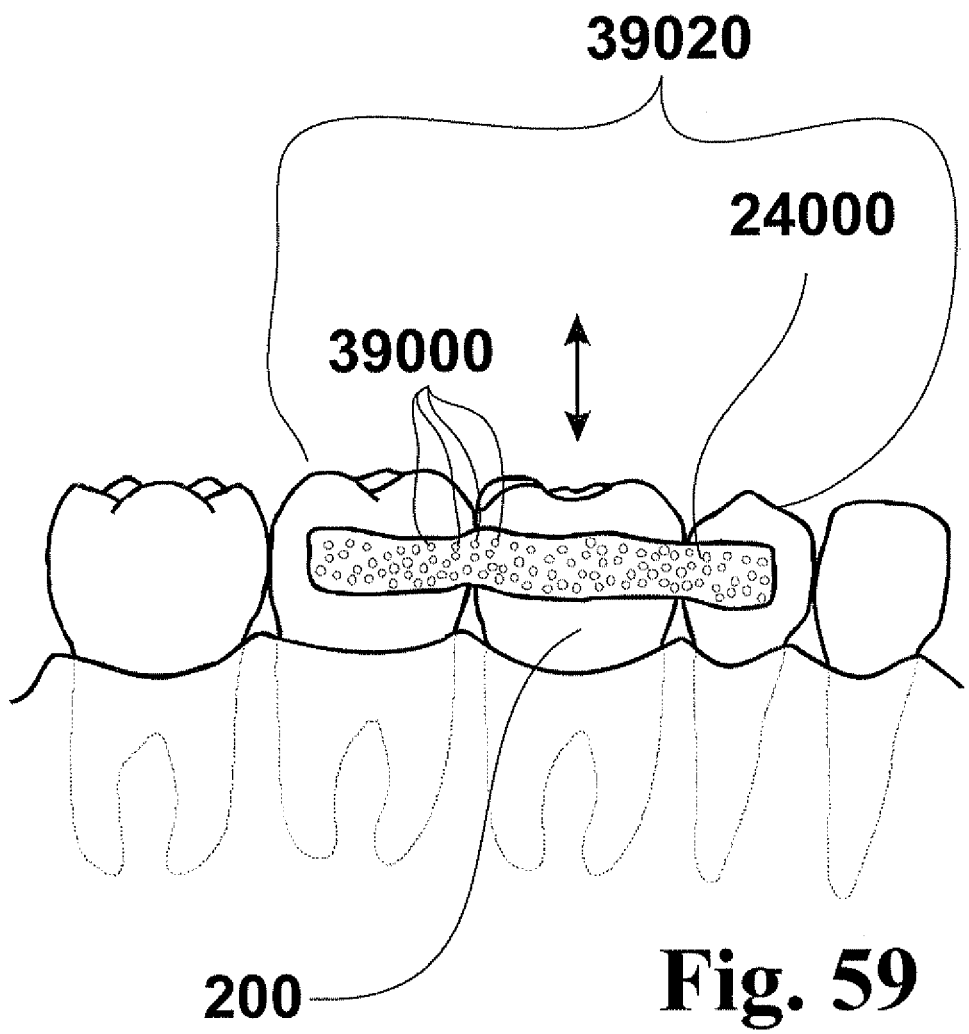
FIG. 59 shows a perforated splint comprising holes.

In a further enhancement of the present invention depicted in FIG. 59, the attachable splint (24000) provides a number of recesses (39000) formed as holes. Other methods of perforation may be used. This enhancement of the attachable splint (24000) can be useful for the adhesive material, e.g., glue, which attaches the splint to the prosthesis (200) and the adjacent teeth (39020). An adhesive that needs to attach to a smooth splint surface may not provide enough stability since no hold points are provided for the adhesive to attach to. The holes through the splint enhance the adhesive in attaching to the splint. The adhesive material can propagate into the holes or the perforations and, after having changed into solid state, provide additional mounting means between splint and prosthesis or adjacent teeth respectively.

Figure 60:
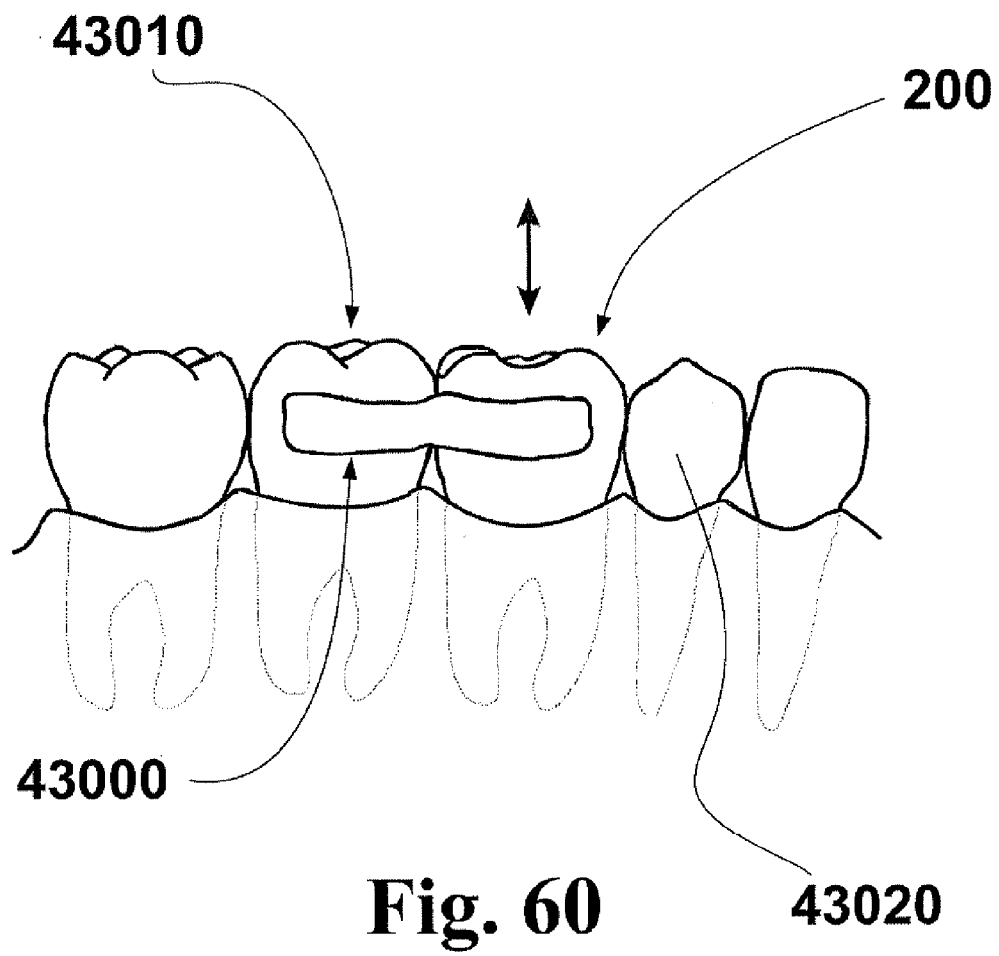
FIG. 60 shows a splint which is attached only to one of the adjacent teeth.

Another embodiment of the present invention is depicted in FIG. 60. Therein, the splint (43000) is designed in a way that it is attached to the dental prosthesis (200) and to one of the adjacent teeth (43010). Such a splint design can be useful in cases where the other adjacent tooth (43020) on the opposite side of the prosthesis (200) is not qualified for the attachment of a wing of the splint (43000).

Figure 61:
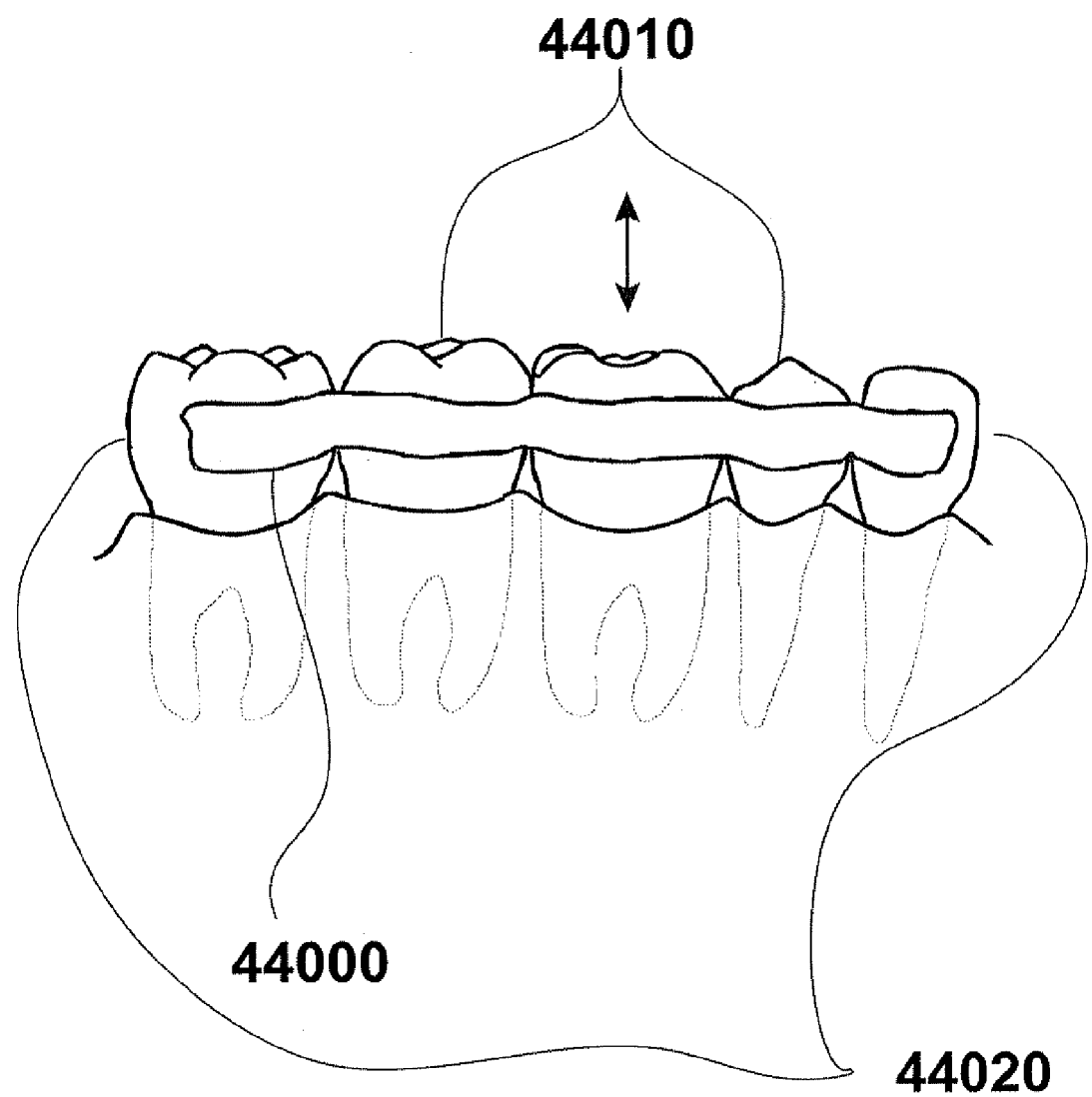
FIG. 61 shows a splint being attached to the adjacent teeth and teeth next to the adjacent teeth.

Another embodiment of the present invention is depicted in FIG. 61. This embodiment is characterized by a splint (44000) which is not only attached to the prosthesis (200) and the adjacent teeth (44010) but also to the next teeth (44020) adjacent to the adjacent teeth (44010) of the dental prosthesis (200). Such an embodiment of the splint can be useful when the two directly adjacent teeth (44010) are not qualified for providing primary stability to the prosthesis (200) via the splint, The enhanced splint, therefore, makes use of the stability of the next teeth (44020) adjacent to the adjacent teeth (44010). Any combination of the foregoing is possible to reflect limitations of the dental anatomy of interest, attaching the prosthesis to one or more adjacent teeth, on one or either side of the prosthesis.

Figure 62:
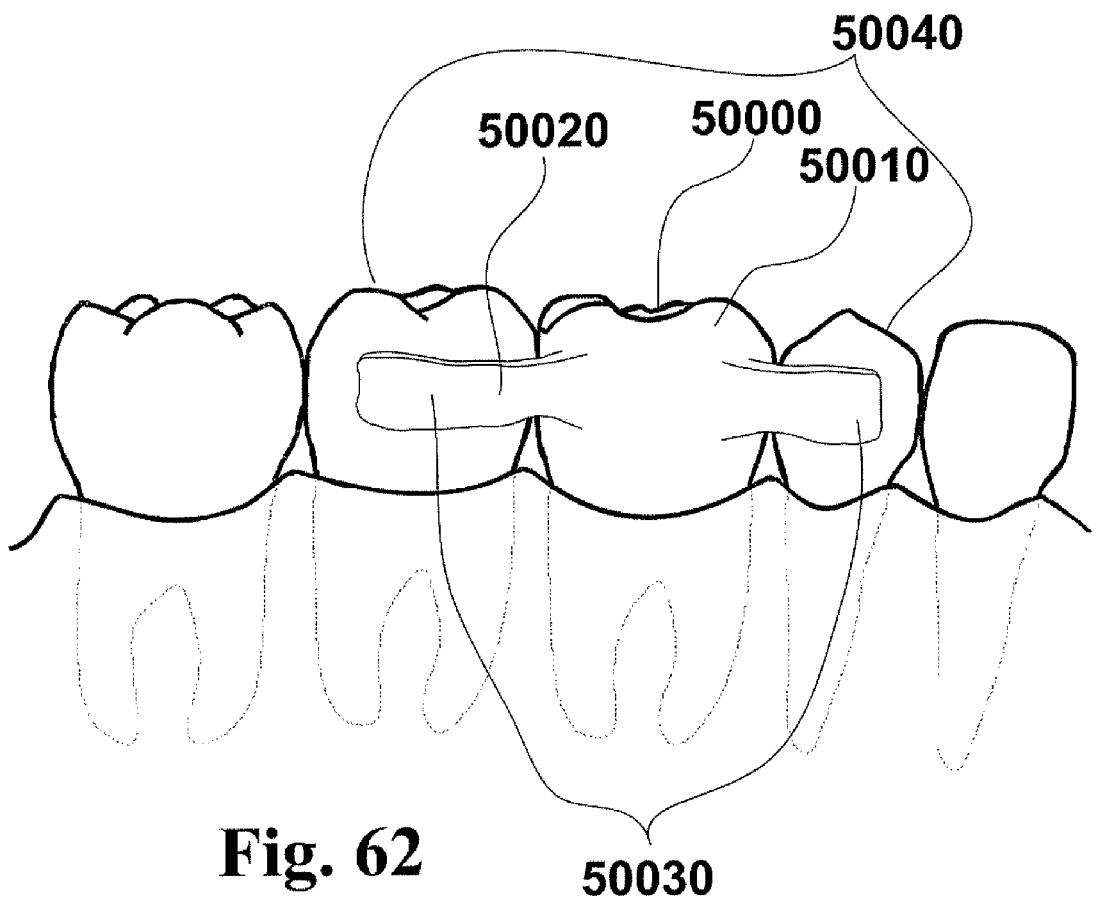
FIG. 62 shows a prosthesis with a crown portion body forming one part with a splint.

In an exemplary embodiment of the present invention, a dental prosthesis (50000) is proposed as depicted in FIG. 62. In the shown embodiment, the crown portion body (50010) and the splint (50020) form one part, i.e., the crown portion body entails wings (50030) that attach to the adjacent teeth (50040).

Figure 63:
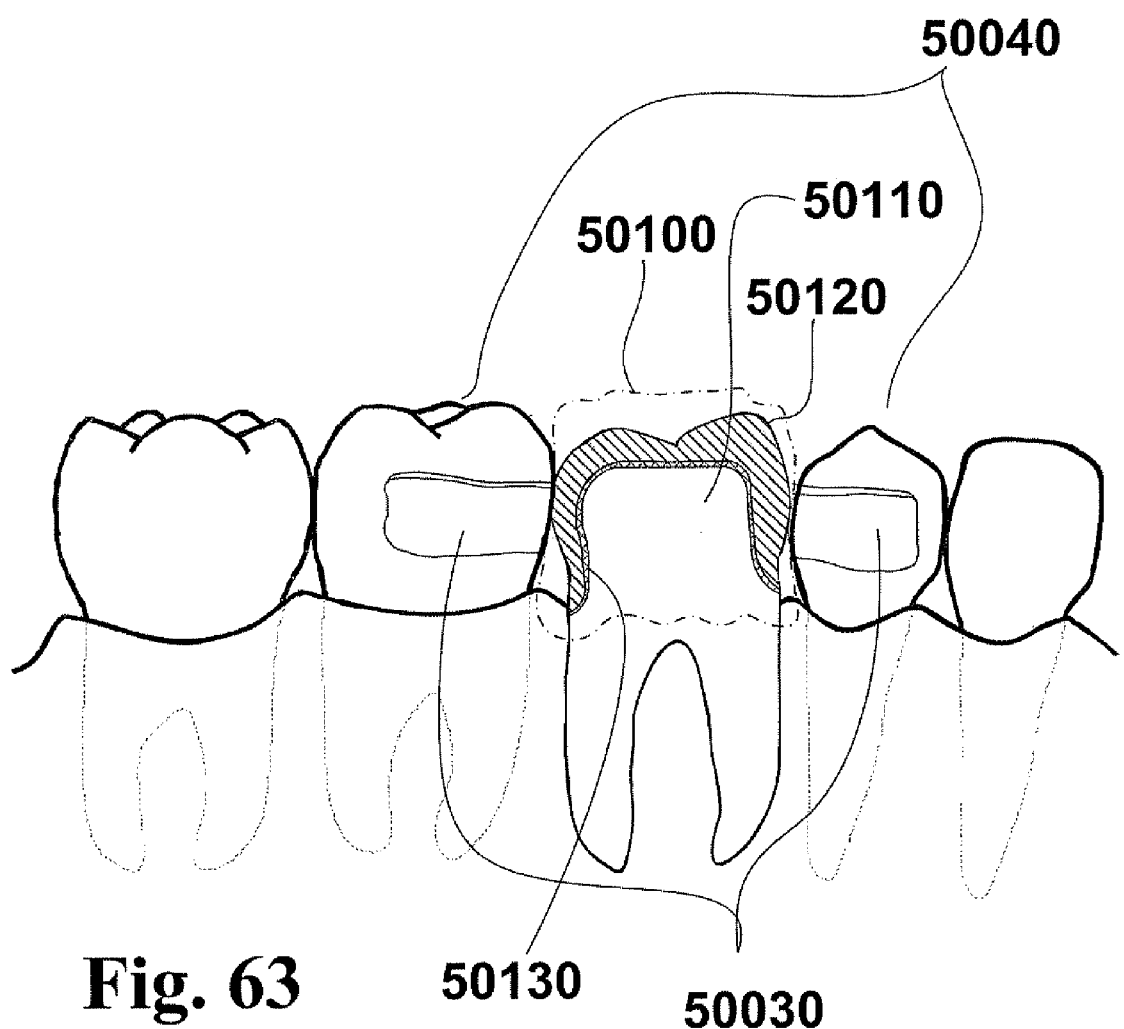
FIG. 63 shows a cut view of the aforementioned prosthesis with a crown portion body forming one part with a splint of FIG. 62.

A cut view (50100) of this prosthesis (50000) is depicted in FIG. 63. In this cut view (50100) it can be seen, that the prosthesis (50000) comprises a one-part implant (50110) and a cap (50120) forming one part with its wings (50030) attaching to the adjacent teeth (50040). The cap (50120) can be attached to the one-part implant with adhesive means such as cement. However, a partially adhesive silicone (50130) can also be used for attaching the cap to the one-part implant. This provides the advantage that micro-movements of the cap and splint (as one part) are damped. This reduces the micro-movements of the implant and, thereby, enhances the integration of the implant into the alveole.

Figure 64:
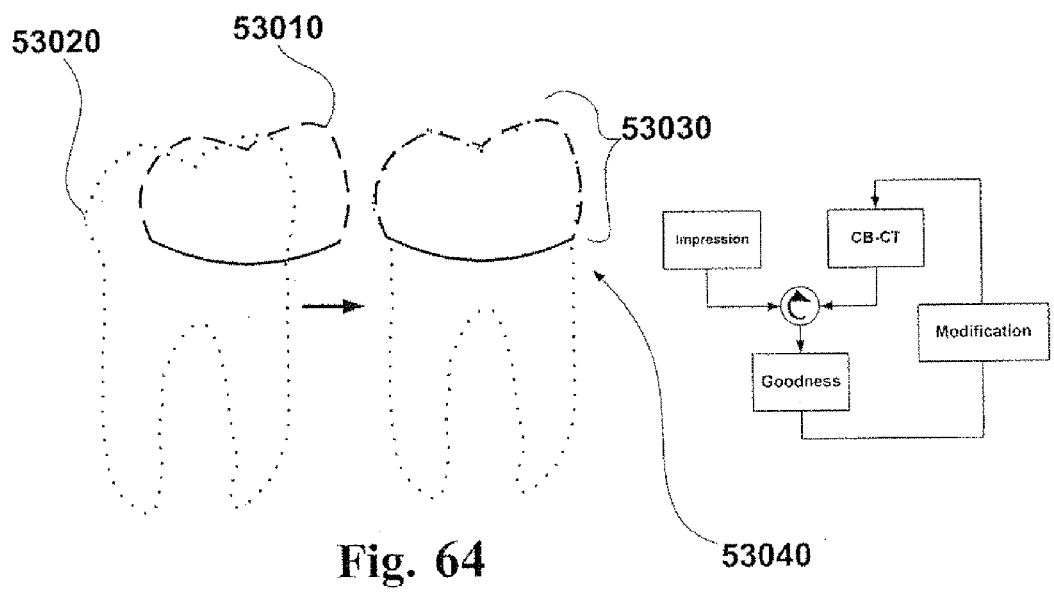
FIG. 64 shows an iterative method for processing previously acquired data for the fabrication of the mentioned prosthesis.

A further enhancement of the present fabrication process is shown in FIG. 64. Therein, two sets of surface-data are shown, i.e., surface-data of the crown portion (53010) of the original tooth derived from the impression of the patient's denture and surface-data derived from the computed tomography image (53020) providing information on the whole anatomy of the patient's non-functional tooth. It is to be noted that the uncertainty of the dataset provided by the impression lies at about, 10 to 50 micrometer. The uncertainty of the dataset obtained from the computed tomography device shows an uncertainty within 200 to 300 micrometer. The impression data may include digital representations of the gum line surrounding the crown of interest, Having these two types of surface-data, it is of interest to combine both datasets in the overlapping region (53030), i.e., in the area of the crown portion. For this combination of datasets, the overlapping regions of the two datasets are placed together using bets-fit algorithms. From the combination of the two datasets, a goodness/performance value of the fit is obtained as a value being calculated from the differences between the two datasets at corresponding points of the virtual prosthesis surface. Such a goodness value represents a measure representing the quality/performance of the fitting of the two datasets. For example, the sum of the distances raised to the second power could be used to calculate such goodness value of the best fit. From the combined dataset (53040), CNC-instructions are derived for the fabrication of the prosthesis.

In the following, a procedure is described for enhancing the quality of the combined dataset. The proposed method/procedure executes the following steps: At first, the surface dataset derived from the impression (virtual crown) and the surface dataset derived from the computed tomography device data (virtual tooth with roots) are combined to one surface dataset of a virtual tooth. For this fitting combination a first goodness value is calculated that is saved electronically for further steps. Then, the surface data of the virtual tooth (combined dataset) is modified, e.g., blown up, biased, moved with respect to inclination and position etc. In a further step, the modified dataset of the virtual tooth is fitted to and combined with the original dataset of the impression. From this second combination of datasets, a second goodness value is derived. This second goodness value is saved electronically and compared to the aforementioned goodness value. If the new goodness value is greater, than the first goodness value, the aforementioned procedure is repeated. I.e., the second combined dataset is modified as before, e.g., blown up, biased, etc.

This iterative procedure is repeated several times with different, e.g., systematically or randomly chosen modifications being applied to the respective combined dataset. In doing so, it is a goal to find or identify a maximum goodness value. For this search of the maximum goodness value, many kinds of statistical methods and mathematical optimization methods can be utilized in which the kind of modifications and the directions of modifications are derived from adaptive algorithms based on the kind of modification and its direction and the gradient of the quality (i.e., the goodness value) calculation the goodness value iteratively.

Figure 65:
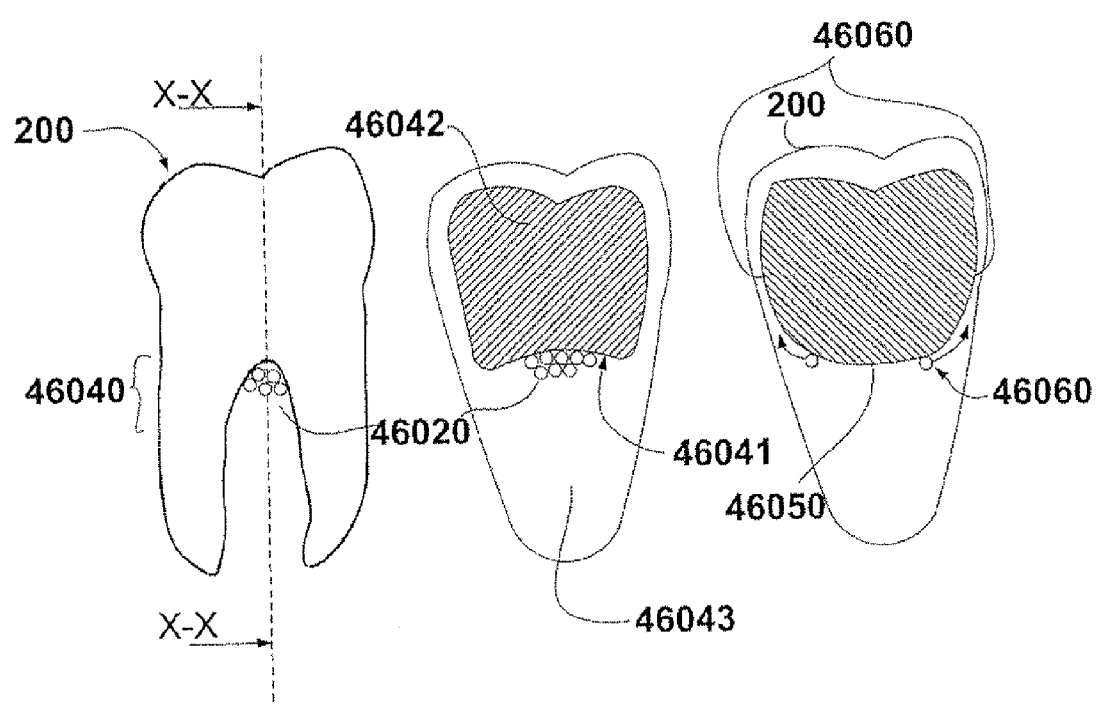
FIG. 65 shows a modification of prosthesis comprising a special shape in the area between the roots of the prosthesis.

In a further embodiment as shown in FIG. 65, the prosthesis (200) shows a special form which in comparison to the natural form of the original tooth provides advantageous features in the process of integration. The problem with a prosthesis providing the form of the original tooth is that in the process of integrating the tooth into the alveole it may happen that, e.g., an air inclusion (46020), like a bubble, or bacteria (46030) may settle beneath the upper area (46040) between the roots of the dental prosthesis. The reason for this settlement of bacteria and/or air inclusions is represented by the three-dimensional extension of a concave lower limitation (46041) as shown for example, in the cut surface (46042). It is shown in the cross-section view (X-X) of the prosthesis (46043) where the air inclusion (46020) is located in the upper area (46040) between the roots of the tooth. By modifying the design of the dental prosthesis (200) with a convex lower limitation (46050) of the shown cut surface, a prosthesis is provided with a form that enables air inclusions (46060) to slide up along the sides (46070) of the prosthesis. Thereby, the settlement of bacteria in that area (46040) between the root portion of the proposed dental prosthesis (200) can be avoided. The design and modification process can be performed on a standard CAD computer system using a standard software that is able to visualize and manipulate surface data (e.g., in STL format). For example, the software application product Studio 11 (Geomagic) is very much suited to perform the aforementioned modification of the prosthesis design. Also the aforementioned software products MAGICS and Solid Works are suitable for this task.

In another embodiment, the design modification of the prosthesis would include displacing the forked shape between the legs of the root portion in the direction of the root tip(s). This would be a clinically indicated beneficial modification over the actual corresponding shape of the non-functional tooth, to increase the transgingival middle portion in order to have more vertical height for the gingiva to seal gum and the prosthesis surface against bacterial penetration.

Figure 66:
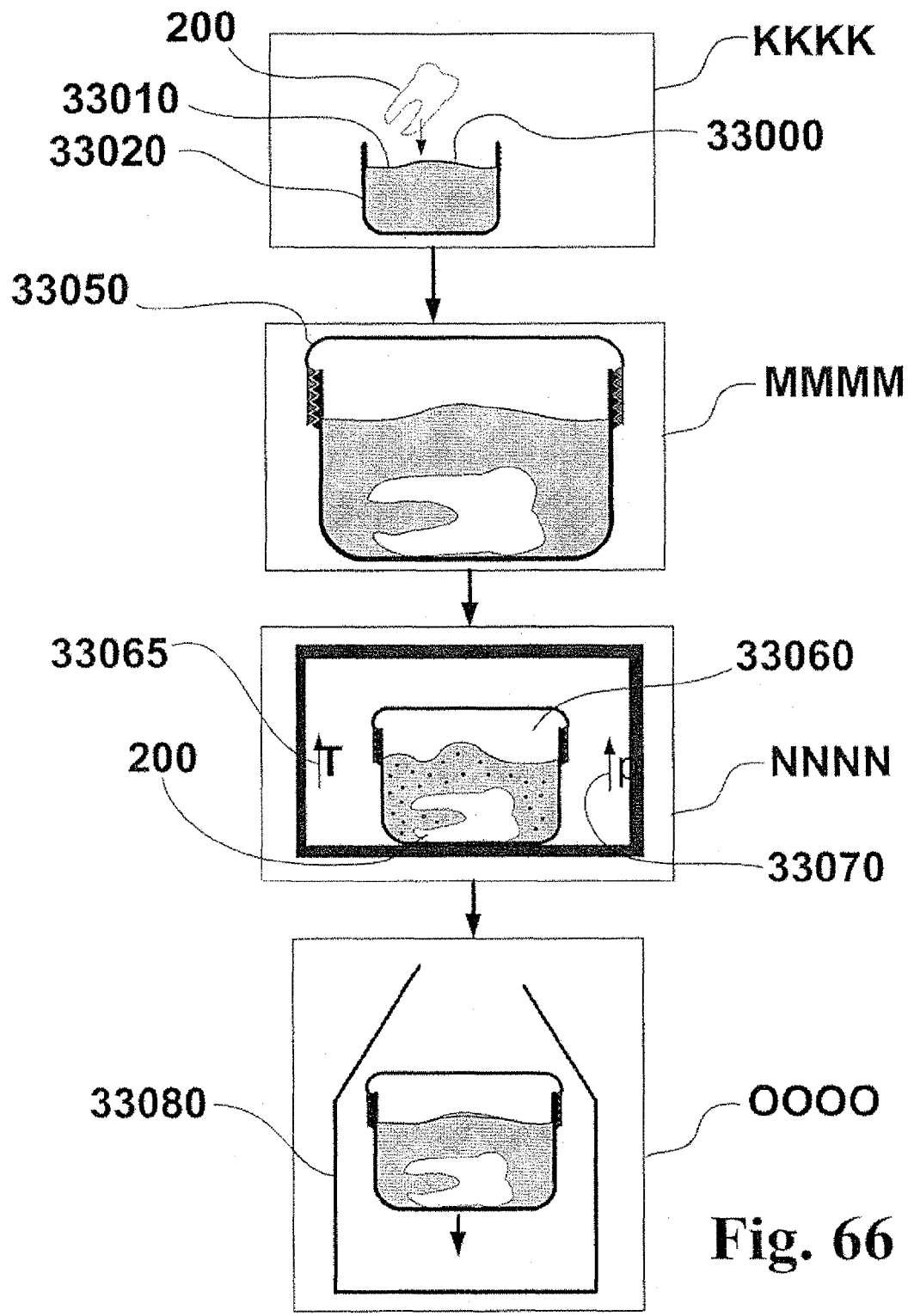
FIG. 66 shows a method for the wet delivery of the dental prosthesis.

A method for delivering a prosthesis to a customer according to an embodiment of the present invention is depicted in FIG. 66. This process enables the dental prosthesis (200) or components thereof to be delivered in a wet environment (33000). This wet environment can be achieved by a package filled with a fluid or humid gas. It is exceptionally important that the outer surface of the root portion body is moistened. Thereby, non-biocompatible substances are prevented from occupying the outer surface of the root portion body which could lead to disabling the ability of cells to populate the root portion areas. Also, air bubbles that sit in the porosity or cavities of the roughened surface could disturb tissue integration. In the first step (KKKK), the finished dental prosthesis (200) is placed in a liquid (33010). The liquid (33010) is contained e.g., in an elastic bag or in a glass container (33020). The liquid is favorably a biocompatible liquid such as an isotonic solution of sodium chloride. In the further process, ultraviolet electromagnetic radiation (33030) is applied to the dental prosthesis (200) in a low pressure environment (33040) such as a vacuum oven. This treatment of the surface of the dental prosthesis, e.g., composed of zirconia, with ultraviolet light enhances the bioactivity of the surface of the dental prosthesis on osteoblasts. Att showed in Biomaterials 30 (2009) 1273-1280 that the treatment of zirconia with ultraviolet light enhances its bioactivity on osteoblasts. Alternatively, a plasma cleaning process can be used to create hydrophilic surface conditions. In the second step (MMMM), the glass container (33020) is closed with a cap (33050), thereby providing a firmly protected dental prosthesis (200) for the delivery to further process steps. In the next step (NNNN), the dental prosthesis (200) and its environment (33060) in the glass container (33050) is sterilized by applying a high pressure hot steam sterilization process. In this high pressure hot steam sterilization process, the glass container (33050) including the dental prosthesis (200) and the surrounding liquid are placed in an oven with increased pressure. In this oven, the temperature is increased (33065) up to a temperature regime in which the dental prosthesis and the liquid are sterilized. To avoid the breaking of the glass container during the increase of temperature in the oven due to the increased pressure inside the glass container with rising temperature, an increased pressure (33070) is applied to the environment of the glass container. In addition or alternatively, a membrane can be used to seal the container, such membrane to allow gas and steam to penetrate, while water in its liquid stage would not be able to penetrate the membrane. In the next step (OOOO), the sterilized glass container is packed into a padded packaging box (33080) for the save delivery to the customer. In order to further optimize the wetting of the surface intended to integrate with tissue, vacuum and/or ultrasonic vibrations can be applied to release air bubbles from the surface of interest.

Figure 67:
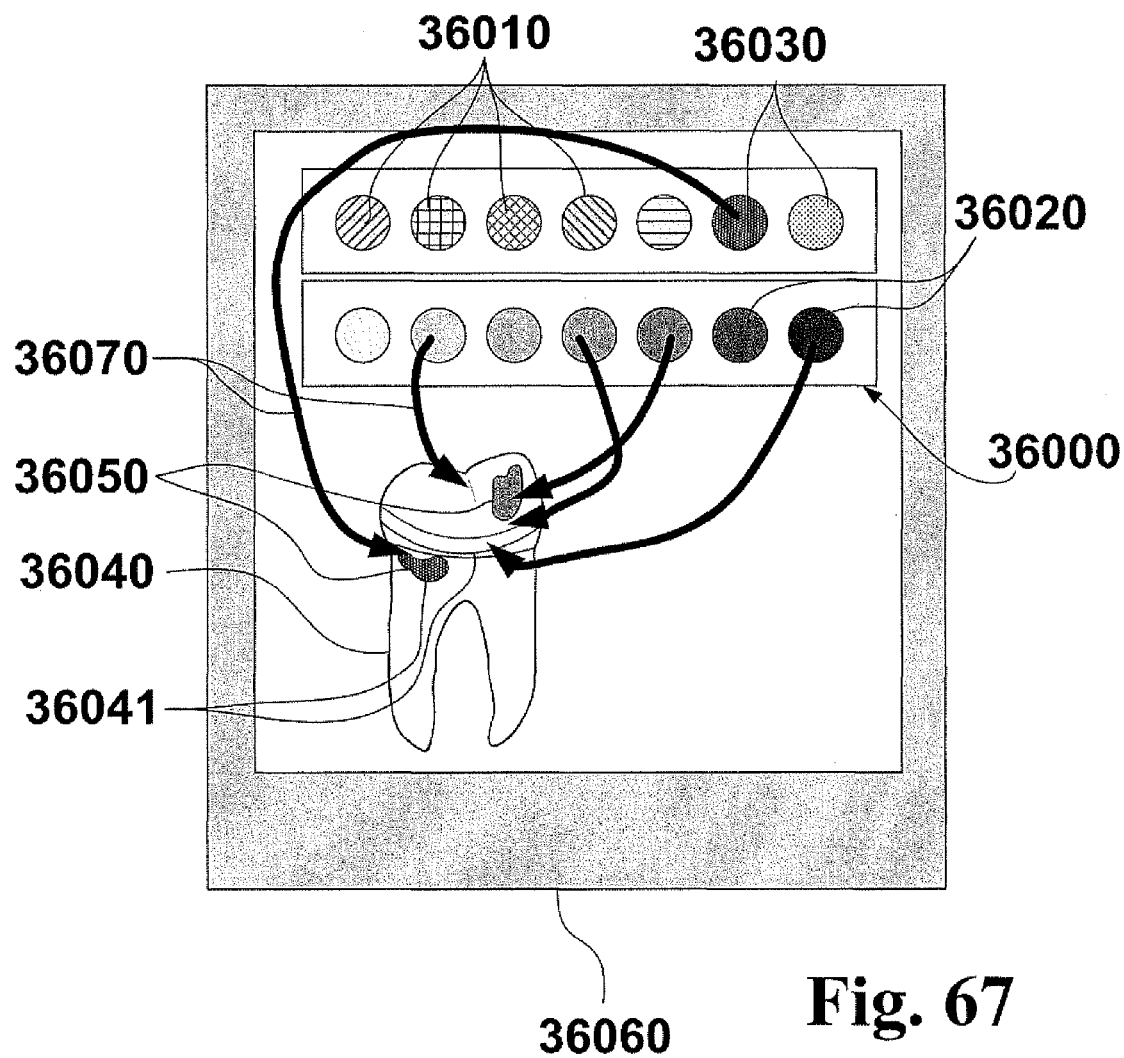
FIG. 67 shows a color pad assembly for esthetically optimizing the dental prosthesis.

In another embodiment of the present invention depicted in FIG. 67, a pad (36000) is utilized to provide a selection of different areas (36010) of varying color (36020) and texture (36030). The pad (36000) can be utilized for an esthetic adjustment being applied on the dental prosthesis to be fitted esthetically to the adjacent teeth. In a first step, the tooth (36040) to be replaced is placed aside the pad (36000). A skilled person, e.g., the dentist of record, compares certain spots and stains (36041) present on the natural tooth to be replaced (36040) to the different areas on the pad (36000), thereby identifying which color-area or texture-area (36050) on the tooth corresponds to an area (36010) on the pad. By taking a picture (36060) and printing it, the dentist can mark on the picture (36060) which area (36050) on the tooth corresponds to a certain area (36010) on the pad, e.g., by drawing arrows (36070) on the picture (36050) between the pad and tooth. In the process of esthetically adjusting the dental prosthesis to the adjacent teeth, a skilled person can utilize the color pad in comparison to the picture to make the adjustments, e.g., by painting stains and marks on the dental prosthesis. This step is of particular importance since the true colors of a tooth (36040) are usually not well represented on a picture. By the proposed method the dental prosthesis receives a natural look fitting esthetically to the adjacent teeth and providing the natural stains and marks that were already present on the tooth that was replaced.

Figure 69:
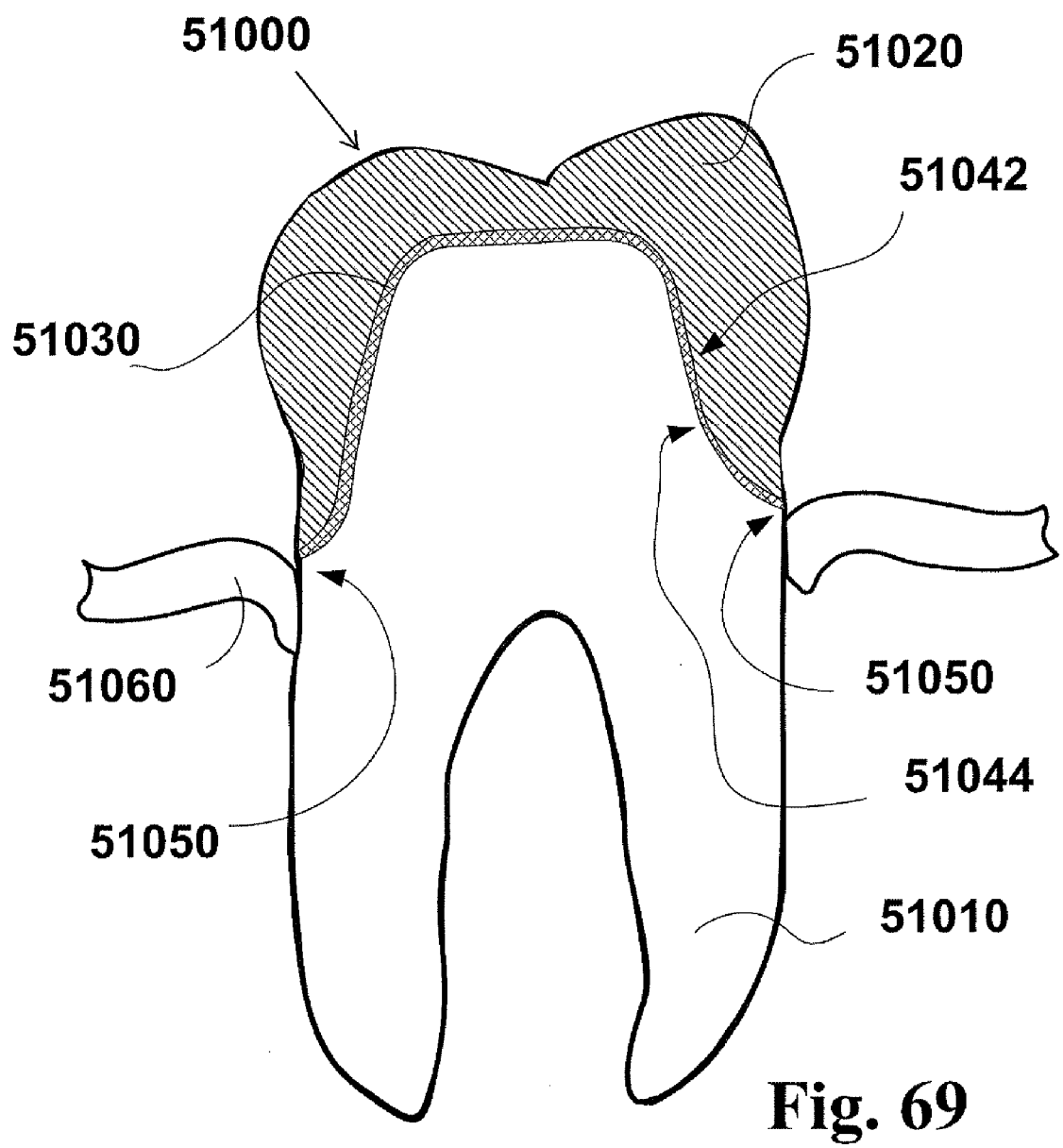
FIG. 69 shows a dental implant prosthesis with a custom-shaped joint between an implant body and a crown.

In an exemplary embodiment, a cross-sectional view of a one-piece dental prosthesis is shown in FIG. 69. The term one-piece refers to the root body (51010) portion and the crown body (51020) which are assembled as a one piece body (51000). The body (51010) is mainly composed of a ceramic material. This can be pure zirconia, or a ceramic matrix composite like yttria-stabilized (tetragonal phase) zirconia (e.g., Y-TZP zirconia, NaceraZ Medium/Ivory, Doceram), alumina-toughened zirconia (e.g., ZIRAL-DENT®, METOXIT) or zirconia toughened alumina. On the top of the one piece body (51010), a translucent cap, the crown body (51020) is made of feldspar ceramics or lithium disilicate ceramics (e.g., IPS e.max CAD HT—highly translucent—or IPS e.max CAD LT—low translucent, available in various color shades, Ivoclar Vivadent) is placed and attached with adhesive means (51030). This is for example, a temporary silicon based adhesive (e.g., TempoSIL®2, coltène whaledent), a temporary non-silicon based adhesive (e.g., eugenol-free cement, e.g., RelyX™ Temp Nebr., 3M ESPE), or a permanent cementation (e.g., RelyX Unicem, 3M ESPE). The spacing between the one piece body (51010) and the translucent glass cap (51020) can be adjustable depending on the adhesive material used for the attachment of the glass cap onto the ceramic body portion. In an exemplary embodiment, the gap is 100 microns. An advantageous range is between 50 and 200 microns. In an alternative embodiment, the adhesive material (51030) can be composed of glass solder (e.g., Hotbond Tizio silicate coating and Hotbond Plus, DCM), where the parts are fused together utilizing a hot-bond process. In the process of integration, the one-piece dental prosthesis (51000) can be placed into the alveole as a whole. Note, this is in contrast to procedures used with state of the art dental implants where a root portion is integrated and in a further step a crown portion is attached to the root portion. In order to prepare the surfaces of interest, a cold-processed tribochemical method for silicatising surfaces may be applied (e.g., Rocatec Plus by 3M ESPE). The silicatised surface is prepared for bonding (e.g., cementing) by applying a silanising surface conditioning, i.e., a silane resin primer (e.g., ESPE Sil, 3M ESPE).

In an exemplary embodiment, a hot processed glaze finish (e.g., Crystall/Glaze and Crystall/Glaze Liquid, Ivoclar Vivadent) is applied to the translucent crown cap (51020) prior to temporary or permanent bonding.

Usually a crown is bonded in the patient's mouth in the dentist's office. In an exemplary embodiment of the invention, the bonding takes place at the site of the manufacturer to thereby increase accuracy and the quality of the bonding itself.

Koebel et al. disclose in WO 2008/017472 a rough, porous osseoconductive topography of a zirconia implant surface that promotes bonding between the implant and tissue, where in a mixture, comprising of a polymer and at least one ceramic material is applied on a substrate, the mixture further comprising inorganic binders, e.g., phosphates, silicates, carbonates, sulfates. However, it has not been recognized until now by the inventors that dental implants, abutments, prostheses or parts thereof are individualized in its three-dimensional shape prior to such surface coating.

The shape design of mass-produced implants shows a standardized joint between the implant and the crown portion. While the crown is usually custom-shaped to the adjacent and opposite teeth, the implant is not. Therefore, the joint between such traditional crowns and implants is non-customized. Such joints are usually shaped with standardized cylindrical, hexagonal, and conical shape portions. E.g., the hexagonal rising (59030) shown in FIG. 68 (prior art) that is described to serve as prosthesis interface having a generic shape.

In order to obtain a positive lock between the implant and the crown, numerous standard form joints are manufactured in order to try to cover a majority of the possible crown designs. This, however, results in significant additional manufacturing costs and difficulties in inventory management. Alternatively, a smaller number of "standard" designs are manufactured designed to cover most cases. Although the smaller number helps reduce inventory management problems and manufacturing costs, it has been found too often lead to inadequate joint connections and in increased number of collisions between components as the clinician is often provided an improperly fitting connection. That is, the joint having a smaller footprint than ideal is often employed in order to allow for adjustments due to the inadequate connection. Recognized, therefore, by the inventors is the need for a custom joint which can provide a good positive lock between the implant and the crown/intermediate abutment, and which can maximize the "footprint" between the connecting pieces.

Massoud describes in US 2003/0118968 a "scallop-shaped curvature of the juncture of the implant and subsequently attached crown at the gum line" as an attempt to account for an anatomical 3D curvature, where the outer joint-line follows the gum line, showing a curvature like a saddle shape.

Figure 68:
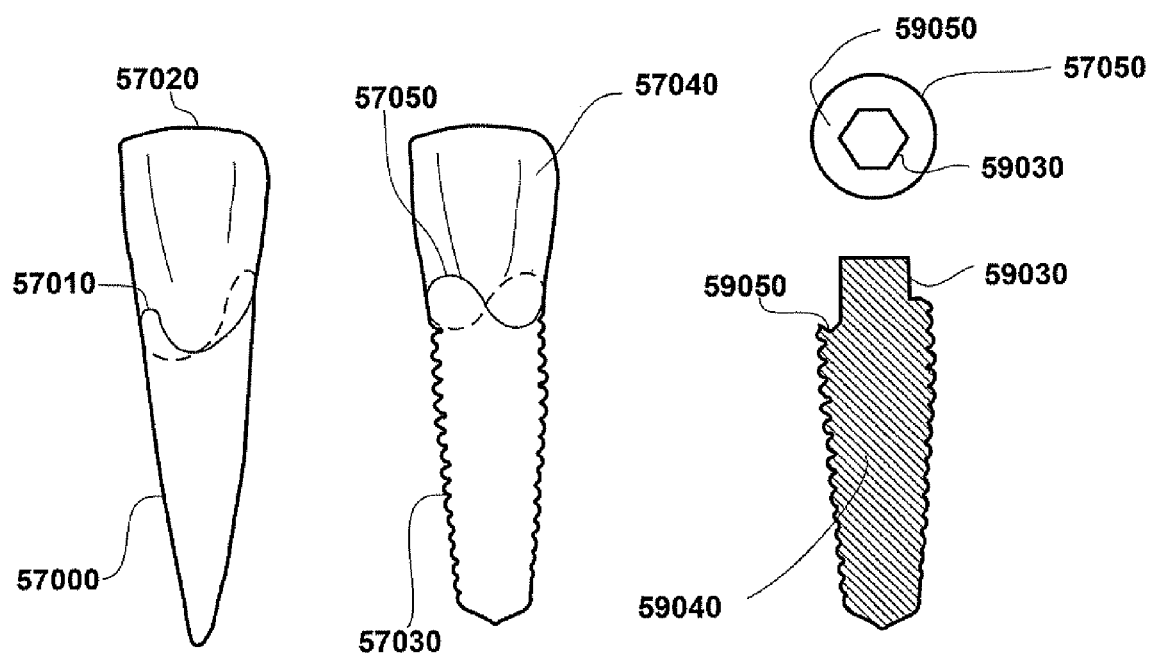
FIG. 68 shows a natural tooth and a prior-art dental implant.

FIG. 68 (prior art) illustrates a natural tooth having a natural enamel crown (57020), a natural dentin root (57000) and the natural juncture between dentin and enamel (57010) showing an individual asymmetric outer contour line on the left hand side of the figure. The implant indicated by (57030) in the middle and right hand side of the figure is a prior art dental implant having a cross-section (59040) showing a cylindrical or respectively slightly conical screw portion having concentric convolutions or threads and having an occlusally facing generic prosthetic interface including a symmetric and generic hexagonal rising (59030), and showing a symmetric and generic scallop-shaped surface (59050)

having a symmetric and generic shaped edge (57050) between the surface (59050) and the concentric outer screw shape. Each of these features are shown in top view on the upper right hand side of the figure. The view shown in the middle of the figure shows a prosthetic crown (57040), which is affixed to the aforementioned hexagon rising (not shown in the middle view) of the prior art implant (57030).

The inventors, however, recognize the limitations of such anatomically shaped mass-produced implant joint portion where a limited amount of standardized shape is supposed to fit all individual situations of the patients of interest.

Accordingly, various embodiments of the present invention provide apparatus and methods of manufacturing or otherwise providing a custom prosthesis interface having a three-dimensional surface shape positioned and formed to create a form locking fit with respect to the crown/abutment and the implant body, which can maximize or at least significantly increase the footprint of the locking fit, which can reduce and/or eliminate collisions between manufactured components, and which allows individualized stocking—thus, eliminating the need to manufacture multiple potential versions of the joint.

Again, FIG. 69 illustrates an exemplary embodiment of the present invention. The prosthesis (51000) shown in the figure has an anatomically custom-shaped edge to the cross-section (51050) adjacent the gum line, where the root-shaped outer surface portion corners to an occlusually-facing interface portion (51044) to receive the crown cap (51020). The joint line of the juncture (51030) between the implant body (51010) and the crown cap (51020) shows in the cross-sectional view an individual, asymmetrical custom-shaped rising over the circumferential edge (51050) curvature in the direction of the main longitudinal axis of the prosthesis. The occlusually-facing surface (51044) of the implant's body (51010) correlates in its three-dimensional shape to the corresponding interface surface (51042) of the crown (51020), together creating a form-locking fit. Further, in an embodiment of the prosthesis, the individual, custom-shaped curvature of the outer joint (partially shown in the cross-sectional view as edge 51050) is designed and manufactured to follow either an adjacent gum line of the gingiva (51060) of the patient or parallel to a bone crest shape, or a combination thereof.

The design process of both the implant body (51010) and the crown cap (51020) includes deriving from clinical imaging data representing the bone crest and/or the gum line, the virtual representation (i.e., the custom design) of the adjacent joint surface shapes (51042 and 51044) of the virtual representations of the implant body and of the crown cap. In another method step, numerical machine control data are derived from the custom design of the joint shape and parts are machined (or made otherwise by rapid prototyping technologies) based on such numerical machine control data, the parts having physical joint shapes substantial to virtual custom design data.

According to the illustrated embodiment, the customized joint interface (51030) between the implant body (51010) and the crown cap (51020) comprises a customized three-dimensional shape, i.e., a three-dimensional surface that separates the crown portion (51042) from the root portion (51044). In contrast to joints known from the prior art between an abutment and a crown, the shown joint is a customized joint which individually correlated to the dental anatomy of the patient's tooth to be replaced and the adjacent dental structures, including the gum lime, the bone socket, the adjacent and opponent crowns. This means that the points of separation along the juncture gum (51060) at the intersection between the root portion and the crown portion are individually designed, and individual, in most cases asymmetrical instead of showing a generic symmetrical shape. Moreover, the course of the joint is individually form-fitted to the form of the crown cap (51020) to be placed on the implant body (51010).

A problem occurs when both, the implant body (51010) and the cap (51020) are fabricated in a parallel process, i.e., both the implant and crown are fabricated based on data obtained from the scan and impression of the original denture. Then, the customized joint interface (51030) is designed for both parts based on the aforementioned data. However, in such a parallel fabrication process, small fabrication failures and inaccuracies can lead to two joint portions (i.e., two three-dimensional surfaces of the implant body and the crown portion) that in some cases do not totally fit together. This is especially an issue when the two parts are both made of hipped (HIP) zirconia since only small corrections can be applied to such a material. In an exemplary fabrication method of the aforementioned prosthesis (51000) depicted in FIG. 69, the implant body (51010) and the cap (51020) are instead fabricated in a serial fabrication process. Therefore, in a first step, the implant body (51010) is fabricated with a customized surface forming the root portion and the joint portion (51044). In a further step, the three-dimensional surface is scanned or an impression is taken, thereby, acquiring data that actually represents the embodiment of the customized joint as it is embodied in the fabricated implant body (51010). The data obtained from the scan of the customized joint (51030) is then utilized for the fabrication of the cap (51020) having a customized joint portion that fits to the joint portion of the implant body (51010) with a high accuracy.

In stark contrast, the common process using CAD/CAM technologies making dental crowns and bridges receives the custom shape of the tooth preparation to form the joint between the natural tooth (or even of a custom shaped abutment); however, such joint shapes are not custom generated or designed (i.e., originated) in the virtual domain, they are physically man-made and shaped by the doctor of record in the mouth of the patient of interest. When in new state-of-the-art developments abutments (the transgingival middle-pieces that connect the implant screw with the crown) are custom shaped with respect to the outer shape that finally receives the crown, the implant facing joint/interface surface is of a three-dimensional standard (i.e., non-custom) geometry.

Figure 70:
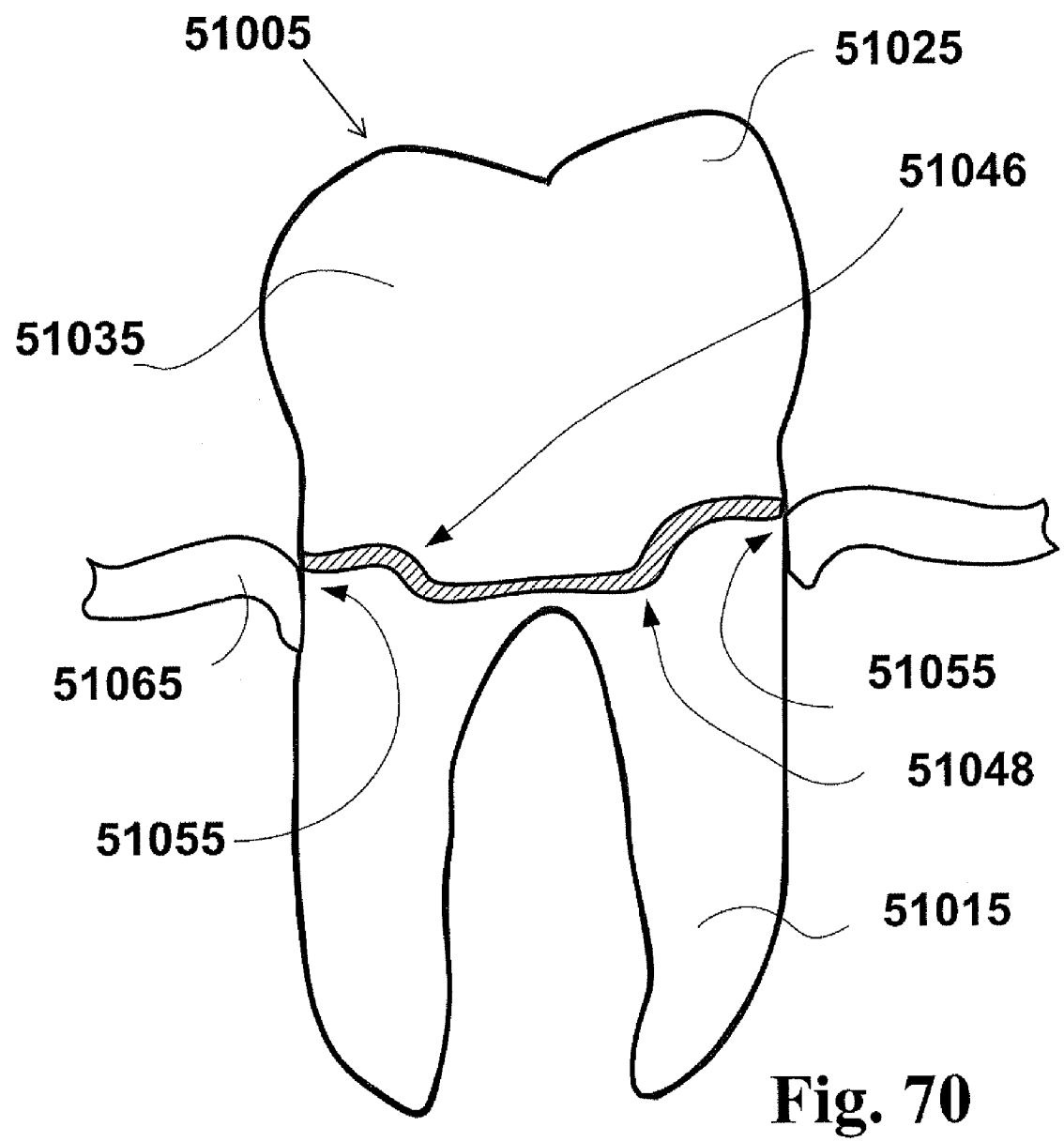
FIG. 70 shows a dental implant prosthesis with a custom-shaped joint between an implant body and a crown.

FIG. 70 illustrates a cross-sectional view of another exemplary embodiment of the present invention. The prosthesis (51005) has an anatomically custom-shaped edge to the cross-section (51055) adjacent the gum line of the gingiva (51065), where the root-shaped outer surface portion corners to an occlusually-facing interface portion (51048) to receive the crown cap (51025). The joint line of the juncture between the implant body (51010) and the crown cap (51020) shows in the cross-sectional view an individual, asymmetrical custom-shaped indent over the circumferential edge (51055) curvature in the direction of the main longitudinal axis of the prosthesis. The occlusually-facing surface (510488) of the implants body (51015) correlates in its three-dimensional shape to the corresponding interface surface (51046) of the crown (51025), together creating a form-locking fit. Further, in an embodiment of the prosthesis, the individual, custom-shaped curvature of the outer joint (partially shown in the cross-sectional view as edge 51055) is designed and manufactured to follow either adjacent the gum line of the gingiva (51065) of the patient or parallel to a bone crest shape, or any combination thereof.

Figure 71:
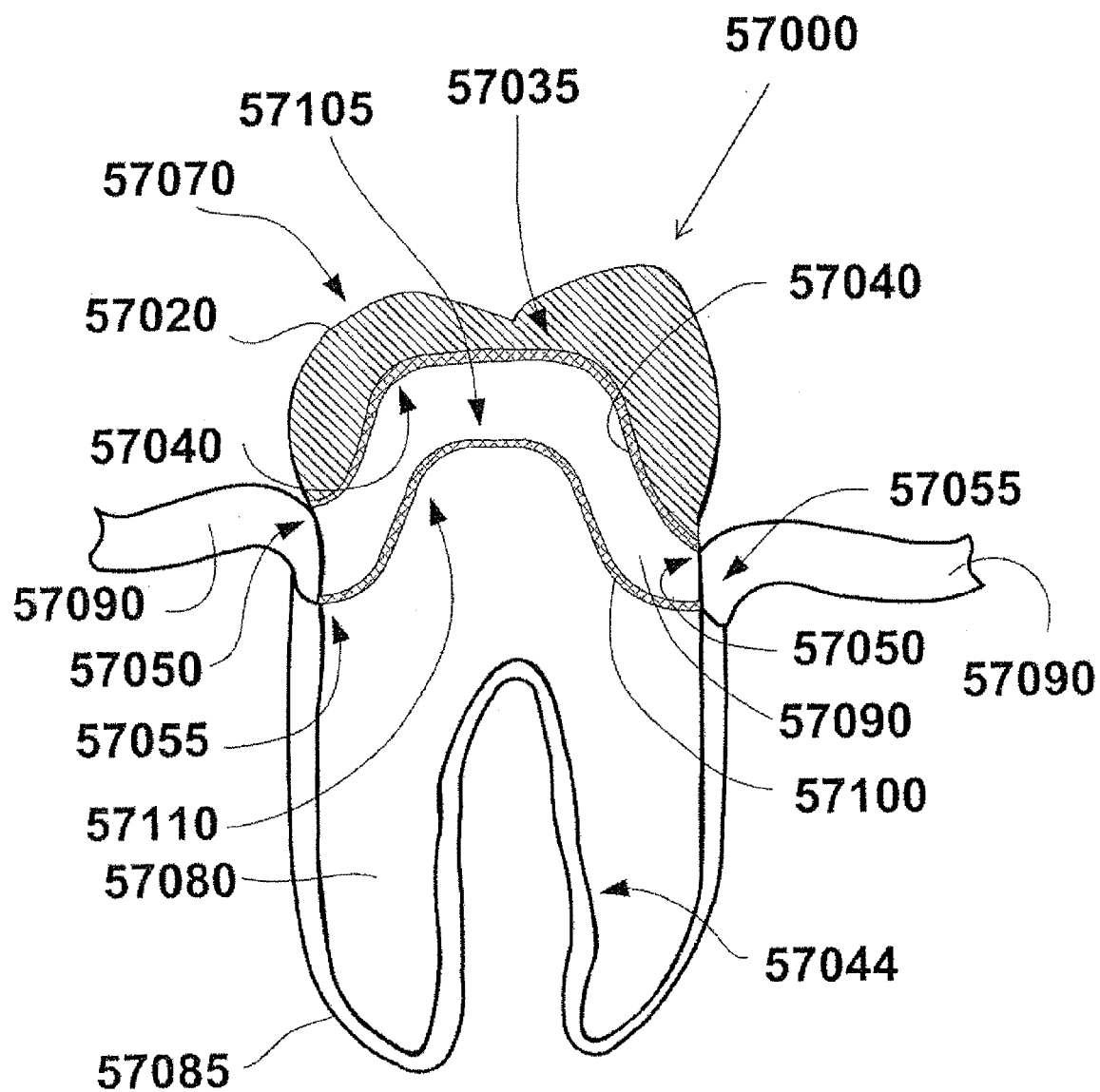
FIG. 71 shows a compound one-piece prosthesis with a first joint between an implant body and a transgingival cap and a second joint between the transgingival cap and a crown.

FIG. 71 shows a cross-sectional view of a single tooth prosthesis (57000) which is a variant of the embodiment of the dental prosthesis shown and described in context of FIG. 69 and shows a compound one-piece prosthesis with a first joint between an implant body (57080) and a transgingival cap (57090) and a second joint between the transgingival cap (57090) and a crown (57020). The partially root-shaped implant body (57080) matches the extraction socket (57085) of a pre-identified patient, without interfering with or intruding into the surface socket itself. The implant body (57080) is formed of, for example, commercially pure titanium (e.g., medical grade 2 commercially pure titanium) or a medical-grade titanium alloy (e.g., $Ti_6Al_4V$). The middle piece, the transgingival cap (57090), is made, for example, of ceramic material e.g., Y-TZP zirconia, and serves a similar purpose of an abutment in traditional dental implantology. In an exemplary embodiment, the transgingival cap (57090) is favorably tooth colored, e.g., in its white body state, prior to final sintering by volumetric coloring (e.g., color liquid e.g., Zirkon B4; C3; D4, Zirkonzahn).

Further in the exemplary embodiment, the implant body (57080) and the transgingival cap (57090) are fused together by the above described hot-bond technology, where the titanium surface of the interface (57110) is first silcatised by a coating applied in a heating process (e.g., Hotbond Tizio silicate coating), then the two parts of interest (57080 and 57090) are glass soldered (e.g., Hotbond Plus, DCM), building together a fused extended implant body. The outer joint line (shown as an edge 57055) in the cross-sectional view of the joint (57100) is sub-gingivally positioned and the transgingival cap or abutment portion (57090) is permanently fused and sealed reducing significantly the risk of an opening or gaping under load and of bacteria colonization at the interface compared to traditional implants. The interface between the transgingival cap and the crown is discussed in the context of FIG. 69.

The embodiment of FIG. 71 has two fully custom-shaped joints or interfaces, the one (57100) positioned sub-ginivally positioned e.g., at the bone crest level, and the second (57040) positioned iso- or supra-gingivally. Each pair of surfaces that build the two prosthetic interfaces (57110 and 57105) and (57040 and 57035) create a form locking fit. The respective three-dimensional surfaces (shown as cross-sectional view) dimensionally correlate with the outer three-dimensional shape (57070) of the crown (57020) and dimensionally correlate with each other. According to the exemplary configuration, the design of the shapes of both joints is created or originated in the virtual domain using the digital data representing the anatomical specifics of interest. There is a minimal thickness of 0.2 mm to be considered for the middle-piece i.e., the transgingival cap (57090), In the exemplary configuration, the outer joint line of the interface between the implant body (57080) and the transgingival cap (57090) (shown in the cross-sectional view as edges 57055) follows the saddle shaped 3D curvature of the bone crest adjacent the anatomical socket, while the outer joint line of the interface between the transgingival cap (57090) and the crown (57020) (shown in the cross-sectional, view as edges 57050) follows the saddle shaped 3D curvature adjacent the gum line of the gingiva (57090).

Again, this is not a standard curvature of a cylindrical mass-produced implant. To the very contrary, this design is individually performed per specific tooth of a pre-identified patient. The shape data are derived from clinical images of the dental anatomy of such patent. In this specific context the design takes into account, first the anatomical cross-section of the implant body (57080) substantially matching the shape of the extraction socket, or matching the root of the tooth being extracted, and substantially perpendicular to that cross-section, the 3D curvatures of the two joints between the three parts (e.g., made of different materials) in the longitudinal axis of the dental tooth prosthesis. The substantially parallel gap between the two adjacent surfaces that build the interface is about 100 microns to accommodate a minimal thickness of the glass solder for the sub-gingival joint and for the cement for the iso- or supra-gingival joint.

In a further exemplary embodiment, the shape of the surfaces of each joint extend the outer joint line to the occlusal (i.e., in the direction of the tip of the crown (57020)) to accommodate for a maximum stability for the assembly to withstand mastication forces.

Note, applicable descriptions of FIG. 69 apply to the descriptions of FIG. 71 and vice versa.

Figure 72:
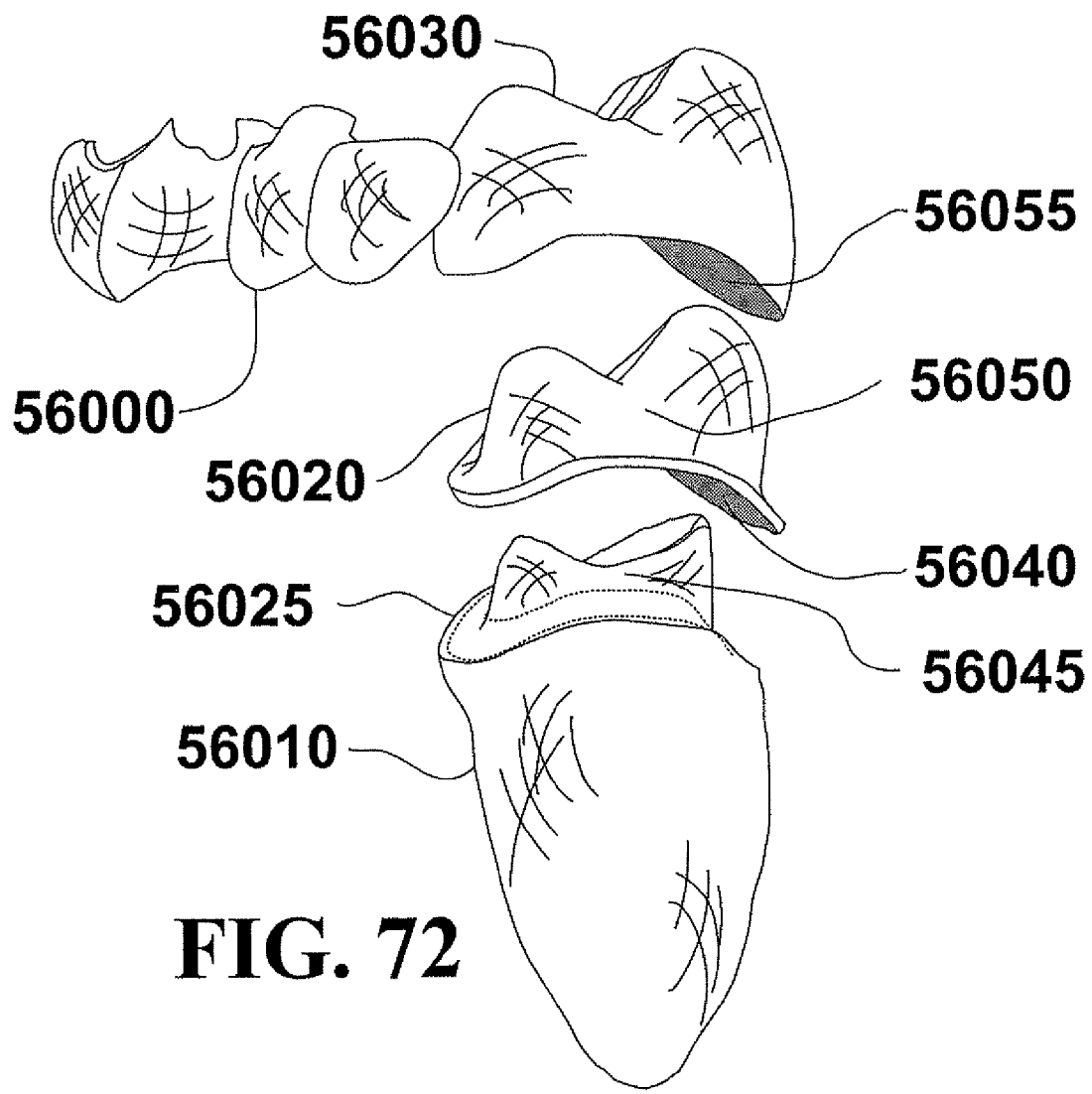
FIG. 72 shows an exploded view of a dental prosthesis consisting of a crown, a trans-gingival portion, an implant body, and a splint.

FIG. 72 shows an explosed view of a dental prosthesis having a crown (56030), a trans-gingival portion (56020), an implant body (56010), and a splint (56000). FIG. 72 further shows, for example, the three-dimensional extensions of the surfaces shown in cross-sectional view in FIG. 71, According to the illustrated configuration, each transversal and lateral cross-section of the components (56030, 56020, 56010 and 56000) are custom-shaped, having an individual three-dimensional shape that is substantial asymmetric, does not include generic concentric shapes, does not include generic symmetric shapes, and does not include convolutional shapes. The respective form-locking fit of the prosthetic interfaces between surfaces (56055) and (56050) and between surfaces (56040) and (56045) is clearly indicated for those skilled in the art. The outer circumferential edge (56025) of the surface (56045) varies in the direction of a mainly longitudinally axis of the implant body (56010) and in transversal direction with respect to the distance to such longitudinal axis. For those skilled in the art, it is clearly indicated that the three-dimensional shapes of the aforementioned interface surfaces correlate with the outer surface of the crown (56030) and with each other. The maximal transversal dimension of the implant body (56010) adjacent the outer circumferential edge (56025) is significantly bigger than the minimal transversal dimension of the implant body (56010) adjacent the outer circumferential edge (56025).

Figure 73:
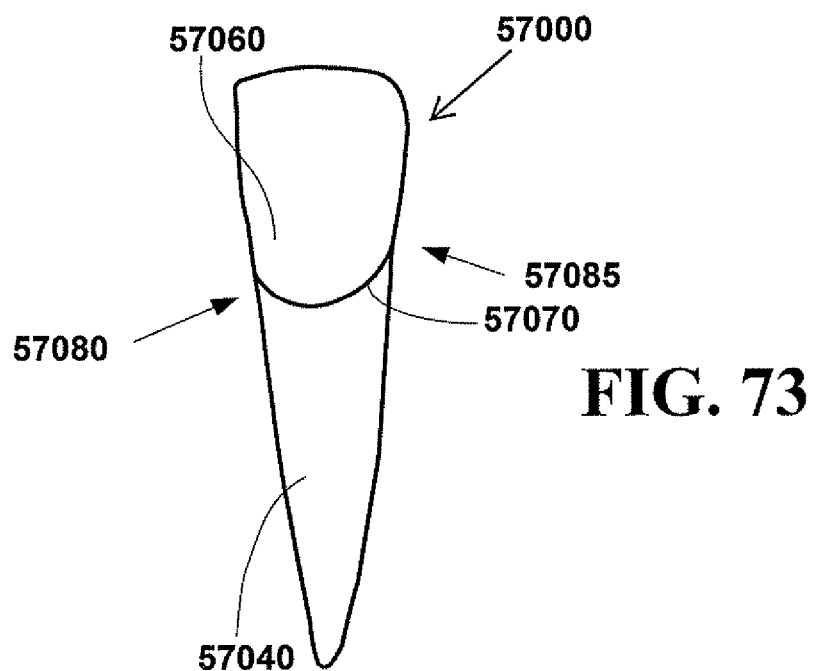
FIG. 73 shows labial view of a dental implant prosthesis.

FIG. 73 shows a labial view of a dental implant prosthesis (57000) having a crown portion (57060) and a root portion (57040) being separated at a junction that shows in the view of the figure as a circumferential line (57070). In the lateral view of FIG. 73, the circumferential line (57070) is asymmetrical, having a different slope or steepness in the direction of the proximal height of that line on one side (57080) compared to the slope or steepness in the direction of the proximal height of that line on the other one side (57085).

Figure 74:
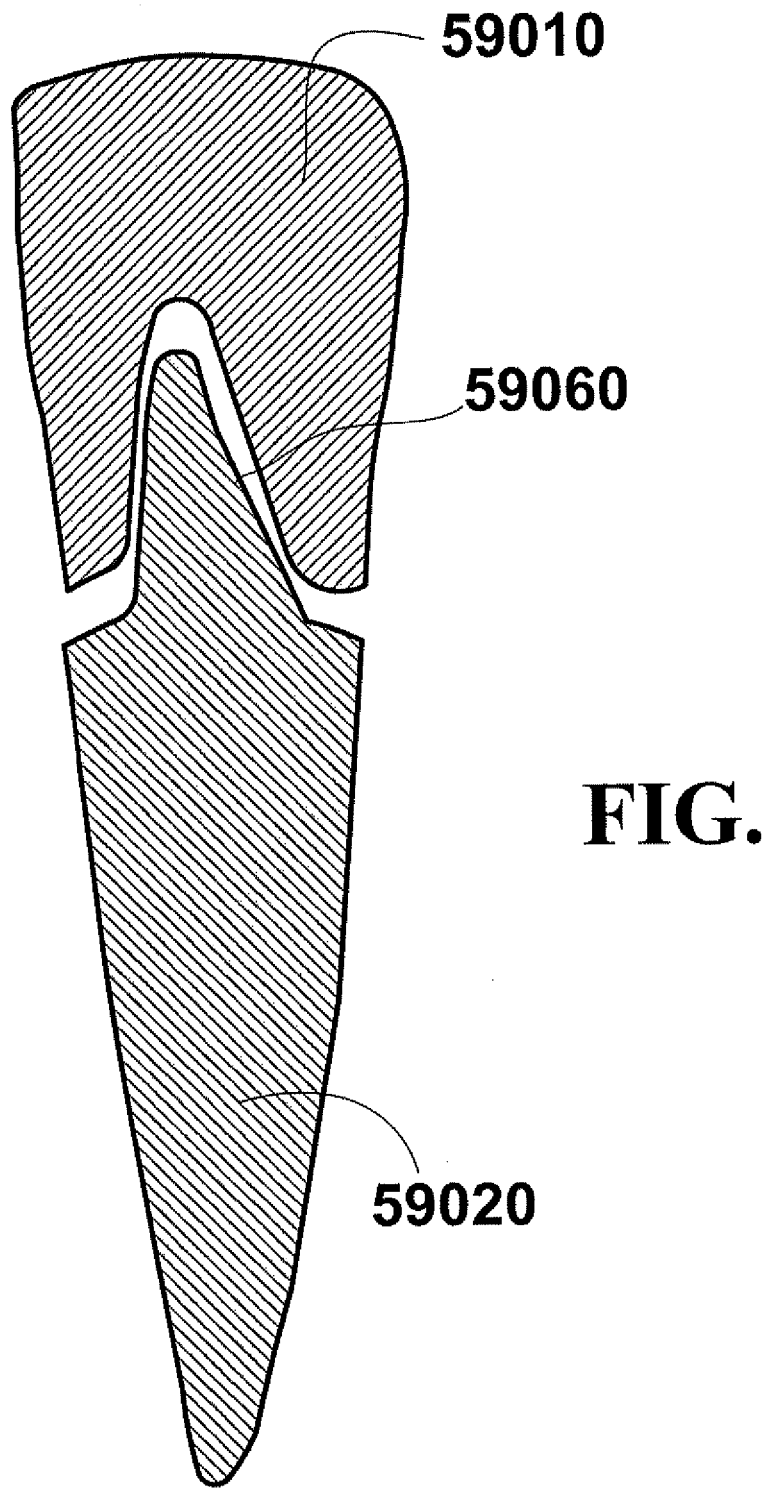
FIG. 74 shows cross-sectional labial view of a dental implant prosthesis.

FIG. 74 shows a cross-sectional lateral view of a dental implant prosthesis having a crown portion (59010) and a root portion (59020) being shown separated at a junction (59060). In the cross-sectional view of FIG. 74, the correlating surface lines that build the form locking fit of junction (59060) are asymmetric, having a different slope or steepness on one side compared to the slope or steepness of the other one side.

Figure 75:
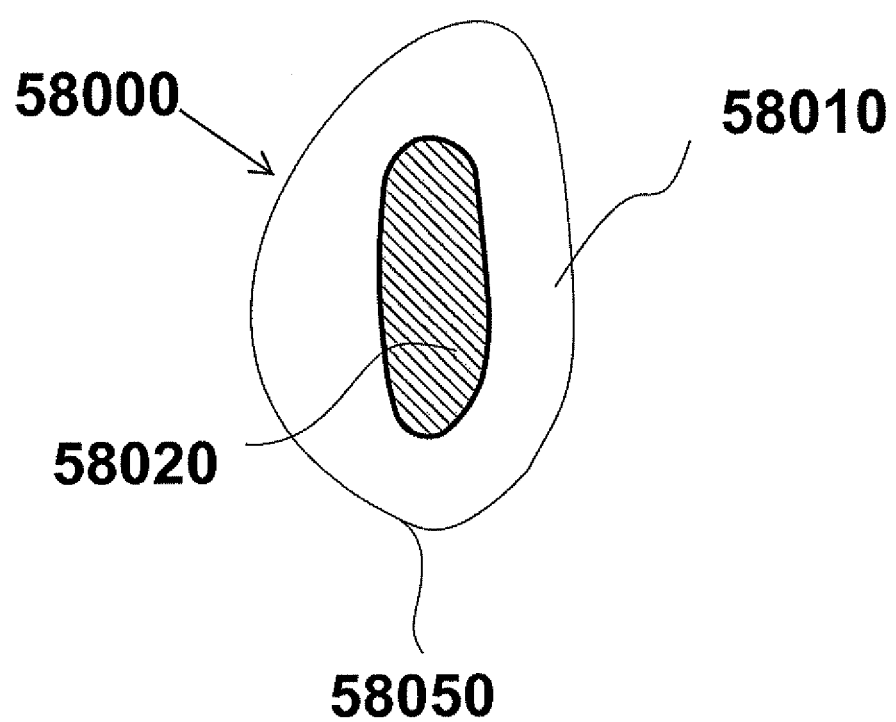
FIG. 75 shows a top view and a cross-sectional transversal view of a dental implant body.

FIG. 75 shows a top view (58050) and a cross-sectional transversal view (58020) of a dental implant body (58000). The maximal transversal dimension of the implant body shown in the top view is significantly bigger than the minimal transversal dimension of the implant body shown in the top view. Its outer circumferential contour is asymmetric as shown in top view. The cross-sectional view (58020) indicates a transversal cross-section of the male portion surface (58010), i.e., a positive rising, of the prosthesis interface that creates a form-locking fit to an occlusally facing prosthesis component (as shown for example, in FIG. 76). The maximal transversal dimension of the implant body shown in the cross-sectional view (58020) is significantly bigger than the minimal transversal dimension of the implant body shown in the cross-sectional view. Its outer circumferential contour is asymmetric as shown in top view, and correlates in its shape and orientation to the outer shape of the top view (58050).

Figure 76:
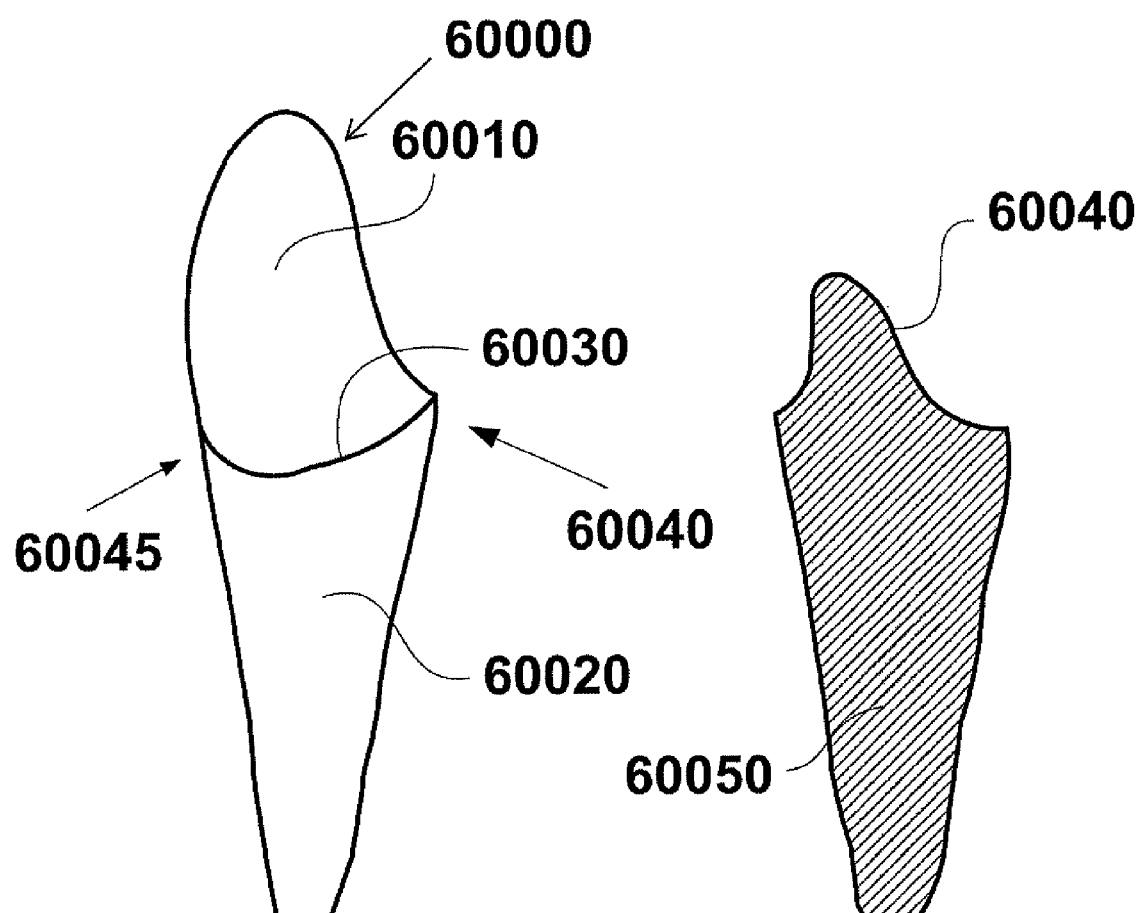
FIG. 76 shows a proximal lateral view of a dental prosthesis and a cross-sectional lateral view of the dental implant body.

FIG. 76 shows a proximal lateral view of a dental prosthesis (60000) having a crown portion (60010) and a root-shaped implant body (60020), being separated at a junction that shows up as a circumferential line (60030) in the view of the figure. FIG. 76 also shows a cross-sectional lateral view (60050) of the dental implant body (60020). In the cross-sectional view (60050) of the implant body (60020), the surface line (60040) of the occlusally facing surface is asymmetric, having a different slope or steepness on one side compared to the slope or steepness of the other one side. In the proximal lateral view of FIG. 76, the circumferential line (60030) is also asymmetrical, having a different slope or steepness in the direction of the labial height of the line at (60045) compared to the slope or steepness in the direction of the lingual height of the line at (60040).

Figure 77:
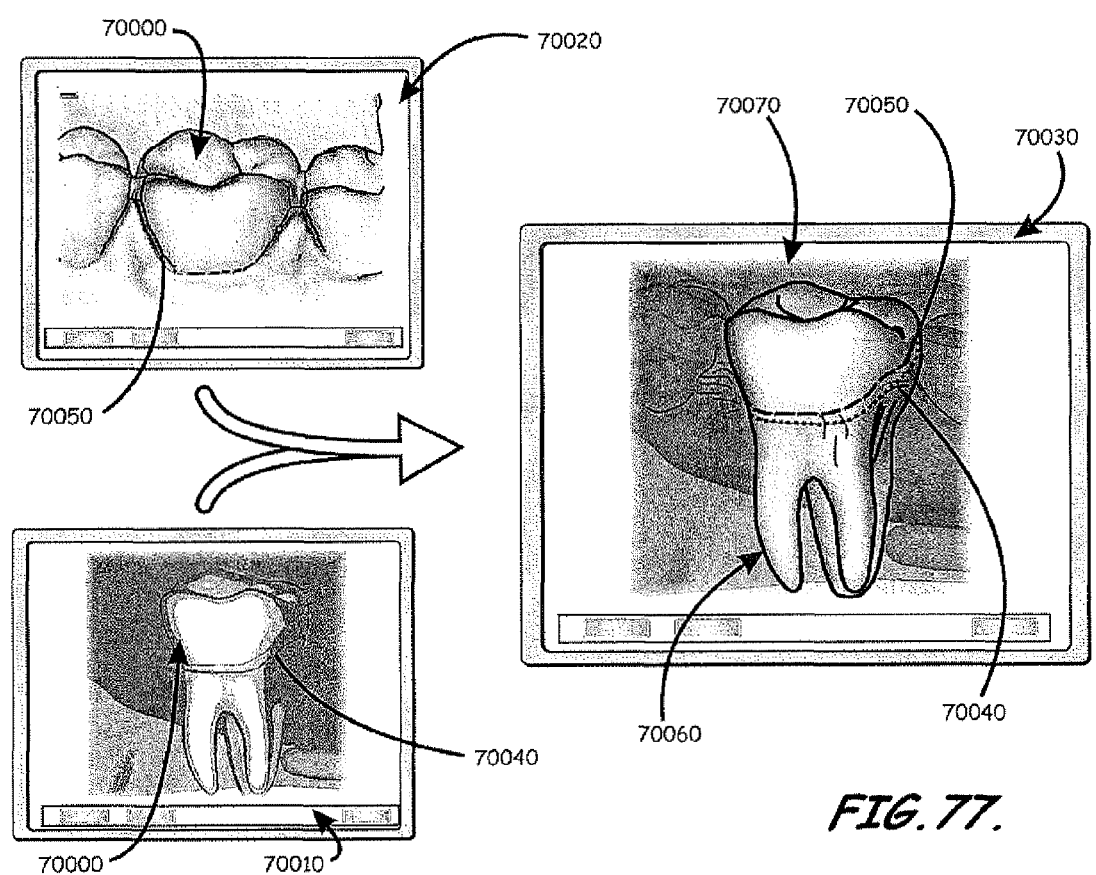
FIG. 77 illustrates combining a surface image with an x-ray image to form a three-dimensional virtual model

FIGS. 77-82 illustrate an example of a method of designing the "two-piece" dental implant 51000 (shown in FIG. 69) to replace a non-functional natural tooth 70000 positioned in a jawbone of a specific pre-identified patient, and FIGS. 83-89 illustrate an example of a method of designing the "three-piece" dental implant 57000 (shown in FIG. 71). As shown in FIG. 77 the "two-piece" and "three-piece" design methods can include the steps of receiving data describing a three-dimensional X-ray image 70010 of at least portions of the patient's dentition (x-ray image data), and receiving data describing a surface scan of a dental anatomy and/or a physical impression of the dental anatomy 70020, defining impression image data made prior to removal of the non-functional natural tooth from the jawbone of the specific patient. The steps can also include forming one or more three-dimensional virtual models 70030 of at least portions of the non-functional natural tooth 70000, for example, by combining the x-ray image data of the x-ray image 70010 (including the location of the bone crest line/bone-facing gum line 70040) and impression image data of the surface impression image 70020 (including the location of the outer gum line 70050), and forming the three-dimensional virtual model or models 70030 of the non-functional natural tooth 70000 to include a modeled virtual root portion 70060 and a modeled virtual crown portion 70070 modeled or otherwise designed based upon to the x-ray image data of the x-ray image 70010 and the impression image data of the surface impression image 70020.

FIGS. 78-82 further detail exemplary steps of designing the two-piece dental implant based upon the three-dimensional virtual model 70030 of at least portions of the non-functional natural tooth 70000. The steps of designing the dental implant include the steps of forming a virtual dental implant body 70080 (FIG. 82) modeling a physical dental implant body having a virtual prosthesis interface (at 70090, FIG. 81) modeling a physical prosthesis interface of the physical dental implant body to receive an occlusally-facing dental prosthesis component 70100. The step of forming a virtual dental implant body 70080 can include forming the virtual prosthesis interface (at 70090, FIG. 81) to have a three-dimensionally contoured implant body surface shape at least partially correlated to a surface shape of an occlusally-facing surface of the modeled virtual crown portion 70070 and crown surface of the nonfunctional tooth 70000.

Figure 78:
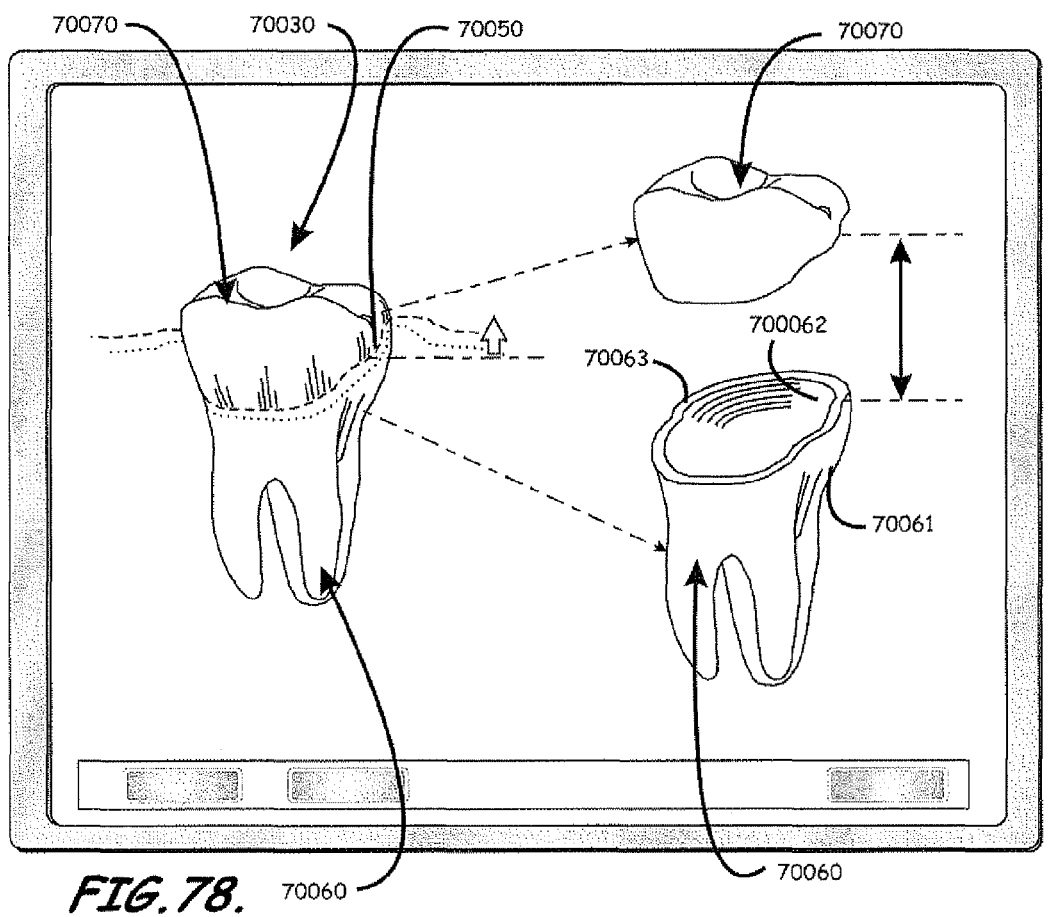
FIG. 78 illustrates the division or separation of parts of a virtual model.

As perhaps best shown in FIG. 78, according to an exemplary two-piece dental implant body configuration, the step of forming a virtual dental implant body 70080 can include separating a portion of the three-dimensional virtual model (including the modeled virtual root portion 70060 and modeled crown portion 70070) along a virtual outer gum line representation 70050. Note, according to the illustrated configuration, the separation/transformation procedure performed on virtual model 70030 can include both digital cutting and digital thickening of the components 70060, 70070 to the inside while maintaining the dimensional integrity of the outer surface. For the two-piece example, this results in the root portion 70060 having a non-infinitesimal thickness as shown, i.e., having a thickness of a substantial dimension. The virtual root portion 70060 shown in FIG. 78 is represented in digital surface data format (e.g., STL), is defined by an outer shell 70061, an inner shell 70062, and an occlusally-facing connecting surface 70063. The design process step of thickening, generally employed in both two-peace and the three-these configurations, creates an inner (smaller) second shell, and then generates the surface boundary that shows the thickness.

Figure 79:
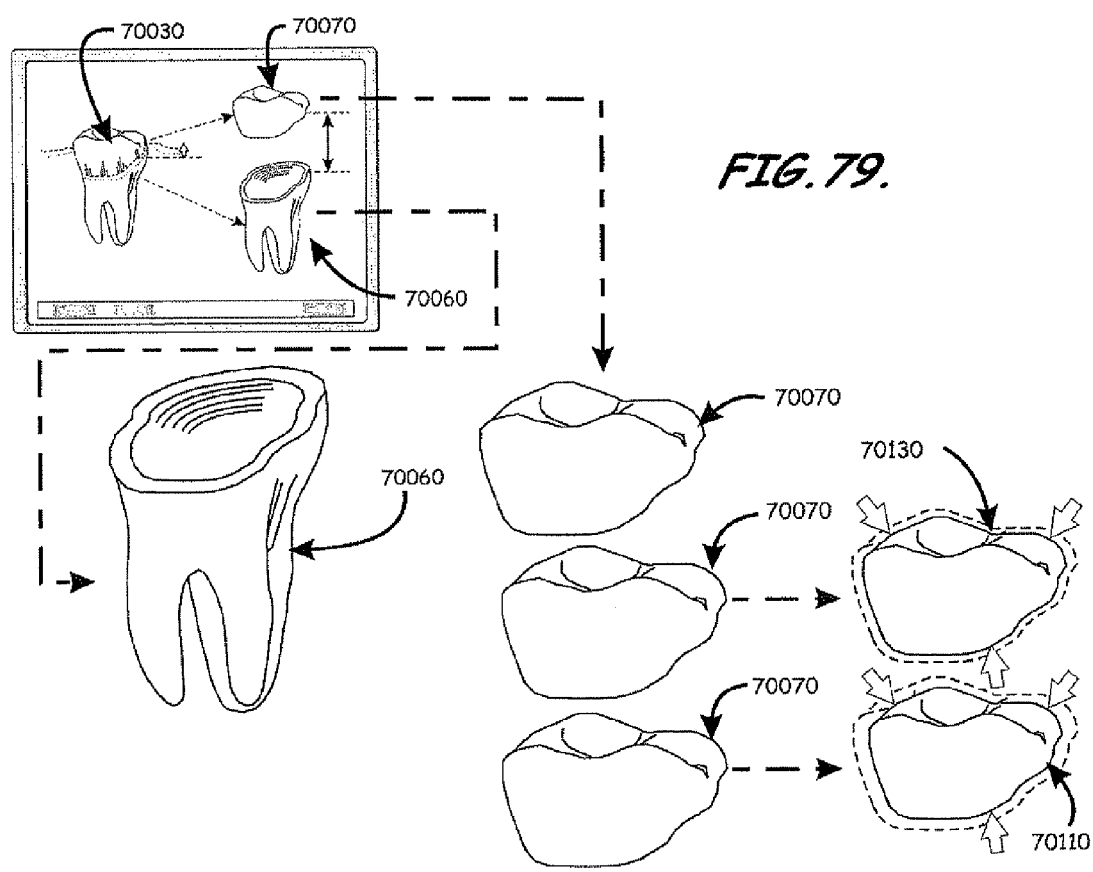
FIG. 79 illustrates copying of portions of the divided virtual model.
Figure 83:
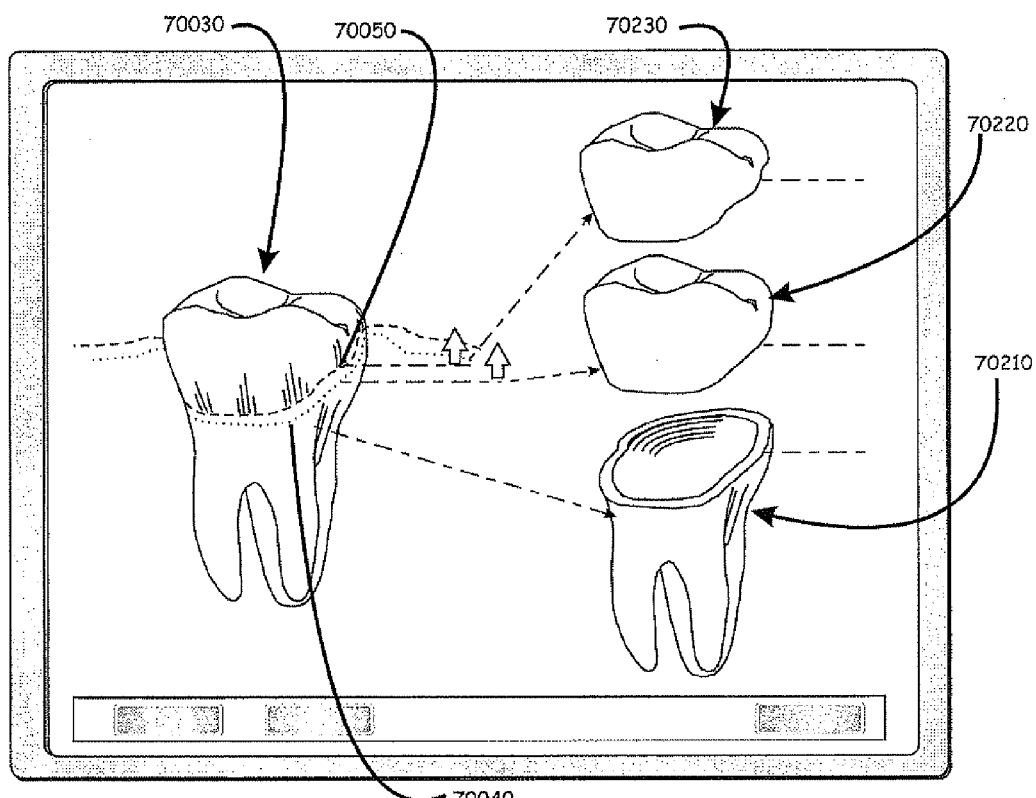
FIG. 83 illustrates the division or separation of parts of a virtual model.

As perhaps best shown in FIGS. 79 and 81, the step of forming can also include copying at least portions of the modeled virtual crown portion 70070 to form a base shape of the virtual prosthesis interface, reducing dimensions of the at least portions of the modeled virtual crown portion 70070 to define a virtual prosthesis interface model at 70110, and as shown in FIG. 81, combining the virtual prosthesis interface model 70110 having reduced dimensions with the virtual root body portion model 70060 to form the virtual dental implant body 70080.

As shown in FIGS. 79-80, according to this configuration, the steps can also include forming the virtual occlusally-facing dental prosthesis component 70100 (FIG. 82) modeling an occlusally-facing dental prosthesis component, such as, for example, a virtual crown component 70100. According to such configuration, the step of forming the virtual crown component 70100 includes forming a complementing virtual dental implant body-receiving (interface) surface 70120 (FIG. 80) modeling a physical complementing interface surface to receive occlusally-facing portions of the dental implant body 70080 to create a form locking fit therebetween. This can be accomplished by copying at least portions of the modeled virtual crown portion 70070 to form a base shape of the complementing interface surface 70120 of the virtual crown portion 70100, reducing dimensions of the at least portions of the modeled virtual crown portion 70070 to form the complementing interface surface model shown at 70130 (FIG. 79), and combining the virtual crown portion model 70070 with the complementing interface surface model 70130 as shown in FIG. 80 to form the virtual crown portion 70100 shown in FIG. 82.

Note, as shown in FIG. 79, the dimensions of the complementing interface surface model 70130 is reduced to be smaller than the dimensions of the virtual crown portion 70070, and the dimensions of virtual prosthesis interface model 70110 is reduced to be smaller than the dimensions of the complementing interface surface model 70130. These dimensional reductions in the three-dimensional size of the pairs of surfaces that build an interface and/or form the form-locking fit, are to account for manufacturing tolerances and to account for a certain thickness of the layer of adhesive, cement or glass solder, etc., generally in the range of 50 to 300 micrometers, but preferably approximately 100 micrometers.

FIGS. 83-89 further detail exemplary steps of designing the three-piece dental implant 57000 (FIGS. 71 & 89) based upon the three-dimensional virtual model 70030 of at least portions of the non-functional natural tooth 70000. According to an example of the three-piece dental implant body configuration, as perhaps best shown in FIG. 83, the step of forming a virtual dental implant body 70200 (FIG. 88) includes separating a portion of the three-dimensional virtual model 70030 along the virtual bone-facing gum line representation 70040 to form a modeled virtual root portion 70210 and a first modeled virtual crown portion 70220 (used to form the modeled transgingival cap portion), and copying a portion of the modeled crown portion separated at the outer gum line 70002 to form a second virtual crown portion model 70230 modeling the physical crown.

Figure 84:
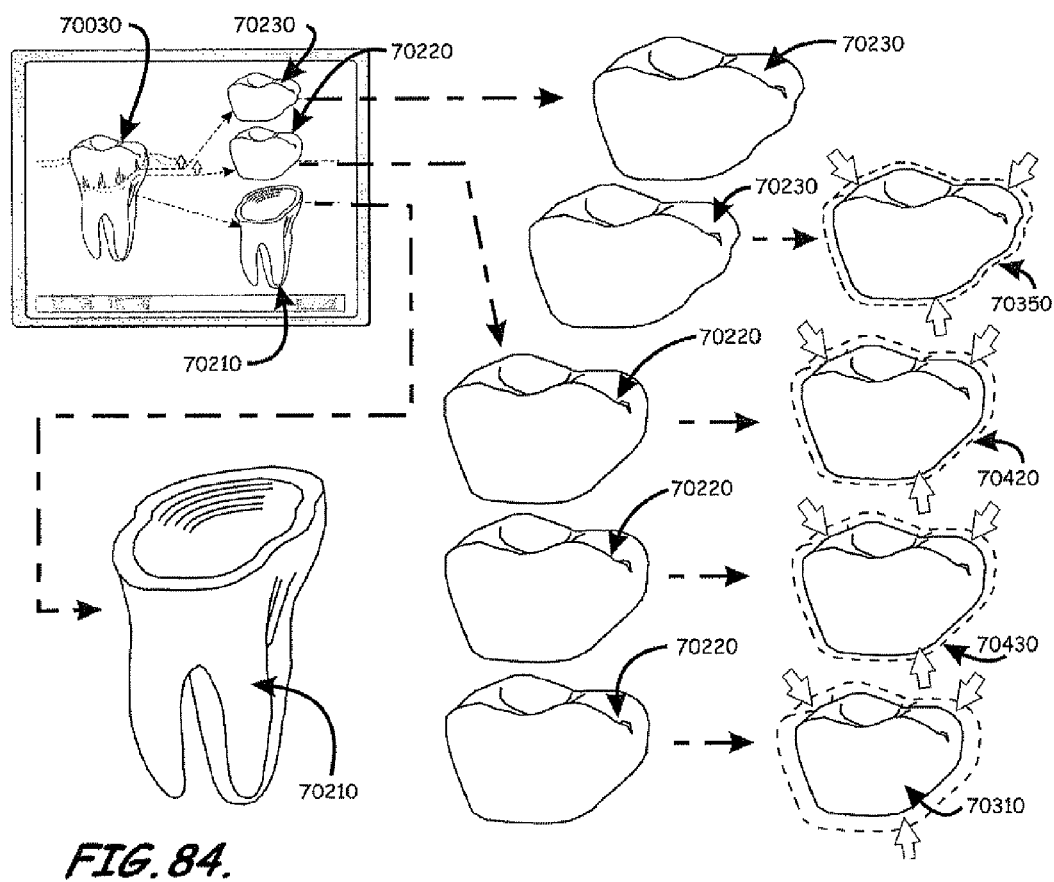
FIG. 84 illustrates copying of portions of the divided virtual model.

As perhaps best shown in FIG. 84, the step of forming the virtual dental implant body 70200 further includes copying at least portions of the modeled first virtual crown portion 70220 to form a base shape of the prosthesis interface 70240 (FIG. 88) and reducing dimensions of the at least portions of the modeled first virtual crown portion 70220 to define a prosthesis interface model 70310. As shown in FIG. 85, the step of forming also includes combining the virtual prosthesis interface model 70310 with the virtual root body portion model 70210 to form the virtual dental implant body 70200 (FIG. 88).

As shown in FIGS. 84, and 86-88, the steps can also include forming a virtual occlusally-facing dental prosthesis component modeling an occlusally-facing dental prosthesis component, such as, for example, a virtual crown component 70320 (FIG. 88) and/or a virtual transgingival cap component 70330 (FIG. 88). The virtual crown component 70320 can be formed by employing the procedures described with respect to forming the virtual crown component in the two-piece configuration, to include copying at least portions of the modeled virtual crown portion 70230 to form a base shape of a complementing interface surface 70340 (FIG. 87) of the virtual crown portion, reducing dimensions of the at least portions of the modeled second virtual crown portion 70230 to form the complementing interface surface model shown at 70350 (FIGS. 84 and 87), and as shown in FIG. 87, combining the virtual crown portion model 70230 with the complementing interface surface model 70350 to form the virtual crown portion 70320 (FIG. 88).

As shown in FIGS. 84 and 86, the transgingival cap can be formed using a similar set of procedures. For example, the step of forming the transgingival cap component 70330 (FIG. 88) can include forming a complementing virtual dental implant body-receiving (interface) surface 70410 (FIG. 86) modeling a complementing interface surface to receive occlusally-facing portions of the dental implant body. This can be accomplished by copying at least portions of the first modeled virtual crown portion 70220 (modeling the transgingival cap portion) cut along the bone-facing gum line representation 70040 to form a base shape of the complementing interface surface 70410 of the transgingival cap portion 70330 and to form the occlusally-facing surface of the transgingival cap portion 70330, reducing dimensions of the at least portions of the first modeled virtual crown portion 70220 modeling the transgingival cap portion shown at 70420, reducing dimensions of the at least portions of the first modeled virtual crown portion 70220 modeling the complementing interface surface 70410 shown at 70430, and as shown in FIG. 86, combining the virtual transgingival cap model 70420 with the complementing interface surface model 70430 to form the virtual transgingival cap 70330 (FIG. 88).

Note, the dimensions of the complementing interface surface model 70230 is reduced to be smaller than the dimensions of the virtual crown portion 70070, the dimensions of the transgingival cap portion model 70420 is reduced to be smaller than the dimensions of complementing interface surface model 70430, and the dimensions of virtual prosthesis interface model 70310 is reduced to be smaller than the dimensions of the complementing interface surface model 70430. These dimensional reductions in the three-dimensional size of the pairs of surfaces that build an interface and/or form the form-locking fit are to account for manufacturing tolerances and to account for a certain thickness of the layer of adhesive, cement or glass solder, etc., generally in the range of 50 to 300 micrometers, but preferably approximately 100 micrometers.

One of ordinary skill in the art will recognize that various aspects of the invention as explained above can readily be combined with each other.

The meaning of "CAD" shall include but shall not be limited to any and all technology of computer aided design.

The meaning of "CAM" shall include but shall not be limited to any and all technology of computer aided manufacturing.

The meaning of "CNC" shall include but shall not be limited to any and all technology of computer numerical control as it relates to manufacturing machinery and systems, including but not limited to rapid prototyping devices and systems.

The meaning of "rapid prototyping" shall include but shall not be limited to all technologies qualified for manufacturing of copies of virtual three-dimensional objects and also technologies qualified for mass customization or the mass production of copies of customized or adapted geometries to the needs of an individual patient. Rapid prototyping in this context shall include but not be limited to manufacturing technologies based on the digital data, by a process that includes depositing material, in accordance with the digital data, layer-by-layer in a plurality of layers each constituting a two-dimensional cross section of a solid object having an edge defined by data of the three-dimensional surface, the layers being stacked in a third dimension to form the solid object having a three-dimensional surface defined by the data. All such rapid prototyping technologies can be used directly to manufacture the part of interest, for example, by selective laser sintering or indirectly by fabricating first, e.g., a resin or wax sample of the part of interest and second using for example, "lost-wax" casing to duplicate such sample and fabricate therewith the part of interest. It also includes sintering techniques where the "green" body is printed in response to computerized, numerical controlled (CNC) data and then sintered to its final material properties. Sintering in this context includes pressure and heat.

The meaning of "rapid prototyping" shall be used in its broadest technical sense, where individualized parts are made from virtual representations, and shall include respective additive, subtractive and forming technologies used to three-dimensionally shape work pieces. The meaning of "additive shaping" shall include but shall not be limited to selective laser melting, selective laser sintering, stereolithography, 3-D printing or depositing of wax, wax-bound powders, adhesive-bound powders, slurries. The meaning of "subtractive shaping" shall include but shall not be limited to 3D laser shaping, CNC-grinding, CNC-turning, and CNC-milling technologies, and other machining and finishing technologies. The meaning of "shape forming" shall include but shall not be limited to near net-shape forming technologies, CNC-stamping, and CNC-pressing and casting technologies.

The meaning of "body" of an artificial tooth shall include but shall not be limited to the part of the prosthesis representing a root structure for periodontal or osseointegration or the combined part of the prosthesis representing a root structure for periodontal or osseointegration and a support structure for a crown or a bridge.

The meaning of "prosthesis" shall include any substantially artificially shaped part of any natural and artificial material. In this sense a dental prosthesis for periodontal integration would have to be distinguished to any human tooth used for intentional re-implantation.

Whenever the context requires, the word "prosthesis" shall be deemed to include the word "implant" and vice versa.

"3D" shall mean three-dimensional.

The meaning of "CT" shall include but shall not be limited to any and all technology of computed tomography.

"CBCT" shall mean cone beam computed tomography and shall include "DVT" technology.

"DVT" shall mean digital volume tomography.

"Three-dimensional X-ray image" shall include but shall not be limited to voxel data, volumetric X-ray data, at least two two-dimensional X-ray images in DICOM format, a stack of two-dimensional X-ray images, data received from CBCT or other CT, MRT, ultrasonic and TOF devices, or any combination thereof.

The meaning of "MRT" shall include but shall not be limited to any and all technology of magnetic resonance tomography.

The meaning of "TOF" shall include but shall not be limited to any and all technology employing Time-of-Flight procedures.

The meaning of "imaging" and "scanning" shall include but shall not be limited to any and all technology of acquiring two-dimensional and/or three-dimensional data of physical objects or parts of a human body.

The meaning of clinical "imaging data" shall include but shall not be limited to in-vivo and in-vitro processes that result in any anatomical data of the anatomy of a human being. In this context the term data shall include but shall not be limited to two-dimensional and three-dimensional data.

The meaning of three-dimensional data shall include but shall not be limited to surface (e.g., triangulated data) and volumetric (e.g., voxel) data.

The meaning of "periodontal tissue" shall include but shall not be limited to any soft tissue surrounding a tooth.

The meaning of "periodontal ligature", "ligament" or "periodontal ligament" shall include but shall not be limited to the fibrous connective tissue (e.g., human gingival fibroblasts) interface usually located between a human tooth and the anatomical structure of the jaw of a human being.

The meaning of each one of the following: "periodontal integration", "parodontal integration", "integration into the periodont", "integration into the parodont", "integration into the dental soft-tissue", "integration into the dental ligament" and alike word constructions shall include but shall not be limited to the integration into the periodontal ligament structure or perio-type tissue or any other biological structure of the human dental anatomy except osseointegration. In this sense the term periodontal integration shall include but shall not be limited to the integration of a prosthesis to be adopted and held by periodontal ligament tissue of a human being.

In this sense a prostheses for periodontal integration would have to be distinguished to any osseointegrated implant.

The meaning of "cavity" shall include but shall not be limited to the periodontal cavity, a cavity of the jaw bone structure, a cavity of the alveolus or a combination thereof.

The meaning of "extraction socket" shall include prepared or unprepared extraction sockets. The meaning of "prepared" shall include but shall not be limited to being surgically pared, abraded, scraped or curetted by mechanical instruments or laser technology based devices.

The meaning of "replacement", "to replace", "to be replaced" shall include but shall not be limited to any substitution, where one object fills the former position of another object. In the context of the foregoing such substitution can be performed at any time, so that for example, the term replacement shall not be limited to a replacement in a timely manner.

The meaning of a "manufactured one-piece" object shall not be limited to homogeneous objects, and shall include but shall not be limited to manufactured assemblies, objects that are coated, objects that are consisting of more than one pieces or materials bonded together or any combination thereof.

The meaning of a "clinical one-step" process or a "clinical one-step" method shall include but shall not be limited to a series clinical process or method steps performed in one or more clinical events as long as no further iteration is required that includes clinical process or method steps and process or method steps that cannot be performed chair-side.

The meaning of "immediate load" of an implant shall include but shall not be limited to any all integration concepts of implants where the occlusal portion of the implant (e.g., the crown portion facing the opponent jaw) is not protected against the alternate load of mastication by additional protective means.

The meaning of "configured to be integrated into the existing occlusion of the patients dentition" shall include but shall not be limited to any shaping of a crown or a crown-like portion of a prosthesis that contacts or otherwise substantially fills the gap between adjacent crowns, and any shaping that contacts or otherwise substantially interacts with the opponent crowns of the dentition in the process of masticating food.

In dentistry, the term occlusion is used to refer to the manner in which the teeth from upper and lower arches come together when the mouth is closed. The meaning of "occlusion" shall mean but shall not be limited to the manner the teeth of the upper or lower arch are fitting and coming in contact with each other while the mouth is closed or during chewing (articulation). It shall also include the fit and contact of adjacent teeth within one arch. The meaning of "integrated into the occlusion" shall include but shall not be limited to the configuration and integration of the fit and contact situation of a prosthesis within the existing or new build occlusion within the same and the opponent arch.

The words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The various embodiments and aspects of embodiments of the invention disclosed herein are to be understood not only in the order and context specifically described in this specification, but to include any order and any combination thereof. Whenever the context requires, all words used in the singular number shall be deemed to include the plural and vice versa. Words which import one gender shall be applied to any gender wherever appropriate. Whenever the context requires, all options that are listed with the word "and" shall be deemed to include the world "or" and vice versa, and any combination thereof. The titles of the sections of this specification and the sectioning of the text in separated paragraphs are for convenience of reference only and are not to be considered in construing this specification.

Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements.

In the drawings and specification, there have been disclosed embodiments of the invention, and although specific terms are employed, the terms are used in a descriptive sense only and not for purposes of limitation, the scope of the invention being set forth in the following claims. It must be understood that the illustrated embodiment has been set forth only for the purposes of example and that it should not be taken as limiting the invention. It will be apparent to those skilled in the art that alterations, other embodiments, improvements, details and uses can be made consistent with the letter and spirit of the disclosure herein and within the scope of this disclosure patent, which is limited only by the following claims, construed in accordance with the patent law, including the doctrine of equivalents.

This patent application is a non-provisional and claims priority to and the benefit of U.S. Patent Application No. 61/454,450 filed on Mar. 18, 2011, and is a continuation-in-part of and claims priority to them the benefit of U.S. patent application Ser. No. 12/763,001, filed Apr. 19, 2010, which claims priority to and the benefit of U.S. patent application Ser. No. 11/724,261, filed Mar. 15, 2007, now U.S. Pat. No. 7,708,557, which is a continuation-in-part of co-pending U.S. patent application Ser. No. 11/549,782 filed on Mar. 16, 2006, each incorporated by reference in its entirety In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification. In the claims which follow, reference characters if used to designate claim steps are provided for convenience of description only, and are not intended to imply any particular order for performing the steps.

The invention claimed is:

1. A method of manufacturing a dental implant to replace a non-functional natural tooth positioned in a jawbone of a specific pre-identified patient, the method comprising the steps of:

receiving data describing an in-vivo dental anatomy of the specific pre-identified patient associated with the non-functional natural tooth prior to removal from the jawbone of the specific pre-identified patient, the in-vivo dental anatomy to include a three-dimensional outer surface shape of at least portions of a root of the non-functional natural tooth, and a three-dimensional outer surface shape of at least portions of a crown of the non-functional natural tooth and surrounding gum tissue to define received data comprising received in-vivo imaging data;

forming at least one three-dimensional virtual model of at least portions of the non-functional natural tooth positioned in the jawbone of the specific pre-identified patient responsive to at least portions of the received in-vivo imaging data, the at least one three-dimensional virtual model of the non-functional natural tooth including a modeled virtual root portion and a modeled virtual crown portion; and designing the dental implant based upon the at least one three-dimensional virtual model of at least portions of the non-functional natural tooth, the step of designing the dental implant including the steps of:

deriving a virtual occlusally-facing prosthesis interface shape from a virtual reduction of at least a substantial portion of the modeled virtual crown portion;

forming a virtual dental implant body modeling a dental implant body, the virtual dental implant body including the virtual occlusually-facing prosthesis interface shape modeling a prosthesis interface of the dental implant body to receive an occlusally-facing dental prosthesis component, the virtual occlusually-facing prosthesis interface shape to include a substantially three-dimensionally contoured custom surface shape correlated to a corresponding surface shape of the modeled virtual crown portion, and forming a virtual occlusally-facing dental prosthesis component modeling an occlusally-facing dental prosthesis component, the step of forming the virtual occlusally-facing dental prosthesis component including forming a complementing virtual dental implant body-receiving surface to define a complementing virtual interface surface modeling a complementing interface surface to receive occlusally-facing portions of the dental implant body, the prosthesis interface and the complementing interface surface to create a form locking fit therebetween.

2. A method as defined in claim 1, wherein substantial portions of the three-dimensionally contoured custom implant body surface shape of the virtual prosthesis interface have a substantially asymmetrically contoured implant body surface shape.

3. A method as defined in claim 1, wherein the virtual occlusally-facing dental prosthesis component comprises a virtual crown component, and wherein the step of forming a virtual dental implant body includes:

separating a portion of the at least one three-dimensional virtual model along a virtual outer gum line representation, the separated portion including the modeled virtual root portion to define a virtual root body portion model;

copying at least portions of the modeled virtual crown portion, the copy to include at least portions of the modeled virtual crown portion forming a base shape of the virtual prosthesis interface;

reducing dimensions of the at least portions of the modeled virtual crown portion to define a virtual prosthesis interface model; and combining the virtual prosthesis interface model with the virtual root body portion model to form the virtual dental implant body.

4. A method as defined in claim 3, wherein the step of receiving data describing the in-vivo dental anatomy associated with the non-functional natural tooth positioned in the jawbone of the specific pre-identified patient and data describing the three-dimensional outer surface shape of at least portions of the crown of the non-functional natural tooth and surrounding gum tissue is performed by a computer having memory and having dental implant design program product stored in the memory of the computer; and wherein the steps of separating the portion of the at least one three-dimensional virtual model along the virtual outer gum line representation, copying at least portions of the modeled virtual crown portion, reducing dimensions of the at least portions of the modeled virtual crown portion, and combining the virtual prosthesis interface model with the virtual root body portion model to form the virtual dental implant body, and the step of forming the virtual occlusally-facing dental prosthesis component, are performed on a graphical user interface operably coupled to the computer responsive to user manipulation of an input device.

5. A method as defined in claim 4, wherein the computer is adapted to perform the step of producing a set of digital data virtually defining the three-dimensionally contoured custom implant body surface shape, and wherein the method further comprises performing one or more of the following steps:

employing a machining process performed by a computer numerical control (CNC) based machining apparatus to form substantial portions of the dental implant body including the prosthesis interface responsive to the set of digital data; and employing a rapid prototyping process performed by a computer numerical control (CNC) based rapid prototyping apparatus to form substantial portions of the dental implant body including the prosthesis interface responsive to the set of digital data.

6. A method as defined in claim 1, wherein the virtual prosthesis interface has an outward-facing circumferential edge, the method further comprising the step of designing the dental implant, to include the step of:

shaping the outward-facing circumferential edge of the virtual prosthesis interface of the virtual dental implant body to substantially match a shape of a corresponding outer gum line surrounding the dental implant described in the received data describing the gum tissue surrounding the non-functional natural tooth prior to removal of the non-functional natural tooth from the jawbone of the specific pre-identified patient.

7. A method as defined in claim 6, wherein the outward-facing circumferential edge of the virtual prosthesis interface models an outward-facing edge of the prosthesis interface, the method further comprising the step of fabricating the dental implant, to include the step of:

shaping the outward-facing circumferential edge of the prosthesis interface of the dental implant to substantially match a shape of the corresponding outer gum line surrounding the dental implant described in the received data describing the gum tissue surrounding the non-functional natural tooth prior to removal of the non-functional natural tooth from the jawbone of the specific pre-identified patient.

8. A method as defined in claim 1, wherein the step of forming the virtual dental implant body includes:

separating a portion of the at least one three-dimensional virtual model along a virtual bone-facing gum line representation, the separated portion including the modeled virtual root portion to define a virtual root body portion model, and copying at least portions of the modeled virtual crown portion, the copy to include at least portions of the modeled virtual crown portion forming a base shape of the prosthesis interface, reducing dimensions of the at least portions of the modeled virtual crown portion to define a prosthesis interface model, and combining a virtual prosthesis interface model with the virtual root body portion model to form the virtual dental implant body; and wherein the step of forming the virtual occlusally-facing dental prosthesis component comprises defining virtual dimensions of an occlusally-facing surface to define a virtual crown component model modeling a crown component, the dimensions of virtual crown component model being larger than the dimensions of the virtual prosthesis interface model.

9. A method as defined in claim 1, wherein the prosthesis interface has an outward-facing circumferential edge, the method further comprising the step of fabricating the dental implant, to include:

shaping the outward-facing circumferential edge of the prosthesis interface of the dental implant to substantially match a shape of a corresponding bone crest line surrounding the dental implant as described in the received data describing the in-vivo dental anatomy associated with a non-functional natural tooth prior to removal of the non-functional natural tooth from the jawbone of the specific pre-identified patient.

10. A method as defined in claim 1, wherein the step of receiving data describing the in-vivo dental anatomy associated with the non-functional natural tooth positioned in the jawbone of the specific pre-identified patient and data describing the three-dimensional outer surface shape of at least portions of a crown of the non-functional natural tooth and surrounding gum tissue includes the steps of:

receiving data describing a three-dimensional X-ray image of at least portions of the patient's dentition defining x-ray image data, and receiving data describing one of the following: a physical impression of a dental anatomy and a surface scan of the dental anatomy, defining impression image data made prior to removal of the non-functional natural tooth from the jawbone of the specific patient; and wherein the step of forming the at least one three-dimensional virtual model of at least portions of the non-functional natural tooth includes:

combining the x-ray image data and impression image data, and forming the at least one three-dimensional virtual model of the non-functional natural tooth responsive to the x-ray image data and the impression image data.

11. A method as defined in claim 1, further comprising the step of fabricating the dental implant body, to include:

shaping the prosthesis interface to have the three-dimensionally contoured custom implant body surface shape at least partially correlated to a surface shape of an occlusally-facing surface of the crown of the nonfunctional tooth to thereby create the form locking fit with the complementing interface surface of the occlusally-facing dental prosthesis component when positioned therein.

12. A method as defined in claim 11, further comprising the step of fabricating the occlusally-facing dental prosthesis component, to include:
shaping the complementing interface surface of the occlusally-facing dental prosthesis component to have a three-dimensionally contoured surface shape substantially dimensionally matching the three-dimensionally contoured custom implant body surface shape of the prosthesis interface to thereby create the form locking fit therebetween.

13. A method as defined in claim 1, wherein the dental implant body includes a root body portion, the method further comprising the step of fabricating the dental implant body, to include the step of:
shaping an outer surface of the root body portion of the dental implant body to have a custom three-dimensional surface shape approximately dimensionally matching a three-dimensional inner-surface shape of corresponding surface portions of one or more intra jawbone anatomical features associated with the non-functional natural tooth of the specific pre-identified patient.

14. A method as defined in claim 1, wherein the virtual dental implant body comprises a root body section modeling a root body section of the dental implant body, the root body section of the dental implant body having a three-dimensional outer surface shape approximately dimensionally matching a three-dimensional surface shape of corresponding surface portions of one or more intra jawbone anatomical features associated with the non-functional natural tooth of the specific pre-identified patient, the one or more intra jawbone anatomical features comprising at least one of the following: a three-dimensional outer surface shape of the root portion of the non-functional natural tooth of the specific pre-identified patient, a three-dimensional inner surface shape of a bone socket for the root portion of the non-functional natural tooth of the specific pre-identified patient, and a combination of the three-dimensional outer surface shape of the root portion and three-dimensional inner surface shape of the bone socket for the root portion of nonfunctional natural tooth of the jawbone of the specific pre-identified patient.

15. A method as defined in claim 1, wherein the prosthesis interface has an outward-facing circumferential edge, wherein the dental implant body includes a longitudinally extending axis, and wherein a center portion of the prosthesis interface is substantially raised in a direction of the longitudinally extending axis over the outward-facing circumferential edge to create a male portion of the form locking fit with respect to the occlusally-facing dental prosthesis component when positioned thereon.

16. A method as defined in claim 1, wherein the dental implant body includes a root body portion having an occlusal-facing surface, a lingual-facing side portion, a labial-facing side portion, and a pair of proximal-facing side portions, and wherein the three-dimensionally contoured implant body surface shape of the prosthesis interface includes a substantially asymmetric positive raising extending from the dental implant body, and wherein the method further comprises the step of fabricating the dental implant body to include the step of:
shaping the substantially asymmetric positive raising to have a first rising contour extending from portions of the occlusal-facing surface of the root body portion adjacent a center of the lingual-facing side portion and a second rising contour extending from portions of the occlusal-facing surface of the root body portion adjacent a center of the labial-facing side, the second rising contour being substantially different than the first rising contour when viewed along a cross-section of the dental implant extending between the lingual-facing side portion and labial-facing side portion and when viewed along a cross-section of the dental implant extending between the labial-facing side portion and lingual-facing side portion, respectively.

17. A method as defined in claim 16, wherein the occlusally-facing dental prosthesis component comprises a crown custom manufactured for the specific pre-identified patient receiving the dental implant, and wherein an outline of a cross-section of the substantially asymmetric positive raising is shaped to follow an outline of a corresponding cross-section of the crown custom manufactured for the pre-identified patient.

18. A method as defined in claim 1, wherein the prosthesis interface has an outward-facing circumferential edge, wherein the dental implant body includes a longitudinally extending axis, and wherein a center portion of the prosthesis interface is substantially indented in a direction of the longitudinally extending axis over the outward-facing circumferential edge to create a female portion of the form locking fit with respect to the occlusally facing dental prosthesis component when positioned thereon.

19. A method as defined in claim 1, further comprising the steps of:
fabricating the dental implant body having the prosthesis interface, to include shaping the prosthesis interface to have the three-dimensionally contoured custom implant body surface shape at least partially correlated to a surface shape of an occlusally-facing surface of the crown of the nonfunctional tooth; and
imaging the prosthesis interface to thereby obtain prosthesis interface imaging data describing an as-manufactured three-dimensional asymmetrical contour of the prosthesis interface, and
wherein the step of forming the complementing virtual interface surface includes forming the complementing interface surface of the virtual occlusally-facing dental prosthesis component to dimensionally match the three-dimensionally contoured custom implant body surface shape of the prosthesis interface responsive to the prosthesis imaging data to thereby enhance accuracy of the form locking fit.

20. A method as defined in claim 19, further comprising the step of fabricating the occlusally-facing dental prosthesis component to include shaping the complementing interface surface of the occlusally-facing dental prosthesis component to match the three-dimensionally contoured custom implant body surface shape of the imaged prosthesis interface.

21. A method of manufacturing a dental implant to replace a non-functional natural tooth positioned in a jawbone of a specific pre-identified patient, the method comprising the step of:
designing the dental implant based upon at least one virtual model of at least portions of a non-functional natural tooth positioned in a jawbone of a specific pre-identified patient, the at least one three-dimensional virtual model of the non-functional natural tooth including a modeled virtual root portion and a modeled virtual crown portion, the step of designing the dental implant including the steps of:
  forming a virtual dental implant body modeling a dental implant body, the virtual dental implant body having a virtual occlusally-facing prosthesis interface modeling a prosthesis interface of the dental implant body to receive an occlusally-facing dental prosthesis component, the step of forming the virtual dental implant body including forming the virtual occlusally-facing prosthesis interface to include a three-dimensionally contoured custom implant interface surface shape derived from a virtually reduced model of a substantial portion of the modeled virtual crown portion, the three-dimensionally contoured custom implant interface surface shape correlated to a corresponding surface shape of the modeled virtual crown portion, and
  forming a virtual occlusally-facing dental prosthesis component modeling an occlusally-facing dental prosthesis component, the step of forming the virtual occlusally-facing dental prosthesis component including forming a complementing virtual dental implant body-receiving surface to define a complementing virtual interface surface modeling a complementing interface surface to receive occlusally-facing portions of the dental implant body, the prosthesis interface and the complementing interface surface to create a form locking fit therebetween.

22. A method as defined in claim 21, wherein substantial portions of the three-dimensionally contoured custom implant body surface shape of the virtual prosthesis interface have a substantially asymmetrically contoured implant body surface shape.

23. A method as defined in claim 21, further comprising the steps of:
  receiving data describing an in-vivo dental anatomy associated with the non-functional natural tooth positioned in the jawbone of the specific pre-identified patient to include a three-dimensional outer surface shape of at least portions of a root of the non-functional natural tooth and data describing a three-dimensional outer surface shape of at least portions of a crown of the non-functional natural tooth and surrounding gum tissue prior to removal of the non-functional natural tooth from the jawbone of the specific pre-identified patient, to define received data; and
  forming the at least one three-dimensional virtual model of at least portions of the non-functional natural tooth positioned in the jawbone of the specific pre-identified patient responsive to at least portions of the received data.

24. A method as defined in claim 23, wherein the step of receiving data describing the in-vivo dental anatomy associated with the non-functional natural tooth positioned in the jawbone of the specific pre-identified patient and data describing a three-dimensional outer surface shape of at least portions of a crown of the non-functional natural tooth and surrounding gum tissue includes the steps of:
  receiving data describing a three-dimensional X-ray image of at least portions of the patient's dentition defining x-ray image data, and
  receiving data describing one of the following: a physical impression of a dental anatomy and a surface scan of the dental anatomy, defining impression image data made prior to removal of the non-functional natural tooth from the jawbone of the specific patient; and
  wherein the step of forming the at least one three-dimensional virtual model of at least portions of the non-functional natural tooth includes:
    combining the x-ray image data and impression image data, and
    forming the at least one three-dimensional virtual model of the non-functional natural tooth responsive to the x-ray image data and the impression image data.

25. A method as defined in claim 21, wherein the virtual occlusally-facing dental prosthesis component comprises a virtual crown component, and wherein the step of forming the virtual dental implant body includes:
  separating a portion of the at least one three-dimensional virtual model along a virtual outer gum line representation, the separated portion including the modeled virtual root portion to define a virtual root body portion model;
  copying at least portions of the modeled virtual crown portion, the copy to include at least portions of the modeled virtual crown portion forming a base shape of the virtual prosthesis interface;
  reducing dimensions of the at least portions of the modeled virtual crown portion to define a virtual prosthesis interface model; and
  combining the virtual prosthesis interface model with the virtual root body portion model to form the virtual dental implant body.

26. A method as defined in claim 25, further comprising the step of:
  receiving data describing an in-vivo dental anatomy associated with the non-functional natural tooth positioned in the jawbone of the specific pre-identified patient to include a three-dimensional outer surface shape of at least portions of a root of the non-functional natural tooth and data describing a three-dimensional outer surface shape of at least portions of a crown of the non-functional natural tooth and surrounding gum tissue prior to removal of the non-functional natural tooth from the jawbone of the specific pre-identified patient, to define received data, the step of receiving data describing the in-vivo dental anatomy associated with the non-functional natural tooth positioned in the jawbone of the specific pre-identified patient and data describing the three-dimensional outer surface shape of at least portions of the crown of the non-functional natural tooth and surrounding gum tissue being performed by a computer having memory and having dental implant design program product stored in the memory; and
  wherein the steps of separating the portion of the at least one three-dimensional virtual model along the virtual outer gum line representation, copying at least portions of the modeled virtual crown portion, reducing dimensions of the at least portions of the modeled virtual crown portion, and combining the virtual prosthesis interface model with the virtual root body portion model to form the virtual dental implant body, and the step of forming the virtual occlusally-facing dental prosthesis component, are performed on a graphical user interface operably coupled to the computer responsive to user manipulation of an input device.

27. A method as defined in claim 26, wherein the computer is adapted to perform the step of producing a set of digital data virtually defining the three-dimensionally contoured custom implant body surface shape, and wherein the method further comprises performing one or more of the following steps:
employing a machining process performed by a computer numerical control (CNC) based machining apparatus to form substantial portions of the dental implant body including the prosthesis interface responsive to the set of digital data; and
employing a rapid prototyping process performed by a computer numerical control (CNC) based rapid prototyping apparatus to form substantial portions of the dental implant body including the prosthesis interface responsive to the set of digital data.

28. A method as defined in claim 21, wherein the virtual prosthesis interface has an outward-facing circumferential edge, the method further comprising the step of designing the dental implant, to include the step of:
shaping the outward-facing circumferential edge of the virtual prosthesis interface of the virtual dental implant body to substantially match a shape of a corresponding outer gum line surrounding the dental implant described in image data describing the gum tissue surrounding the non-functional natural tooth prior to removal of the non-functional natural tooth from the jawbone of the specific pre-identified patient.

29. A method as defined in claim 28, wherein the outward-facing circumferential edge of the virtual prosthesis interface models an outward-facing edge of the prosthesis interface, the method further comprising the step of fabricating the dental implant, to include the step of:
shaping the outward-facing circumferential edge of the prosthesis interface of the dental implant to substantially match a shape of the corresponding outer gum line surrounding the dental implant described in the image data describing the gum tissue surrounding the non-functional natural tooth prior to removal of the non-functional natural tooth from the jawbone of the specific pre-identified patient.

30. A method as defined in claim 21,
wherein the step of forming the virtual dental implant body includes:
separating a portion of the at least one three-dimensional virtual model along a virtual bone-facing gum line representation, the separated portion including the modeled virtual root portion to define a virtual root body portion model,
copying at least portions of the modeled virtual crown portion, the copy to include at least portions of the modeled virtual crown portion forming a base shape of the prosthesis interface,
reducing dimensions of the at least portions of the modeled virtual crown portion to define a prosthesis interface model, and
combining a virtual prosthesis interface model with the virtual root body portion model to form the virtual dental implant body; and
wherein the step of forming the virtual occlusally-facing dental prosthesis component comprises defining virtual dimensions of an occlusally-facing surface to define a virtual crown component model modeling a crown component, the dimensions of virtual crown component model being larger than the dimensions of the virtual prosthesis interface model.

31. A method as defined in claim 21, wherein the prosthesis interface has an outward-facing circumferential edge, the method further comprising the step of fabricating the dental implant, to include:
shaping the outward-facing circumferential edge of the prosthesis interface of the dental implant to substantially match a shape of a corresponding bone crest line surrounding the dental implant as described in image data describing an in-vivo dental anatomy associated with a non-functional natural tooth prior to removal of the non-functional natural tooth from the jawbone of the specific pre-identified patient.

32. A method as defined in claim 21, further comprising the step of fabricating the dental implant body, to include:
shaping the prosthesis interface to have the three-dimensionally contoured custom implant body surface shape at least partially correlated to a surface shape of an occlusally-facing surface of a crown of the nonfunctional tooth to thereby create the form locking fit with the complementing interface surface of the occlusally-facing dental prosthesis component when positioned therein.

33. A method as defined in claim 32, further comprising the step of fabricating the occlusally-facing dental prosthesis component, to include:
shaping the complementing interface surface of the occlusally-facing dental prosthesis component to have a three-dimensionally contoured surface shape substantially dimensionally matching the three-dimensionally contoured custom implant body surface shape of the prosthesis interface to thereby create the form locking fit therebetween.

34. A method as defined in claim 21, wherein the dental implant body includes a root body portion, the method further comprising the step of fabricating the dental implant body, to include the step of:
shaping an outer surface of the root body portion of the dental implant body to have a custom three-dimensional surface shape approximately dimensionally matching a three-dimensional inner-surface shape of corresponding surface portions of one or more intra jawbone anatomical features associated with the non-functional natural tooth of the specific pre-identified patient.

35. A method as defined in claim 21, wherein the virtual dental implant body comprises a root body section modeling a root body section of the dental implant body, the root body section of the dental implant body having a three-dimensional outer surface shape approximately dimensionally matching a three-dimensional surface shape of corresponding surface portions of one or more intra jawbone anatomical features associated with the non-functional natural tooth of the specific pre-identified patient, the one or more intra jawbone anatomical features comprising at least one of the following: a three-dimensional outer surface shape of a root portion of the non-functional natural tooth of the specific pre-identified patient, a three-dimensional inner surface shape of a bone socket for the root portion of the non-functional natural tooth of the specific pre-identified patient, and a combination of the three-dimensional outer surface shape of the root portion and three-dimensional inner surface shape of the bone socket for the root portion of nonfunctional natural tooth of the jawbone of the specific pre-identified patient.

36. A method as defined in claim 21, wherein the prosthesis interface has an outward-facing circumferential edge, wherein the dental implant body includes a longitudinally extending axis, and wherein a center portion of the prosthesis interface is substantially raised in a direction of the longitudinally extending axis over the outward-facing circumferential edge to create a male portion of the form locking fit with respect to the occlusally-facing dental prosthesis component when positioned thereon.

37. A method as defined in claim 21, wherein the dental implant body includes a root body portion having an occlusally-facing surface, a lingual-facing side portion, a labial-facing side portion, and a pair of proximal-facing side portions, and wherein the three-dimensionally contoured implant body surface shape of the prosthesis interface includes a substantially asymmetric positive raising extending from the dental implant body, and wherein the method further comprises the step of fabricating the dental implant body to include the step of:

shaping the substantially asymmetric positive raising to have a first rising contour extending from portions of the occlusally-facing surface of the root body portion adjacent a center of the lingual-facing side portion and a second rising contour extending from portions of the occlusally-facing surface of the root body portion adjacent a center of the labial-facing side, the second rising contour being substantially different than the first rising contour when viewed along a cross-section of the dental implant extending between the lingual-facing side portion and labial-facing side portion and when viewed along a cross-section of the dental implant extending between the labial-facing side portion and lingual-facing side portion, respectively.

38. A method as defined in claim 37, wherein the occlusally-facing dental prosthesis component comprises a crown custom manufactured for the specific pre-identified patient receiving the dental implant, and wherein an outline of a cross-section of the substantially asymmetric positive raising is shaped to follow an outline of a corresponding cross-section of the crown custom manufactured for the pre-identified patient.

39. A method as defined in claim 21, wherein the prosthesis interface has an outward-facing circumferential edge, wherein the dental implant body includes a longitudinally extending axis, and wherein a center portion of the prosthesis interface is substantially indented in a direction of the longitudinally extending axis over the outward-facing circumferential edge to create a female portion of the form locking fit with respect to the occlusally-facing dental prosthesis component when positioned thereon.

40. A method as defined in claim 21, further comprising the steps of:

fabricating the dental implant body having the prosthesis interface, to include shaping the prosthesis interface to have the three-dimensionally contoured custom implant body surface shape at least partially correlated to a surface shape of an occlusally-facing surface of a crown of the nonfunctional tooth; and imaging the prosthesis interface to thereby obtain prosthesis interface imaging data describing an as-manufactured three-dimensional asymmetrical contour of the prosthesis interface, and wherein the step of forming the complementing virtual interface surface includes forming the complementing interface surface of the virtual occlusally-facing dental prosthesis component to dimensionally match the three-dimensionally contoured custom implant body surface shape of the prosthesis interface responsive to the prosthesis imaging data to thereby enhance accuracy of the form locking fit.

41. A method as defined in claim 40, further comprising the step of fabricating the occlusally-facing dental prosthesis component to include shaping the complementing interface surface of the occlusally-facing dental prosthesis component to match the three-dimensionally contoured custom implant body surface shape of the imaged prosthesis interface.

42. A method of manufacturing a dental prosthesis to replace a non-functional natural tooth positioned in a jawbone of a specific pre-identified patient, the method comprising the steps of:

receiving 3D in-vivo imaging data describing an in-vivo dental anatomy of the specific pre-identified patient associated with the non-functional natural tooth prior to its removal from the jawbone of the specific pre-identified patient, the 3D in-vivo imaging data to include 3D in-vivo root imaging data of at least a portion of an in-vivo root of the non-functional natural tooth, and 3D in-vivo occlusal-facing imaging data of at least a portion of an in-vivo occlusal-facing portion of the non-functional natural tooth;

forming a virtual 3D implant component design model at least partially responsive to the 3D in-vivo imaging data; and manufacturing an implant component at least partially responsive to the virtual 3D implant component design model, the implant component including an implant component root portion and an occlusal-facing implant component interface, the implant component root portion having a substantially custom-shaped root portion surface of spatial dimension correlating to a corresponding virtual surface of spatial dimension represented in the 3D in-vivo root imaging data, the occlusal-facing implant component interface having a substantially custom-shaped interface surface of spatial dimension correlating to a corresponding virtually reduced model of spatial dimension derived from the 3D in-vivo occlusal-facing imaging data.

43. A method as defined in claim 42, wherein the 3D in-vivo occlusal-facing imaging data are imaging data of at least a portion of an in-vivo crown portion of the non-functional natural tooth.

44. A method as defined in claim 42, further comprising the step of:

forming a virtual 3D occlusal-facing prosthesis component design model at least partially responsive to the 3D in-vivo imaging data; and manufacturing an occlusal-facing prosthesis component at least partially responsive to the virtual 3D occlusal-facing prosthesis component design model.

45. A method as defined in claim 44, wherein the occlusal-facing prosthesis component having an apical-facing interface surface of spatial dimension at least partially correlates to the custom-shaped interface surface of spatial dimension of the occlusal-facing implant component interface of the implant component.

46. A method as defined in claim 45, wherein the apical-facing interface surface of spatial dimension of the occlusal-facing prosthesis component and the custom-shaped interface surface of spatial dimension of the occlusal-facing implant component interface of the implant component create a form locking fit therebetween.

* * * * *